US012297202B2

(12) United States Patent
Bhamidipati et al.

(10) Patent No.: US 12,297,202 B2
(45) Date of Patent: *May 13, 2025

(54) RIP1K INHIBITORS

(71) Applicant: Rigel Pharmaceuticals, Inc., South San Francisco, CA (US)

(72) Inventors: Somasekhar Bhamidipati, Foster City, CA (US); Simon Shaw, Oakland, CA (US); Ihab Darwish, San Carlos, CA (US); Jiaxin Yu, San Carlos, CA (US); Rao Kolluri, Foster City, CA (US); Vanessa Taylor, San Francisco, CA (US); Esteban Masuda, Menlo Park, CA (US); Mark Irving, San Francisco, CA (US)

(73) Assignee: Rigel Pharmaceuticals, Inc., South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/307,181

(22) Filed: Apr. 26, 2023

(65) Prior Publication Data

US 2023/0265100 A1    Aug. 24, 2023

Related U.S. Application Data

(63) Continuation of application No. 17/358,698, filed on Jun. 25, 2021, now Pat. No. 11,667,643.

(60) Provisional application No. 63/047,194, filed on Jul. 1, 2020.

(51) Int. Cl.
| | | |
|---|---|---|
| C07D 471/04 | (2006.01) | |
| A61K 31/55 | (2006.01) | |
| A61K 31/551 | (2006.01) | |
| A61K 31/553 | (2006.01) | |
| A61K 31/554 | (2006.01) | |
| A61P 9/00 | (2006.01) | |
| A61P 25/00 | (2006.01) | |
| A61P 29/00 | (2006.01) | |
| A61P 37/00 | (2006.01) | |
| C07D 487/04 | (2006.01) | |
| C07D 498/04 | (2006.01) | |
| C07D 498/14 | (2006.01) | |
| C07D 498/22 | (2006.01) | |
| C07D 513/04 | (2006.01) | |
| C07D 513/14 | (2006.01) | |
| C07D 519/00 | (2006.01) | |

(52) U.S. Cl.
CPC ......... C07D 487/04 (2013.01); C07D 471/04 (2013.01); C07D 498/04 (2013.01); C07D 498/22 (2013.01); C07D 513/14 (2013.01); C07D 519/00 (2013.01)

(58) Field of Classification Search
CPC .. C07D 471/04; C07D 487/04; C07D 498/04; C07D 498/14; C07D 498/22; C07D 513/04; C07D 513/14; C07D 519/00; A61K 31/55; A61K 31/551; A61K 31/553; A61K 31/554; A61P 9/00; A61P 25/00; A61P 29/00; A61P 37/00
See application file for complete search history.

(56) References Cited

U.S. PATENT DOCUMENTS

| | | |
|---|---|---|
| 8,658,689 B2 | 2/2014 | Cuny et al. |
| 9,556,152 B2 | 1/2017 | Harris |
| 9,624,202 B2 | 4/2017 | Jeong |
| 9,725,452 B2 | 8/2017 | Yuan et al. |
| 9,815,850 B2 | 11/2017 | Estrada |
| 9,896,458 B2 | 2/2018 | Estrada et al. |
| 10,815,206 B2 | 10/2020 | Masuda et al. |
| 10,975,064 B2 | 4/2021 | Taylor et al. |
| 10,988,459 B2 | 4/2021 | Patel et al. |
| 11,407,736 B2 | 8/2022 | Chen et al. |
| 2015/0353533 A1 | 12/2015 | Bandyopadhyay et al. |
| 2017/0226127 A1 | 8/2017 | Estrada et al. |
| 2019/0337907 A1 | 11/2019 | Masuda et al. |
| 2019/0337934 A1 | 11/2019 | Taylor et al. |
| 2021/0069208 A1 | 3/2021 | Yu et al. |
| 2021/0070735 A1 | 3/2021 | Bhamidipati et al. |
| 2021/0070743 A1 | 3/2021 | Shaw et al. |
| 2021/0070744 A1 | 3/2021 | Chen et al. |
| 2021/0139494 A1 | 5/2021 | Chen et al. |
| 2021/0292340 A1 | 9/2021 | Ma et al. |
| 2021/0317135 A1 | 10/2021 | Darwish et al. |

(Continued)

FOREIGN PATENT DOCUMENTS

| | | |
|---|---|---|
| WO | 2016/027253 | 2/2016 |
| WO | 2016/128936 | 8/2016 |
| WO | 2017/064217 | 4/2017 |

(Continued)

OTHER PUBLICATIONS

Harris, Philip A., et al. "DNA-Encoded Library Screening Identifies Benzo[b][1,4]oxazepin-4-ones as Highly Potent and Monoselective Receptor Interacting Protein 1 Kinase Inhibitors," Journal of Medicinal Chemistry, vol. 59, No. 5, Mar. 10, 2016, pp. 2163-2178.

Harris, Philip A., et al. "Identification of a RIP1 Kinase Inhibitor Clinical Candidate (GSK3145095) for the Treatment of Pancreatic Cancer," ACS Medicinal Chemistry Letters, vol. 10, No. 6, May 9, 2019, pp. 857-862.

Yoshikawa, Masato, et al., "Discovery of 7-Oxo-2,4,5,7-tetrahydro-6H-pyrazolo[3,4-c]pyridine Derivatives as Potent, Orally Available, and Brain-Penetrating Receptor Interacting Protein 1 (RIP1) Kinase Inhibitors: Analysis of Structure-Kinetic Relationship," Journal of Medicinal Chemistry, vol. 61, No. 6, Feb. 22, 2018, pp. 2384-2409.

(Continued)

*Primary Examiner* — Brenda L Coleman

(57) ABSTRACT

Disclosed herein are kinase inhibitory compounds, such as a receptor-interacting protein-1 (RIP1) kinase inhibitor compounds, as well as pharmaceutical compositions and combinations comprising such inhibitory compounds. The disclosed compounds, pharmaceutical compositions, and/or combinations may be used to treat or prevent a kinase-associated disease or condition, particularly a RIP1-associated disease or condition.

4 Claims, No Drawings

(56) References Cited

U.S. PATENT DOCUMENTS

2021/0371430 A1 12/2021 Zhou et al.
2022/0009936 A1 1/2022 Bhamidipati et al.

FOREIGN PATENT DOCUMENTS

| WO | 2017/069279 | 4/2017 |
| WO | 2017/109724 | 6/2017 |
| WO | 2018/073193 | 4/2018 |
| WO | 2018/109097 | 6/2018 |
| WO | 2018/154520 | 8/2018 |
| WO | 2020/001420 | 1/2020 |
| WO | 2020/088194 | 5/2020 |

OTHER PUBLICATIONS

Harris et al., "Discovery and Lead-Optimization of 4,5-Dihydropyrazoles as Mono-Kinase Selective, Orally Bioavailable and Efficacious Inhibitors of Receptor Interacting Protein 1 (RIP1) Kinase," Journal of Medicinal Chemistry, pp. 5096-5110, vol. 62, No. 10, (2019).

Harris et al., "Discovery of a First-in-Class Receptor Interacting Protein 1 (RIP1) Kinase Specific Clinical Candidate (GSK2982772) for the Treatment of Inflammatory Diseases" Journal of Medicinal Chemistry 60:1247-1261, 2017.

Ishii et al., "CETSA quantitatively verifies in vivo target engagement of novel RIPK1 inhibitors in various biospecimens" Scientific Reports 7(1): 13000, pp. 1-14, 2017.

Najjar et al., "Structure guided design of potent and selective ponatinib-based hybrid inhibitors for RIPK1" Cell Reports 12(11): 1850-1860, Mar. 24, 2015.

RIP1K INHIBITORS

The present disclosure concerns compounds and methods of making and using the compounds, such as for inhibiting receptor-interacting protein-1 kinase ("RIP1"), and for treating diseases and/or conditions related to RIP1.

Receptor-interacting protein-1 kinase (referred to herein as "RIP1") belongs to the tyrosine kinase-like family and is a serine/threonine protein kinase involved in innate immune signaling. RIP1 plays a central role in regulating cell signaling and its role in programmed cell death has been linked to various inflammatory diseases, such as inflammatory bowel disease, psoriasis, and other diseases and/or conditions associated with inflammation and/or necroptotic cell death.

Disclosed herein are compounds according to the formula

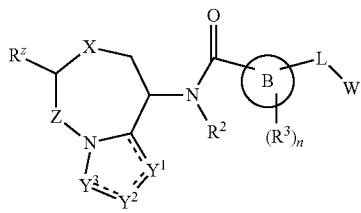

wherein
X is selected from $CH_2$, O, S, S(O), $S(O)_2$ and $NR^a$;
$R^a$ is for each occurrence selected from hydrogen, $C_{1-6}$alkyl and $C_{1-6}$acyl;
$Y^1$, $Y^2$ and $Y^3$ are independently selected from the group consisting of N, $N(R^a)$, O, $C(R^b)_{1-2}$ and C=O;
$R^b$ is selected from hydrogen, $C_{1-6}$alkyl and halo;
Z is $C(R^c)$ or $NR^c$;
$R^c$ is a $C_{1-4}$ unsaturated carbon chain optionally substituted with one or more $R^1$ groups, optionally interrupted by 1 or 2 heteroatoms selected from O, N and S;
$R^z$ is N, CH or $C(R^1)$ and together with $ZR^c$ and the carbon to which they are bound form a 5 or 6 membered heteroaryl or 6-membered aryl ring optionally substituted with m $R^1$ groups;
$R^1$ is a halogen, a linker-$R^6$ group, wherein the linker is a bond, (C1-C4) alkanyl, (C1-C4) alkenyl or (C1-C4) alkynyl, optionally substituted by one or more $R^b$ and $R^6$ is $R^e$, —$C(R^f)_3$, or —$C(R^f)$=$C(R^f)_2$;
$R^2$ is $R^a$;
ring B is 5-10-membered heteroaryl;
$R^3$ is, for each occurrence, independently selected from $R^b$ and $OR^a$;
L is O, $NR^a$ or alkylene;
W is 5-10 membered aryl or heteroaryl optionally substituted by p $R^4$;
$R^4$ is for each occurrence selected from $R^b$ and $OR^a$;
$R^d$ is for each occurrence independently selected from hydrogen, $C_{1-6}$alkyl, aralkyl, $C_{5-10}$ aryl or heteroaryl, or two $R^d$ together with a nitrogen to which they are both attached form a $C_{3-10}$heterocyclic group optionally substituted by one or more $R^e$;
$R^e$ is independently for each occurrence halo, —$OR^d$, —$SR^d$, —$S(O)_2R^d$, —$NR^dR^d$, —$Si(R^a)_3$, —C(O)OH, —$C(O)OR^a$, or —$C(O)NR^dR^d$;
$R^f$ is independently for each occurrence $R^a$, $R^b$, or $R^e$, or two $R^f$ groups together with the carbon atom bound thereto provide a $C_{3-6}$cycloalkyl group or a $C_{3-10}$heterocyclic group each optionally substituted with one or more $R^e$;

m is 1, 2, 3, or 4;
n is 0, 1 or 2; and
p is 0, 1, 2, 3, 4, or 5.

In addition, methods and intermediates for making the compounds are disclosed along with pharmaceutical formulations and methods for using the compounds and formulations. The foregoing and other objects, features, and advantages of the invention will become more apparent from the following detailed description.

I. OVERVIEW OF TERMS

The following explanations of terms and methods are provided to better describe the present disclosure and to guide those of ordinary skill in the art in the practice of the present disclosure. The singular forms "a," "an," and "the" refer to one or more than one, unless the context clearly dictates otherwise. The term "or" refers to a single element of stated alternative elements or a combination of two or more elements, unless the context clearly indicates otherwise. As used herein, "comprises" means "includes." Thus, "comprising A or B," means "including A, B, or A and B," without excluding additional elements. All references, including patents and patent applications cited herein, are incorporated by reference.

Unless otherwise indicated, all numbers expressing quantities of components, molecular weights, percentages, temperatures, times, and so forth, as used in the specification or claims are to be understood as being modified by the term "about." Accordingly, unless otherwise indicated, implicitly or explicitly, the numerical parameters set forth are approximations that may depend on the desired properties sought and/or limits of detection under standard test conditions/methods. When directly and explicitly distinguishing embodiments from discussed prior art, the embodiment numbers are not approximates unless the word "about" is expressly recited.

Unless explained otherwise, all technical and scientific terms used herein have the same meaning as commonly understood to one of ordinary skill in the art to which this disclosure pertains. Although methods and materials similar or equivalent to those described herein can be used in the practice or testing of the present disclosure, suitable methods and materials are described below. The materials, methods, and examples are illustrative only and not intended to be limiting.

As used herein, the term "substituted" refers to all subsequent modifiers in a term, for example in the term "substituted aryl$C_{1-8}$alkyl," substitution may occur on the "$C_{1-8}$alkyl" portion, the "aryl" portion or both portions of the aryl$C_{1-8}$alkyl group.

"Substituted," when used to modify a specified group or moiety, means that at least one, and perhaps two or more, hydrogen atoms of the specified group or moiety is independently replaced with the same or different substituent groups as defined below. In a particular embodiment, a group, moiety or substituent may be substituted or unsubstituted, unless expressly defined as either "unsubstituted" or "substituted." Accordingly, any of the groups specified herein may be unsubstituted or substituted unless the context indicates otherwise or a particular structural formula precludes substitution. In particular embodiments, a substituent may or may not be expressly defined as substituted, but is still contemplated to be optionally substituted. For example, an "aliphatic" or a "cyclic" moiety may be unsubstituted or substituted, but an "unsubstituted aliphatic" or an "unsubstituted cyclic" is not substituted.

"Substituents" or "substituent groups" for substituting for one or more hydrogen atoms on saturated carbon atoms in the specified group or moiety. As used herein, the term "substituted" refers to all subsequent modifiers in a term, for example in the term "substituted aryl$C_{1-8}$alkyl," substitution may occur on the "$C_{1-8}$alkyl" portion, the "aryl" portion or both portions of the aryl$C_{1-8}$alkyl group.

"Substituted," when used to modify a specified group or moiety, means that at least one, and perhaps two or more, hydrogen atoms of the specified group or moiety is independently replaced with the same or different substituent groups as defined below. In a particular embodiment, a group, moiety or substituent may be substituted or unsubstituted, unless expressly defined as either "unsubstituted" or "substituted." Accordingly, any of the groups specified herein may be unsubstituted or substituted unless the context indicates otherwise or a particular structural formula precludes substitution. In particular embodiments, a substituent may or may not be expressly defined as substituted, but is still contemplated to be optionally substituted. For example, an "aliphatic" or a "cyclic" moiety may be unsubstituted or substituted, but an "unsubstituted aliphatic" or an "unsubstituted cyclic" is not substituted.

"Substituents" or "substituent groups" for substituting for one or more hydrogen atoms on saturated carbon atoms in the specified group or moiety described herein can be, unless otherwise specified, —$R^{60}$, halo, =O, —$OR^{70}$, —$SR^{70}$, —$N(R^{80})_2$, haloalkyl, perhaloalkyl, —CN, —$NO_2$, =$N_2$, —$N_3$, —$SO_2R^{70}$, —$SO_3^-M^+$, —$SO_3R^{70}$, —$OSO_2R^{70}$, —$OSO_3^-M^+$, —$OSO_3R^{70}$, —$P(O)(O^-)_2(M^+)_2$, —$P(O)(O^-)_2M^{2+}$, —$P(O)(OR^{70})O^-M^+$, —$P(O)(OR^{70})_2$, —$C(O)R^{70}$, —$C(S)R^{70}$, —$C(NR^{70})R^{70}$, —$CO_2^-M^+$, —$CO_2R^{70}$, —$C(S)OR^{70}$, —$C(O)N(R^{80})_2$, —$C(NR^{70})(R^{80})_2$, —$OC(O)R^{70}$, —$OC(S)R^{70}$, —$OCO_2^-M^+$, —$OCO_2R^{70}$, —$OC(S)OR^{70}$, —$NR^{70}C(O)R^{70}$, —$NR^{70}C(S)R^{70}$, —$NR^{70}CO_2^-M^+$, —$NR^{70}CO_2R^{70}$, —$NR^{70}C(S)OR^{70}$, —$NR^{70}C(O)N(R^{80})_2$, —$NR^{70}C(NR^{70})R^{70}$ and —$NR^{70}C(NR^{70})N(R^{80})_2$, where $R^{60}$ is $C_{1-10}$aliphatic, heteroaliphatic, or cycloaliphatic, typically, $C_{1-6}$aliphatic, more typically $C_{1-6}$alkyl, where $R^{60}$ optionally may be substituted; each $R^{70}$ is independently for each occurrence hydrogen or $R^{60}$; each $R^{80}$ is independently for each occurrence $R^{70}$ or alternatively, two $R^{80}$ groups, taken together with the nitrogen atom to which they are bonded, form a 3- to 7-membered heterocycloaliphatic, which optionally includes from 1 to 4 of the same or different additional heteroatoms selected from O, N and S, of which N optionally has $R^{70}$ substitution, such as H or $C_1$-$C_3$alkyl substitution; and each $M^+$ is a counter ion with a net single positive charge. Each $M^+$ is independently for each occurrence, for example, an alkali metal ion, such as $K^+$, $Na^+$, $Li^+$; an ammonium ion, such as $^+N(R^{60})_4$; a protonated amino acid ion, such as a lysine ion, or an arginine ion; or an alkaline metal earth ion, such as $[Ca^{2+}]_{0.5}$, $[Mg^{2+}]_{0.5}$, or $[Ba^{2+}]_{0.5}$ (a subscript "0.5" means, for example, that one of the counter ions for such divalent alkali earth ions can be an ionized form of a compound of the disclosure and the other a typical counter ion such as chloride, or two ionized compounds can serve as counter ions for such divalent alkali earth ions, or a doubly ionized compound can serve as the counter ion for such divalent alkali earth ions). As specific examples, —$N(R^{80})_2$ includes —$NH_2$, —NH-alkyl, —NH-pyrrolidin-3-yl, N-pyrrolidinyl, N-piperazinyl, 4N-methyl-piperazin-1-yl, N-morpholinyl and the like. Any two hydrogen atoms on a single carbon also can be replaced with, for example, =O, =$NR^{70}$, =N—$OR^{70}$, =$N_2$ or =S.

Substituent groups for replacing hydrogen atoms on unsaturated carbon atoms in groups containing unsaturated carbons are, unless otherwise specified, —$R^{60}$, halo, —$O^-M^+$, —$OR^{70}$, —$SR^{70}$, —$S^-M^+$, —$N(R^{80})_2$, perhaloalkyl, —CN, —OCN, —SCN, —NO, —$NO_2$, —$N_3$, —$SO_2R^{70}$, —$SO_3^-M^+$, —$SO_3R^{70}$, —$OSO_2R^{70}$, —$OSO_3^-M^+$, —$OSO_3R^{70}$, —$PO_3^{-2}(M^+)_2$, —$PO_3^{-2}M^{2+}$, —$P(O)(OR^{70})O^-M^+$, —$P(O)(OR^{70})_2$, —$C(O)R^{70}$, —$C(S)R^{70}$, —$C(NR^{70})R^{70}$, —$CO_2^-M^+$, —$CO_2R^{70}$, —$C(S)OR^{70}$, —$C(O)NR^{80}R^{80}$, —$C(NR^{70})N(R^{80})_2$, —$OC(O)R^{70}$, —$OC(S)R^{70}$, —$OCO_2^-M^+$, —$OCO_2R^{70}$, —$OC(S)OR^{70}$, —$NR^{70}C(O)R^{70}$, —$NR^{70}C(S)R^{70}$, —$NR^{70}CO_2^-M^+$, —$NR^{70}CO_2R^{70}$, —$NR^{70}C(S)OR^{70}$, —$NR^{70}C(O)N(R^{80})_2$, —$NR^{70}C(NR^{70})R^{70}$ and —$NR^{70}C(NR^{70})N(R^{80})_2$, where $R^{60}$, $R^{70}$, $R^{80}$ and $M^+$ are as previously defined. In an independent embodiment, the substituents are not —$O^-M^+$, —$OR^{70}$, —$SR^{70}$, or —$S^-M^+$.

Substituent groups for replacing hydrogen atoms on nitrogen atoms in groups containing such nitrogen atoms are, unless otherwise specified, —$R^{60}$, —$O^-M^+$, —$OR^{70}$, —$SR^{70}$, —$S^-M^+$, —$N(R^{80})_2$, perhaloalkyl, —CN, —NO, —$NO_2$, —$S(O)_2R^{70}$, —$SO_3^-M^+$, —$SO_3R^{70}$, —$OS(O)_2R^{70}$, —$OSO_3^-M^+$, —$OSO_3R^{70}$, —$PO_3^{2-}(M^+)_2$, —$PO_3^{2-}M^{2+}$, —$P(O)(OR^{70})O^-M^+$, —$P(O)(OR^{70})(OR^{70})$, —$C(O)R^{70}$, —$C(S)R^{70}$, —$C(NR^{70})R^{70}$, —$CO_2R^{70}$, —$C(S)OR^{70}$, —$C(O)NR^{80}R^{80}$, —$C(NR^{70})NR^{80}R^{80}$, —$OC(O)R^{70}$, —$OC(S)R^{70}$, —$OCO_2R^{70}$, —$OC(S)OR^{70}$, —$NR^{70}C(O)R^{70}$, —$NR^{70}C(S)R^{70}$, —$NR^{70}CO_2R^{70}$, —$NR^{70}C(S)OR^{70}$, —$NR^{70}C(O)N(R^{80})_2$, —$NR^{70}C(NR^{70})R^{70}$ and —$NR^{70}C(NR^{70})N(R^{80})_2$, where $R^{60}$, $R^{70}$, $R^{80}$ and $M^+$ are as previously defined.

In one embodiment, a group that is substituted has at least one substituent selected from those described above up to the number of substituents possible for a particular moiety, such as from one to five substituents, one substituent, two substituents, three substituents, four substituents or five substituents.

Additionally, in embodiments where a group or moiety is substituted with a substituted substituent, the nesting of such substituted substituents is limited to three, thereby preventing the formation of polymers. Thus, in a group or moiety comprising a first group that is a substituent on a second group that is itself a substituent on a third group, which is attached to the parent structure, the first (outermost) group can only be substituted with unsubstituted substituents. For example, in a group comprising -(aryl-1)-(aryl-2)-(aryl-3), aryl-3 can only be substituted with substituents that are not themselves substituted.

Any group or moiety defined herein can be connected to any other portion of a disclosed structure, such as a parent or core structure, as would be understood by a person of ordinary skill in the art, such as by considering valence rules, comparison to exemplary species, and/or considering functionality, unless the connectivity of the group or moiety to the other portion of the structure is expressly stated, or is implied by context.

"Aliphatic" refers to a substantially hydrocarbon-based group or moiety. An aliphatic group or moiety can be acyclic, including alkyl, alkenyl, or alkynyl groups (as well as alkylene, alkenylene, or alkynylene groups), cyclic versions thereof, such as cycloaliphatic groups or moieties including cycloalkyl, cycloalkenyl or cycloalkynyl, and further including straight- and branched-chain arrangements, and all stereo and position isomers as well. Unless expressly stated otherwise, an aliphatic group contains from one to twenty-five carbon atoms ($C_{1-25}$); for example, from one to fifteen ($C_{1-15}$), from one to ten ($C_{1-10}$) from one to six ($C_{1-6}$), or from one to four carbon atoms ($C_{1-4}$) for an acyclic aliphatic group or moiety, or from three to fifteen ($C_{3-15}$) from three to ten ($C_{3-10}$), from three to six ($C_{3-6}$), or from three to four ($C_{3-4}$) carbon atoms for a cycloaliphatic group or moiety. An aliphatic group may be substituted or unsubstituted, unless expressly referred to as an "unsubstituted aliphatic" or a "substituted aliphatic." An aliphatic group can be substituted with one or more substituents (up to two substituents for each methylene carbon in an aliphatic chain, or up to one substituent for each carbon of a —C═C— double bond in an aliphatic chain, or up to one substituent for a carbon of a terminal methine group).

"Lower aliphatic" refers to an aliphatic group containing from one to ten carbon atoms ($C_{1-10}$), such as from one to six ($C_{1-6}$), or from one to four ($C_{1-4}$) carbon atoms; or from three to ten ($C_{3-10}$), such as from three to six ($C_{3-6}$) carbon atoms for a lower cycloaliphatic group.

"Alkoxy" refers to the group —OR, where R is a substituted or unsubstituted alkyl or a substituted or unsubstituted cycloalkyl group. In certain examples R is a $C_{1-6}$ alkyl group or a $C_{3-6}$cycloalkyl group. Methoxy (—OCH$_3$) and ethoxy (—OCH$_2$CH$_3$) are exemplary alkoxy groups. In a substituted alkoxy, R is substituted alkyl or substituted cycloalkyl, examples of which in the presently disclosed compounds include haloalkoxy groups, such as —OCF$_2$H.

"Alkoxyalkyl" refers to the group -alkyl-OR, where R is a substituted or unsubstituted alkyl or a substituted or unsubstituted cycloalkyl group; —CH$_2$CH$_2$—O—CH$_2$CH$_3$ is an exemplary alkoxyalkyl group.

"Alkyl" refers to a saturated aliphatic hydrocarbyl group having from 1 to at least ($C_{1-25}$) carbon atoms, more typically 1 to 10 ($C_{1-10}$) carbon atoms such as 1 to 6 ($C_{1-6}$) carbon atoms. An alkyl moiety may be substituted or unsubstituted. This term includes, by way of example, linear and branched hydrocarbyl groups such as methyl (CH$_3$), ethyl (—CH$_2$CH$_3$), n-propyl (—CH$_2$CH$_2$CH$_3$), isopropyl (—CH(CH$_3$)$_2$), n-butyl (—CH$_2$—CH$_2$CH$_2$CH$_3$), isobutyl (—CH$_2$CH$_2$(CH$_3$)$_2$), sec-butyl (—CH(CH$_3$)(CH$_2$CH$_3$), t-butyl (—C(CH$_3$)$_3$), n-pentyl (—CH$_2$CH$_2$CH$_2$CH$_2$CH$_3$), and neopentyl (—CH$_2$C(CH$_3$)$_3$).

"Alkylene" refers to a divalent alkyl group or alkyl chain. As with the alkyl groups described above, such alkylene groups optionally are substituted with one or more substituents as described above. By way of example, such alkylene groups include, without limitation —CH$_2$, —CH(Me), —C(Me)$_2$, —CF$_2$—, —CH(F), —CH$_2$CH$_2$— and the like. As disclosed herein, such alkylene moieties are useful as linking groups.

Similarly, the terms "Alkenylene" and "Alkynylene" refer to divalent aliphatic chains containing at least one alkene or at least one alkyne, respectively. Such alkenylene and alkynylene groups may be substituted with one or more substituent described above.

"Amino" refers to the group —NH$_2$, —NHR, or —NRR, where each R independently is selected from H, aliphatic, heteroaliphatic, aromatic, including both aryl and heteroaryl, or heterocycloaliphatic, or two R groups together with the nitrogen attached thereto form a heterocyclic ring. Examples of such heterocyclic rings include those wherein two R groups together with the nitrogen to which they are attached form a —(CH$_2$)$_{2-5}$— ring optionally interrupted by one or two heteroatom groups, such as —O— or —N(R$^g$) such as in the groups

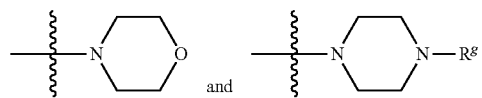

wherein R$^g$ is R$^{70}$, —C(O)R$^{70}$, —C(O)OR$^{60}$ or —C(O)N(R$^{80}$)$_2$.

"Amide" refers to the group —N(R)acyl, wherein R is hydrogen, heteroaliphatic, or aliphatic, such as alkyl, particularly $C_{1-6}$alkyl.

"Aromatic" refers to a cyclic, conjugated group or moiety of, unless specified otherwise, from 5 to 15 ring atoms having a single ring (e.g., phenyl, pyridinyl, or pyrazolyl) or multiple condensed rings in which at least one ring is aromatic (e.g., naphthyl, indolyl, or pyrazolopyridinyl), that is at least one ring, and optionally multiple condensed rings, have a continuous, delocalized π-electron system. Typically, the number of out of plane π-electrons corresponds to the Hückel rule (4n+2). The point of attachment to the parent structure typically is through an aromatic portion of the condensed ring system. For example,

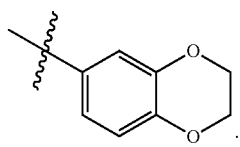 [SMILES: *c1ccc2c(c1)OCCO2]

However, in certain examples, context or express disclosure may indicate that the point of attachment is through a non-aromatic portion of the condensed ring system. For example,

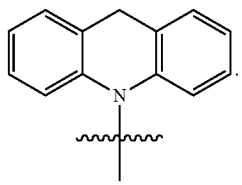 [SMILES: *N1c2ccccc2Cc2ccccc21]

An aromatic group or moiety may comprise only carbon atoms in the ring, such as in an aryl group or moiety, or it may comprise one or more ring carbon atoms and one or more ring heteroatoms comprising a lone pair of electrons (e.g. S, O, N, P, or Si), such as in a heteroaryl group or moiety. Unless otherwise stated, an aromatic group may be substituted or unsubstituted.

"Aryl" refers to an aromatic carbocyclic group of, unless specified otherwise, from 6 to 15 carbon atoms having a single ring (e.g., phenyl) or multiple condensed rings in which at least one ring is aromatic (e.g., 1,2,3,4-tetrahydroquinoline, benzodioxole, and the like). If any aromatic ring portion contains a heteroatom, the group is heteroaryl and not aryl. Aryl groups may be, for example, monocyclic, bicyclic, tricyclic or tetracyclic. Unless otherwise stated, an aryl group may be substituted or unsubstituted.

"Araliphatic" refers to an aryl group attached to the parent via an aliphatic moiety. Araliphatic includes aralkyl or arylalkyl groups such as benzyl and phenylethyl.

"Carboxyl" refers to —CO$_2$H.

"Carboxamide" refers to —C(O)amino.

"Carboxyl ester" or "carboxy ester" refers to the group —C(O)OR, where R is aliphatic, heteroaliphatic, or aromatic (including both aryl and heteroaryl).

"Carboxylate" refers to —C(O)O— or salts thereof.

"Cyano" refers to the group —CN.

"Cycloaliphatic" refers to a cyclic aliphatic group having a single ring (e.g., cyclohexyl), or multiple rings, such as in a fused, bridged or spirocyclic system, the ring or at least one of the rings in the system is aliphatic. Typically, the point of attachment to the parent structure is through an aliphatic portion of the multiple ring system. Cycloaliphatic includes saturated and unsaturated systems, including cycloalkyl, cycloalkenyl and cycloalkynyl. A cycloaliphatic group may contain from three to twenty-five carbon atoms; for example, from three to fifteen, from three to ten, or from three to six carbon atoms. Unless otherwise stated, a cycloaliphatic group may be substituted or unsubstituted. Exemplary cycloaliphatic groups include, but are not limited to, cyclopropyl, cyclobutyl, cyclopentyl, cyclohexyl, cycloheptyl, cyclopentenyl, or cyclohexenyl.

"Halo," "halide" or "halogen" refers to fluoro, chloro, bromo or iodo.

"Haloalkyl" refers to an alkyl moiety substituted with one or more halogens. Exemplary haloalkyl moieties include —CH$_2$F, —CHF$_2$ and —CF$_3$.

"Heteroaliphatic" refers to an aliphatic compound or group having at least one heteroatom and at least one carbon atom, i.e., at least one carbon atom from an aliphatic compound or group comprising at least two carbon atoms, has been replaced with an atom having at least one lone pair of electrons, typically nitrogen, oxygen, phosphorus, silicon, or sulfur. Heteroaliphatic compounds or groups may be substituted or unsubstituted, branched or unbranched, chiral or achiral, and/or acyclic or cyclic, such as a heterocycloaliphatic group.

"Heteroaryl" refers to an aromatic group or moiety having, unless specified otherwise, from 5 to 15 ring atoms comprising at least one carbon atom and at least one heteroatom, such as N, S, O, P, or Si. A heteroaryl group or moiety may comprise a single ring (e.g., pyridinyl, pyrimidinyl or pyrazolyl) or multiple condensed rings (e.g., indolyl, benzopyrazolyl, or pyrazolopyridinyl). Heteroaryl groups or moiety may be, for example, monocyclic, bicyclic, tricyclic or tetracyclic. Unless otherwise stated, a heteroaryl group or moiety may be substituted or unsubstituted.

"Heterocyclyl," "heterocyclo" and "heterocycle" refer to both aromatic and non-aromatic ring systems, and more specifically refer to a stable three- to fifteen-membered ring moiety comprising at least one carbon atom, and typically plural carbon atoms, and at least one, such as from one to five, heteroatoms. The heteroatom(s) may be nitrogen, phosphorus, oxygen, silicon or sulfur atom(s). The heterocyclyl moiety may be a monocyclic moiety, or may comprise multiple rings, such as in a bicyclic or tricyclic ring system, provided that at least one of the rings contains a heteroatom. Such a multiple ring moiety can include fused or bridged ring systems as well as spirocyclic systems; and any nitrogen, phosphorus, carbon, silicon or sulfur atoms in the heterocyclyl moiety can be optionally oxidized to various oxidation states. For convenience, nitrogens, particularly, but not exclusively, those defined as annular aromatic nitrogens, are meant to include their corresponding N-oxide form, although not explicitly defined as such in a particular example. Thus, for a compound having, for example, a pyridinyl ring, the corresponding pyridinyl-N-oxide is included as another compound of the disclosure, unless expressly excluded or excluded by context. In addition, annular nitrogen atoms can be optionally quaternized. Heterocycle includes heteroaryl moieties, and heteroalicyclyl or heterocycloaliphatic moieties, which are heterocyclyl rings that are partially or fully saturated. Examples of heterocyclyl groups include, but are not limited to, azetidinyl, oxetanyl, acridinyl, benzodioxolyl, benzodioxanyl, benzofuranyl, carbazoyl, cinnolinyl, dioxolanyl, indolizinyl, naphthyridinyl, perhydroazepinyl, phenazinyl, phenothiazinyl, phenoxazinyl, phthalazinyl, pteridinyl, purinyl, quinazolinyl, quinoxalinyl, quinolinyl, isoquinolinyl, tetrazoyl, tetrahydroisoquinolyl, piperidinyl, piperazinyl, 2-oxopiperazinyl, 2-oxopiperidinyl, 2-oxopyrrolidinyl, 2-oxoazepinyl, azepinyl, pyrrolyl, 4-piperidonyl, pyrrolidinyl, pyrazolyl, pyrazolidinyl, imidazolyl, imidazolinyl, imidazolidinyl, dihydropyridinyl, tetrahydropyridinyl, pyridinyl, pyrazinyl, pyrimidinyl, pyridazinyl, oxazolyl, oxazolinyl, oxazolidinyl, triazolyl, isoxazolyl, isoxazolidinyl, morpholinyl, thiazolyl, thiazolinyl, thiazolidinyl, isothiazolyl, quinuclidinyl, isothiazolidinyl, indolyl, isoindolyl, indolinyl, isoindolinyl, octahydroindolyl, octahydroisoindolyl, quinolyl, isoquinolyl, decahydroisoquinolyl, benzimidazolyl, thiadiazolyl, benzopyranyl, benzothiazolyl, benzoxazolyl, furyl, diazabicycloheptane, diazapane, diazepine, tetrahydrofuryl, tetrahydropyranyl, thienyl, benzothieliyl, thiamorpholinyl, thiamorpholinyl sulfoxide, thiamorpholinyl sulfone, dioxaphospholanyl, and oxadiazolyl.

"Hydroxyl" refers to the group —OH.

"Nitro" refers to the group —NO$_2$.

"Phosphate" refers to the group —O—P(O)(OR')$_2$, where each —OR' independently is —OH; —O-aliphatic, such as —O-alkyl or —O-cycloalkyl; —O-aromatic, including both —O-aryl and —O-heteroaryl; —O-aralkyl; or —OR' is —O$^-$M$^+$, where M$^+$ is a counter ion with a single positive charge. Each M$^+$ may be an alkali ion, such as K$^+$, Na$^+$, Li$^+$; an ammonium ion, such as $^+$N(R")$_4$ where R" is H, aliphatic, heteroaliphatic, or aromatic (including both aryl and heteroaryl); or an alkaline earth ion, such as [Ca$^{2+}$]$_{0.5}$, [Mg$^{2+}$]$_{0.5}$, or [Ba$^{2+}$]$_{0.5}$. Phosphonooxyalkyl refers to the group -alkyl-phosphate, such as, for example, —CH$_2$OP(O)(OH)$_2$, or a salt thereof, such as —CH$_2$OP(O)(O$^-$Na$^+$)$_2$, and (((dialkoxyphosphoryl)oxy)alkyl) refers to the dialkyl ester of a phosphonooxyalkyl group, such as, for example, —CH$_2$OP(O)(O-tert-butyl)$_2$.

"Phosphonate" refers to the group —P(O)(OR')$_2$, where each —OR' independently is —OH; —O-aliphatic such as —O-alkyl or —O-cycloalkyl; —O-aromatic, including both —O-aryl and —O-heteroaryl; or —O-aralkyl; or —OR' is —O$^-$M$^+$, and M$^+$ is a counter ion with a single positive charge. Each M$^+$ is a positively charged counterion and may be, by way of example, an alkali metal ion, such as K$^+$, Na$^+$, Li$^+$; an ammonium ion, such as $^+$N(R")$_4$ where R" is H, aliphatic, heteroaliphatic, or aromatic (including both aryl and heteroaryl); or an alkaline earth metal ion, such as [Ca$^{2+}$]$_{0.5}$, [Mg$^{2+}$]$_{0.5}$, or [Ba$^{2+}$]$_{0.5}$. Phosphonoalkyl refers to the group -alkyl-phosphonate, such as, for example, —CH$_2$P(O)(OH)$_2$, or —CH$_2$P(O)(O$^-$Na$^+$)$_2$, and ((dialkoxyphosphoryl)alkyl) refers to the dialkyl ester of a phosphonoalkyl group, such as, for example, —CH$_2$P(O)(O-tert-butyl)$_2$.

"Patient" or "Subject" may refer generally to any living being, but more typically refers to mammals and other animals, particularly humans. Thus disclosed methods are applicable to both human therapy and veterinary applications.

"Pharmaceutically acceptable excipient" refers to a substance, other than the active ingredient, that is included in a composition comprising the active ingredient. As used herein, an excipient may be incorporated within particles of a pharmaceutical composition, or it may be physically mixed with particles of a pharmaceutical composition. An excipient can be used, for example, to dilute an active agent and/or to modify properties of a pharmaceutical composition. Excipients can include, but are not limited to, anti-adherents, binders, coatings, enteric coatings, disintegrants, flavorings, sweeteners, colorants, lubricants, glidants, sorbents, preservatives, carriers or vehicles. Excipients may be starches and modified starches, cellulose and cellulose derivatives, saccharides and their derivatives such as disaccharides, polysaccharides and sugar alcohols, protein, synthetic polymers, crosslinked polymers, antioxidants, amino acids or preservatives. Exemplary excipients include, but are not limited to, magnesium stearate, stearic acid, vegetable stearin, sucrose, lactose, starches, hydroxypropyl cellulose, hydroxypropyl methylcellulose, xylitol, sorbitol, maltitol, gelatin, polyvinylpyrrolidone (PVP), polyethyleneglycol (PEG), tocopheryl polyethylene glycol 1000 succinate (also known as vitamin E TPGS, or TPGS), carboxy methyl cellulose, dipalmitoyl phosphatidyl choline (DPPC), vitamin A, vitamin E, vitamin C, retinyl palmitate, selenium, cysteine, methionine, citric acid, sodium citrate, methyl paraben, propyl paraben, sugar, silica, talc, magnesium carbonate, sodium starch glycolate, tartrazine, aspartame, benzalkonium chloride, sesame oil, propyl gallate, sodium metabisulphite or lanolin.

An "adjuvant" is a component that modifies the effect of other agents, typically the active ingredient. Adjuvants are often pharmacological and/or immunological agents. An adjuvant may modify the effect of an active ingredient by increasing an immune response. An adjuvant may also act as a stabilizing agent for a formulation. Exemplary adjuvants include, but are not limited to, aluminum hydroxide, alum, aluminum phosphate, killed bacteria, squalene, detergents, cytokines, paraffin oil, and combination adjuvants, such as Freund's complete adjuvant or Freund's incomplete adjuvant.

"Pharmaceutically acceptable carrier" refers to an excipient that is a carrier or vehicle, such as a suspension aid, solubilizing aid, or aerosolization aid. *Remington: The Science and Practice of Pharmacy*, The University of the Sciences in Philadelphia, Editor, Lippincott, Williams, & Wilkins, Philadelphia, PA, 21$^{st}$ Edition (2005), incorporated herein by reference, describes exemplary compositions and formulations suitable for pharmaceutical delivery of one or more therapeutic compositions and additional pharmaceutical agents.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. In some examples, the pharmaceutically acceptable carrier may be sterile to be suitable for administration to a subject (for example, by parenteral, intramuscular, or subcutaneous injection). In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

"Pharmaceutically acceptable salt" refers to pharmaceutically acceptable salts of a compound that are derived from a variety of organic and inorganic counter ions as will be known to a person of ordinary skill in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, tartrate, mesylate, acetate, maleate, oxalate, and the like. "Pharmaceutically acceptable acid addition salts" are a subset of "pharmaceutically acceptable salts" that retain the biological effectiveness of the free bases while formed by acid partners. In particular, the disclosed compounds form salts with a variety of pharmaceutically acceptable acids, including, without limitation, inorganic acids such as hydrochloric acid, hydrobromic acid, sulfuric acid, nitric acid, phosphoric acid, and the like, as well as organic acids such as amino acids, formic acid, acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, benzene sulfonic acid, isethionic acid, methanesulfonic acid, ethanesulfonic acid, p-toluenesulfonic acid, salicylic acid, xinafoic acid and the like. "Pharmaceutically acceptable base addition salts" are a subset of "pharmaceutically acceptable salts" that are derived from inorganic bases such as sodium, potassium, lithium, ammonium, calcium, magnesium, iron, zinc, copper, manganese, aluminum salts and the like. Exemplary salts are the ammonium, potassium, sodium, calcium, and magnesium salts. Salts derived from pharmaceutically acceptable organic bases include, but are not limited to, salts of primary, secondary, and tertiary amines, substituted amines including naturally occurring substituted amines, cyclic amines and basic ion exchange resins, such as isopropylamine, trimethylamine, diethylamine, triethylamine, tripropylamine, tris(hydroxymethyl)aminomethane (Tris), ethanolamine, 2-dimethylaminoethanol, 2-diethylaminoethanol, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins, and the like. Exemplary organic bases are isopropylamine, diethylamine, tris(hydroxymethyl)aminomethane (Tris), ethanolamine, trimethylamine, dicyclohexylamine, choline, and caffeine. (See, for example, S. M. Berge, et al., "Pharmaceutical Salts," J. Pharm. Sci., 1977; 66:1-19 which is incorporated herein by reference.) In particular disclosed embodiments, the compounds may be a formate, trifluoroactate, hydrochloride or sodium salt.

"Effective amount" with respect to a compound or pharmaceutical composition refers to an amount of the compound or pharmaceutical composition sufficient to achieve a particular desired result, such as to inhibit a protein or enzyme. In particular embodiments, an "effective amount" is an amount sufficient to inhibit RIP1; to elicit a desired biological or medical response in a tissue, system, subject or patient; to treat a specified disorder or disease; to ameliorate or eradicate one or more of its symptoms; and/or to prevent the occurrence of the disease or disorder. The amount of a compound which constitutes an "effective amount" may vary depending on the compound, the desired result, the disease state and its severity, the size, age, and gender of the patient to be treated and the like, as will be understood by a person of ordinary skill in the art.

"Prodrug" refers to compounds that are transformed in vivo to yield a biologically active compound, or a compound more biologically active than the parent compound. In vivo transformation may occur, for example, by hydrolysis or enzymatic conversion. Common examples of prodrug moieties include, but are not limited to, ester and amide forms of a compound having an active form bearing a carboxylic acid moiety. Examples of pharmaceutically acceptable esters of the compounds of this disclosure include, but are not limited to, esters of phosphate groups and carboxylic acids, such as aliphatic esters, particularly alkyl esters (for example $C_{1-6}$alkyl esters). Other prodrug moieties include phosphate esters, such as —CH$_2$—O—P(O)(OR')$_2$ or a salt thereof, wherein R' is H or $C_{1-6}$alkyl. Acceptable esters also include cycloalkyl esters and arylalkyl esters such as, but not limited to benzyl. Examples of pharmaceutically acceptable amides of the compounds of this disclosure include, but are not limited to, primary amides, and secondary and tertiary alkyl amides (for example with between about one and about six carbons). Amides and esters of disclosed exemplary embodiments of compounds according to the present disclosure can be prepared according to conventional methods. A thorough discussion of prodrugs is provided in T. Higuchi and V. Stella, "Pro-drugs as Novel Delivery Systems," Vol 14 of the A.C.S. Symposium Series, and in Bioreversible Carriers in Drug Design, ed. Edward B. Roche, American Pharmaceutical Association and Pergamon Press, 1987, both of which are incorporated herein by reference for all purposes.

"Solvate" refers to a complex formed by combination of solvent molecules with molecules or ions of a solute. The solvent can be an organic solvent, an inorganic solvent, or a mixture of both. Exemplary solvents include, but are not limited to, alcohols, such as methanol, ethanol, propanol; amides such as N,N-dialiphatic amides, such as N,N-dimethylformamide; tetrahydrofuran; alkylsulfoxides, such as dimethylsulfoxide; water; and combinations thereof. The compounds described herein can exist in un-solvated as well as solvated forms when combined with solvents, pharmaceutically acceptable or not, such as water, ethanol, and the like. Solvated forms of the presently disclosed compounds are within the scope of the embodiments disclosed herein.

"Sulfonamide" refers to the group or moiety —SO$_2$amino, or —N(R)sulfonyl, where R is H, aliphatic, heteroaliphatic, or aromatic (including both aryl and heteroaryl).

"Sulfanyl" refers to the group or —SH, —S-aliphatic, —S-heteroaliphatic, —S-aromatic, (including both-S-aryl and —S-heteroaryl).

"Sulfinyl" refers to the group or moiety —S(O)H, —S(O)aliphatic, —S(O)heteroaliphatic, or —S(O)aromatic (including both —S(O)aryl and —S(O)heteroaryl).

"Sulfonyl" refers to the group: —SO$_2$H, —SO$_2$aliphatic, —SO$_2$heteroaliphatic, —SO$_2$aromatic (including both —SO$_2$aryl and —SO$_2$heteroaryl).

"Treating" or "treatment" as used herein concerns treatment of a disease or condition of interest in a patient or subject, particularly a human having the disease or condition of interest, and includes by way of example, and without limitation:
  (i) preventing the disease or condition from occurring in a patient or subject, in particular, when such patient or subject is predisposed to the condition but has not yet been diagnosed as having it;
  (ii) inhibiting the disease or condition, for example, arresting or slowing its development;
  (iii) relieving the disease or condition, for example, causing diminution of a symptom or regression of the disease or condition or a symptom thereof, or
  (iv) stabilizing the disease or condition.

As used herein, the terms "disease" and "condition" can be used interchangeably or can be different in that the particular malady or condition may not have a known causative agent (so that etiology has not yet been determined) and it is therefore not yet recognized as a disease but only as an undesirable condition or syndrome, where a more or less specific set of symptoms have been identified by clinicians.

The above definitions and the following general formulas are not intended to include impermissible substitution patterns (e.g., methyl substituted with 5 fluoro groups). Such impermissible substitution patterns are easily recognized by a person having ordinary skill in the art.

A person of ordinary skill in the art will appreciate that particular compounds may exhibit the phenomena of tautomerism, conformational isomerism, geometric isomerism, and/or optical isomerism. For example, certain disclosed compounds can include one or more chiral centers and/or double bonds and as a consequence can exist as stereoisomers, such as double-bond isomers (i.e., geometric isomers), enantiomers, diasteromers, and mixtures thereof, such as racemic mixtures. As another example, certain disclosed compounds can exist in several tautomeric forms, including the enol form, the keto form, and mixtures thereof. As the various compound names, formulae and compound drawings within the specification and claims can represent only one of the possible tautomeric, conformational isomeric, optical isomeric, or geometric isomeric forms, a person of ordinary skill in the art will appreciate that the disclosed compounds encompass any tautomeric, conformational isomeric, optical isomeric, and/or geometric isomeric forms of the compounds described herein, as well as mixtures of these various different isomeric forms. Mixtures of different isomeric forms, including mixtures of enantiomers and/or stereoisomers, can be separated to provide each separate enantiomer and/or stereoisomer using techniques known to those of ordinary skill in the art, particularly with the benefit of the present disclosure which provides methods such as chiral HPLC for separating such mixtures. Alternatively, compounds may be synthesized in enantio-pure or enantioenriched form as known to those of ordinary skill in the art of organic synthesis. In cases of limited rotation, e.g. around the amide bond or between two directly attached rings such as pyridinyl rings, biphenyl groups, and the like, atropisomers are also possible and are also specifically included in the compounds of the disclosure.

In any embodiments, any or all hydrogens present in the compound, or in a particular group or moiety within the compound, may be replaced by a deuterium or a tritium. Thus, a recitation of alkyl includes deuterated alkyl, wherein the group is enriched in deuterium relative to its natural abundance, or where from one to the maximum number of hydrogens present may be replaced by deuterium. For example, ethyl refers to both $C_2H_5$ or $C_2H_5$ where from 1 to 5 hydrogens are replaced by deuterium, such as in $C_2D_xH_{5-x}$.

II. RIP1-ACTIVE COMPOUNDS AND PHARMACEUTICAL COMPOSITIONS COMPRISING RIP1-ACTIVE COMPOUNDS

A. Compounds

Disclosed herein are compounds and pharmaceutical compositions comprising such compounds that are useful for inhibiting RIP1 and/or for treating diseases and/or conditions associated with RIP1. In some embodiments, the compounds are selective kinase inhibitors. For example, exemplary compounds are able to selectively inhibit RIP1 over other kinases, including over RIP2, RIP3, or both.

In some embodiments, a compound of the present disclosure has a structure according to Formula I

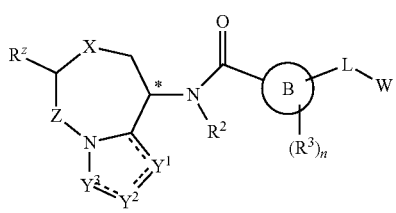

Formula I wherein
X is selected from a bond, $CH_2$, O, S, S(O), $S(O)_2$ and $NR^a$;
$R^a$ is for each occurrence selected from hydrogen and $C_{1-6}$alkyl;
$Y^1$, $Y^2$ and $Y^3$ are independently selected from the group consisting of N, $N(R^a)$, O, $C(R^b)_{1-2}$ and C=O;
$R^b$ is selected from hydrogen, $C_{1-6}$alkyl and halo;
Z is $C(R^c)$ or $NR^c$;
$R^c$ is a $C_{1-4}$ unsaturated carbon chain optionally substituted with one or more $R^1$ groups, optionally interrupted by 1 or 2 heteroatoms selected from O, N and S;
$R^z$ is N, CH or $C(R^1)$ and together with $ZR^c$ and the carbon to which they are bound form a 5 or 6 membered heteroaryl or 6-membered aryl ring optionally substituted with m $R^1$ groups;
$R^1$ is a halogen, a linker-$R^6$ group, wherein the linker is a bond, (C1-C4) alkanyl, (C1-C4) alkenyl or (C1-C4) alkynyl, optionally substituted by one or more $R^b$ and $R^6$ is $R^e$, $—C(R^f)_3$, or $—C(R^f)=C(R^f)_2$;
$R^2$ is $R^a$;
ring B is 5-10-membered heteroaryl;
$R^3$ is, for each occurrence, independently selected from $R^b$ and $OR^a$;
L is O, $NR^a$ or alkylene;
W is 5-10 membered aryl or heteroaryl optionally substituted by p $R^4$;
$R^4$ is for each occurrence selected from $R^b$ and $OR^a$;
$R^d$ is for each occurrence independently selected from hydrogen, $C_{1-6}$alkyl, aralkyl, $C_{5-10}$ aryl or heteroaryl, or two $R^d$ together with a nitrogen to which they are both attached form a $C_{3-10}$heterocyclic group optionally substituted by one or more $R^e$;
$R^e$ is independently for each occurrence halo, $—OR^d$, $—SR^d$, $—S(O)_2R^d$, $—NR^dR^d$, $—Si(R^a)_3$, $—C(O)OH$, $—C(O)OR^a$, or $—C(O)NR^dR^d$;
$R^f$ is independently for each occurrence $R^a$, $R^b$, or $R^e$, or two $R^f$ groups together with the carbon atom bound thereto provide a $C_{3-6}$cycloalkyl group or a $C_{3-10}$heterocyclic group each optionally substituted with one or more $R^e$.
m is 1, 2, 3, or 4;
n is 0, 1 or 2; and
p is 0, 1, 2, 3, 4, or 5.

A person of ordinary skill in the art will appreciate that compounds within the scope of Formula I also include stereoisomers, N-oxides, tautomers, hydrates, solvates, isotopes, and/or prodrugs thereof, unless otherwise specified. With reference to Formula 1, exemplary compounds are isolated as a racemic mixture and other compounds are synthesized and/or isolated as a single enantiomer. In particular the carbon marked with * in Formula I may be in the R or S configuration.

Certain embodiments of Formula I have structures IA, IB, IC or ID

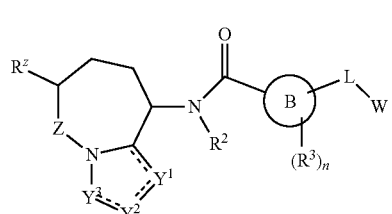

Formula IA

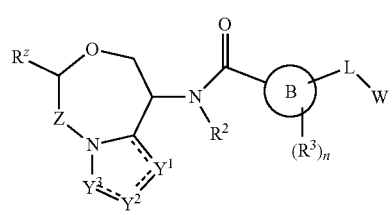

Formula IB

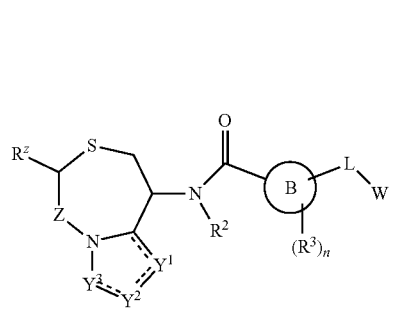

Formula IC

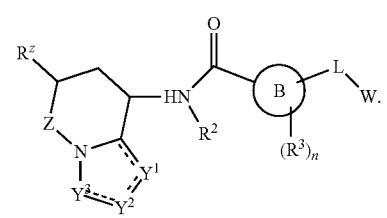

Formula ID

With reference to Formulas I, IA, IB, IC and ID, $R^z$ together with $ZR^c$ and the carbon to which they are bound form a 5 or 6 membered heteroaryl or 6-membered aryl ring optionally substituted with m $R^1$ groups, wherein m is 1, 2, 3 or 4. $R^c$ is a $C_{1-4}$ unsaturated carbon chain optionally interrupted by 1 or 2 heteroatoms selected from O, N and S. Thus, with continued reference to Formulas I, IA, IB and IC certain embodiments of the disclosed compounds have Formula II, III or IV.

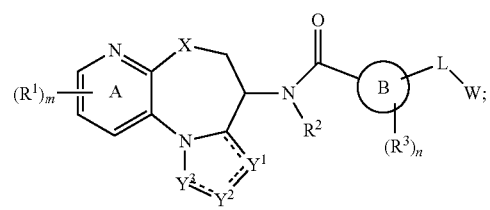

Formula II

-continued

Formula III

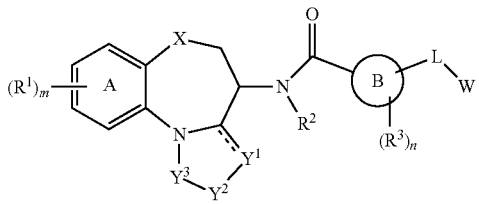

Formula IV

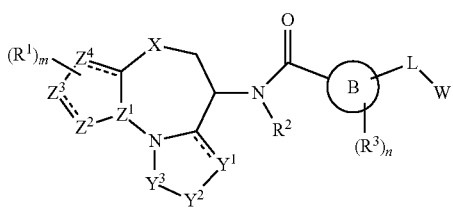

With reference to Formulas I, IA, IB, IC, ID, II, III and IV, m is 0, 1, 2, 3, or 4, such as 1, 2, 3 or 4 and in certain instances m is 1 or 2, such as 1. In other embodiments, m is 0 or 1. In particular in embodiments of Formulas I, IA, IB, IC, ID, II, III and IV wherein B is

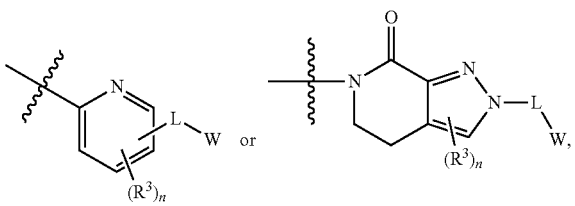

m is 0, 1, 2, 3 or 4, such as 0 or 1.

With reference to Formula IV $Z^1$ is selected from C and N; and $Z^2$, $Z^3$ and $Z^4$ independently are selected from O, S, $S(O)_2$, CH, N, $N(R^a)$ and $CR^1$. With continued reference to Formula IV, m is 0, 1, 2 or 3 and in certain embodiments of Formula IV, m is 0 or 1. In one embodiment of Formula IV at least one of $Z^2$ and $Z^4$ is CH or $CR^1$ and has Formula IVA Formula IVA

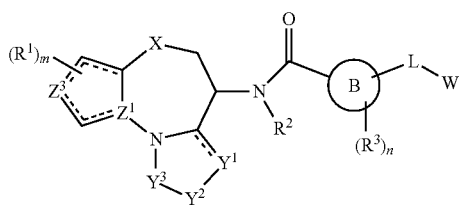

in one embodiment of Formulas IV and IVA, $Z^1$ is N and $Z^3$ is CH or $CR^1$. Such compounds have Formula IVB Formula IVB

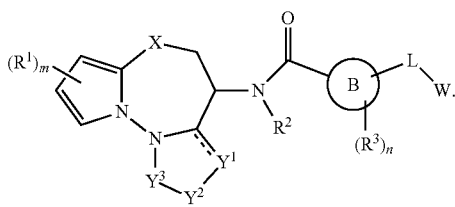

In embodiments of the disclosed RIP1K inhibitor compounds, including those of Formulas I, IA, IB, IC, ID, II and III, IV, IVA and IVB as well as in Formulas V, VA, VB, VC, VD and VI described below, $R^1$ can be, in each instance, linker-$R^6$. In such embodiments, the linker of the linker-$R^6$ moiety is a $C_1$, $C_2$, $C_3$, or $C_4$ aliphatic group, such as a $C_2$ alkylene group, an alkenylene group, or an alkynylene group, or a $C_1$, $C_2$, $C_3$, or $C_4$ haloaliphatic group, such as a $C_2$ haloalkylene group, or an haloalkenylene group. In some embodiments, the linker group of $R^1$ is $R^a$ wherein $R^a$ is $C_1$-$C_4$alkylene, such as —$CH_2$—, —$CH_2CH_2$—, —$CH_2CH_2CH_2$—, or —$CH_2CH_2CH_2CH_2$—; or the linker group is $C_2$-$C_4$alkenylene, such as —CH═CH—, —CH═CHCH$_2$—, —CH$_2$CH═CH—, or —CH$_2$CH═CHCH$_2$—; or the linker group is $C_2$-$C_4$alkynylene, such as —C≡C—, —C≡CCH$_2$—, —CH$_2$C≡C—, or —CHC≡C—CH$_2$—. Such groups optionally are substituted, such as with one or more $R^b$, wherein $R^b$ is selected from $C_{1-6}$alkyl and halo. In some embodiments, the linker group is $C_2$-$C_4$haloalkenylene, such as —CF═CH—, —CCl═CH—, —CH═CCl—, —CH═CF—, —CCl═CCl—, —CF═CF—, or —CCl═CF—, —CF═CCl—. In some embodiments, linker group is —CH$_2$—CH$_2$CH$_2$—, —CH$_2$CH$_2$CH$_2$—, —CH$_2$CH$_2$CH$_2$CH$_2$—, —CH═CH—, —CCl═CH—, —CH═CCl—, or —C ≡C—.

The $R^6$ group of $R^1$ is $C(R^f)_3$ in some embodiments, wherein one $R^f$ is $R^e$, wherein $R^e$ is —$OR^a$ (e.g., hydroxyl or OMe) and each other $R^f$ independently is $R^a$, wherein $R^a$ is $C_{1-4}$aliphatic and preferably each other $R^f$ is $R^a$ wherein $R^a$ is independently for each occurrence $C_{1-4}$alkyl. In particular embodiments, each other $R^f$ is $R^a$ wherein $R^a$ is methyl or $CD_3$. In additional embodiments, $R^6$ is —$C(R^f)_3$ wherein each $R^f$ is $R^a$ wherein $R^a$ is methyl or H or wherein each $R^f$ is $R^a$ wherein $R^a$ is methyl or $R^b$ wherein $R^b$ is —$C(O)OR^c$. In some additional embodiments, one $R^f$ is $R^e$ is —OR' (e.g., hydroxyl or OMe) and the other two $R^f$ groups join together to provide a alicyclic (e.g., cyclopropyl, cyclobutyl, cyclopentyl, or cyclohexyl) or heterocyclic group (e.g., epoxide, oxetane, tetrahydrofuran, tetrahydropyran, piperidinyl, piperazinyl, hexahydrofuro[3,2-b]furan), or the like, with the carbon atom to which they are bound. In some such embodiments, the alicyclic and/or heterocyclic group can be substituted, with some particular embodiments being substituted with one or more hydroxyl groups or benzyl-carbonyl groups.

Some compound embodiments have a linker group that is a $C_{2-4}$ group, which can comprise an alkyne. In particular embodiments, $R^1$ is a -linker-$R^6$ group and the linker is $R^a$ wherein $R^a$ is —$CH_2$—, —$CH_2CH_2$—, —$CH_2CH_2CH_2$—, —$CH_2CH_2CH_2CH_2$—, —CH═CH—, or —C ≡C—, or —$CH_2C≡C$—, and $R^6$ is $R^b$ wherein $R^b$ is —C(O)OEt or is —C(O)NR$^d$R$^d$ or —NR$^d$R$^d$ wherein each R$^d$ independently for each occurrence is hydrogen, C$_{5-10}$heteroaryl, C$_{3-6}$cycloalkyl, or both R$^d$ groups join together to provide a heterocyclic group with the nitrogen atom to which they are bound, which may further comprise one or more additional heteroatoms aside from the nitrogen atom to which the R$^d$ groups are bound. In some embodiments, one R$^d$ is hydrogen and the other R$^d$ is C$_{5-10}$heteroaryl, which can be substituted with one or more R$^e$, such as one of the following:

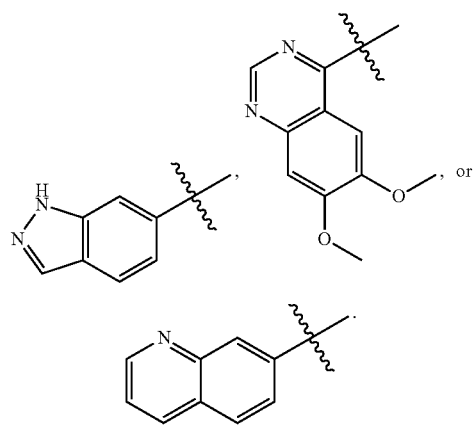 [SMILES: *c1ccc2cn[nH]c2c1 ; *c1ncnc2cc(OC)c(OC)cc12 ; *c1ccc2cccnc2c1]

In particular embodiments of Formulas I, IA, IB, IC, ID, II and III, IV, IVA and IVB at least one R$^1$ moiety is

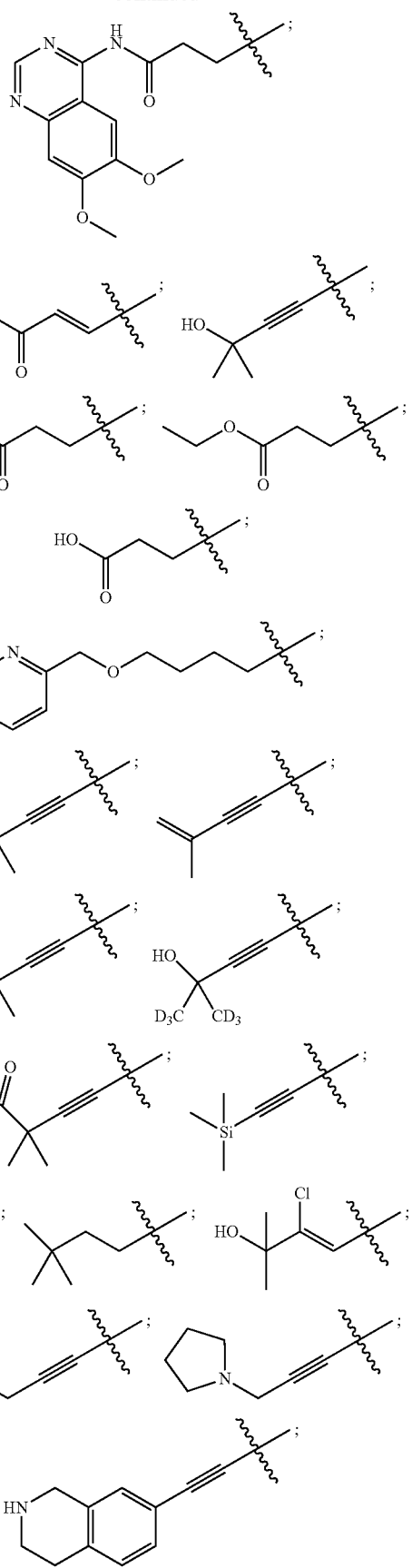

-continued
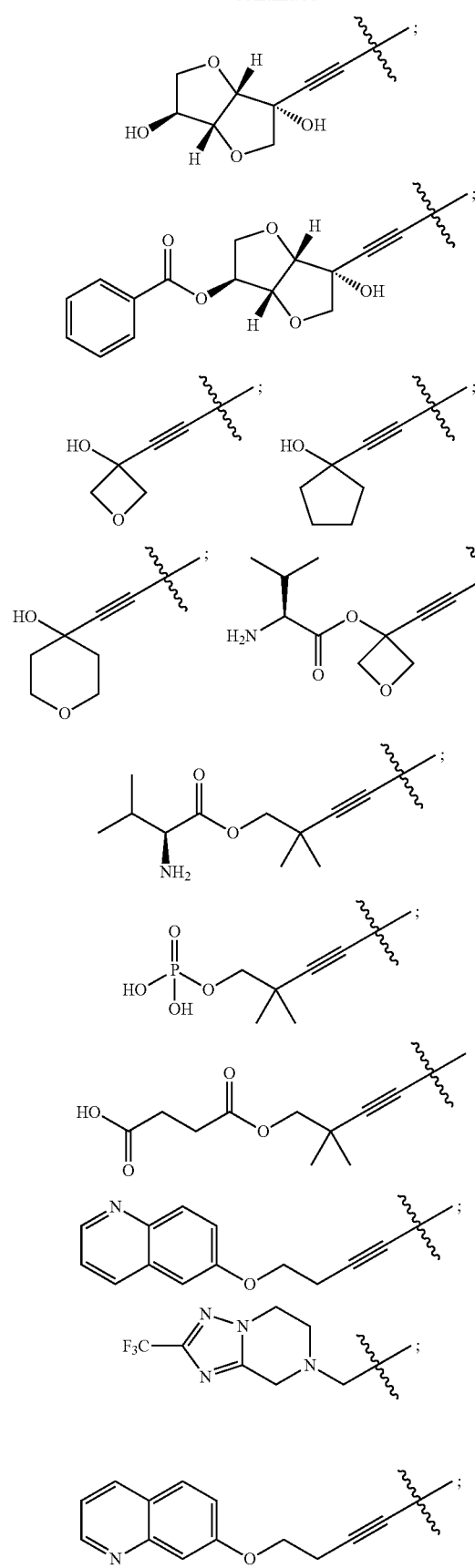
-continued
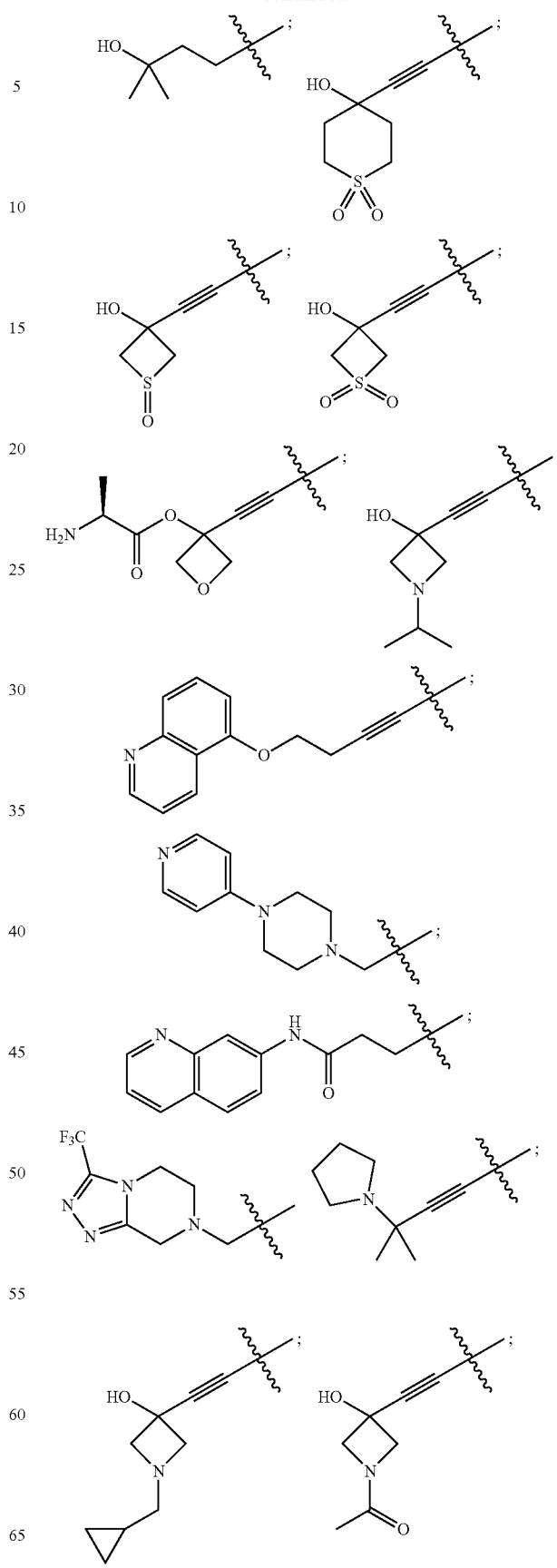

-continued

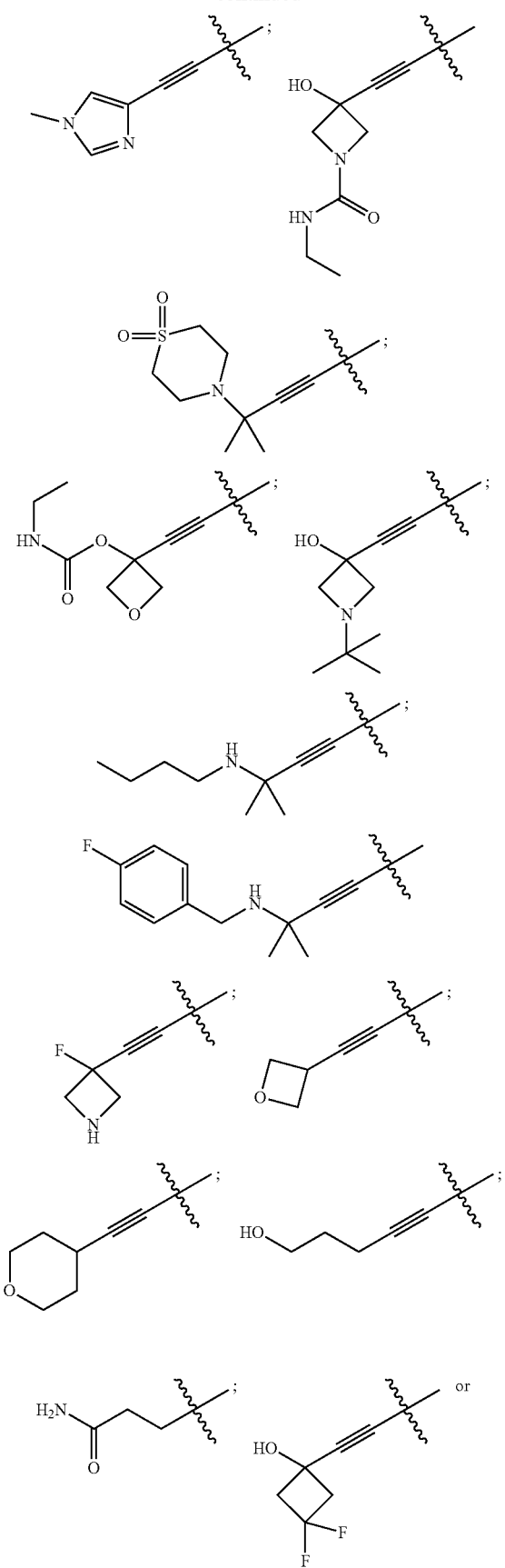

-continued

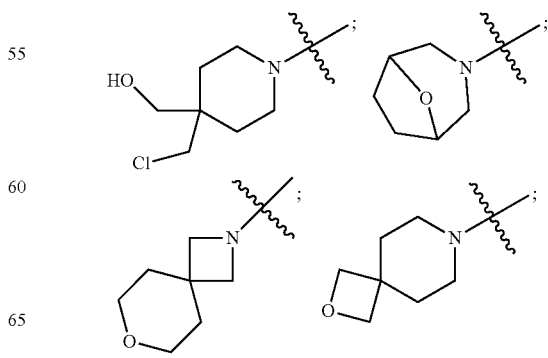

In other embodiments, $R^1$ is heterocyclyl, such as $-NR^dR^d$ wherein two $R^d$ groups together with the nitrogen bound thereto provide a $C_{3-10}$heterocyclic group. In some embodiments when two $R^d$ groups together with the nitrogen bound thereto provide a $C_{3-10}$heterocyclic group, the $C_{3-10}$heterocyclic group is substituted with one or more $R^e$ groups and/or has one or more additional heteroatoms in addition to the nitrogen to which both $R^d$ groups are bound in certain embodiments. In some embodiments, the $C_{3-10}$heterocyclic group is substituted with two $R^e$ groups that join together to provide a $C_{3-10}$heterocyclic group and this $C_{3-10}$heterocyclic, along with the $R^b$ group can provide a spirocyclic group or a bicyclic group. Certain disclosed spirocyclic groups comprise at least two rings, with each ring having a different number of atoms in the ring. In some embodiments, the spirocyclic group comprises at least two rings, wherein a first ring and a second ring of the spirocyclic group have a different number of carbon atoms, a different number of heteroatoms, or both. In yet additional embodiments, each ring of the spirocyclic group comprises a heteroatom in the ring, and each ring of the spirocyclic group may have a different heteroatom in the ring or the same heteroatom in the ring, such as at least one oxygen atom and at least one nitrogen atom. In some embodiments, the spirocyclic group comprises a first ring comprising a nitrogen atom and a second ring comprising an oxygen atom. The spirocyclic group comprises a first ring coupled to the ring A phenyl group, wherein the first ring has from 3 to 7 atoms and a second ring has from 3 to 7 atoms. Typically, the spirocyclic group comprises greater than 7 total atoms in the spirocyclic system, with some embodiments having a spirocyclic group that comprises 9 total atoms in the spirocyclic system. The $C_{3-10}$heterocyclic formed by the two $R^e$ groups and the $C_{3-10}$heterocyclic formed by the two $R^d$ groups of $R^b$ may provide a bicyclic group, such as a bicyclic group comprising two or more heteroatoms in the bicyclic group, such as nitrogen and/or oxygen. The bicyclic group may be attached to the ring A phenyl group through a nitrogen atom of the bicyclic group. In some embodiments, the bicyclic group may be a fused bicyclic group or a bridged bicyclic group.

In any or all of Formulas I, IA, IB, IC, ID, II and III, IV, IVA and IVB as well as in the Formulas V, VA, VB, VC, VD and VI described below, $R^1$ is selected from -continued

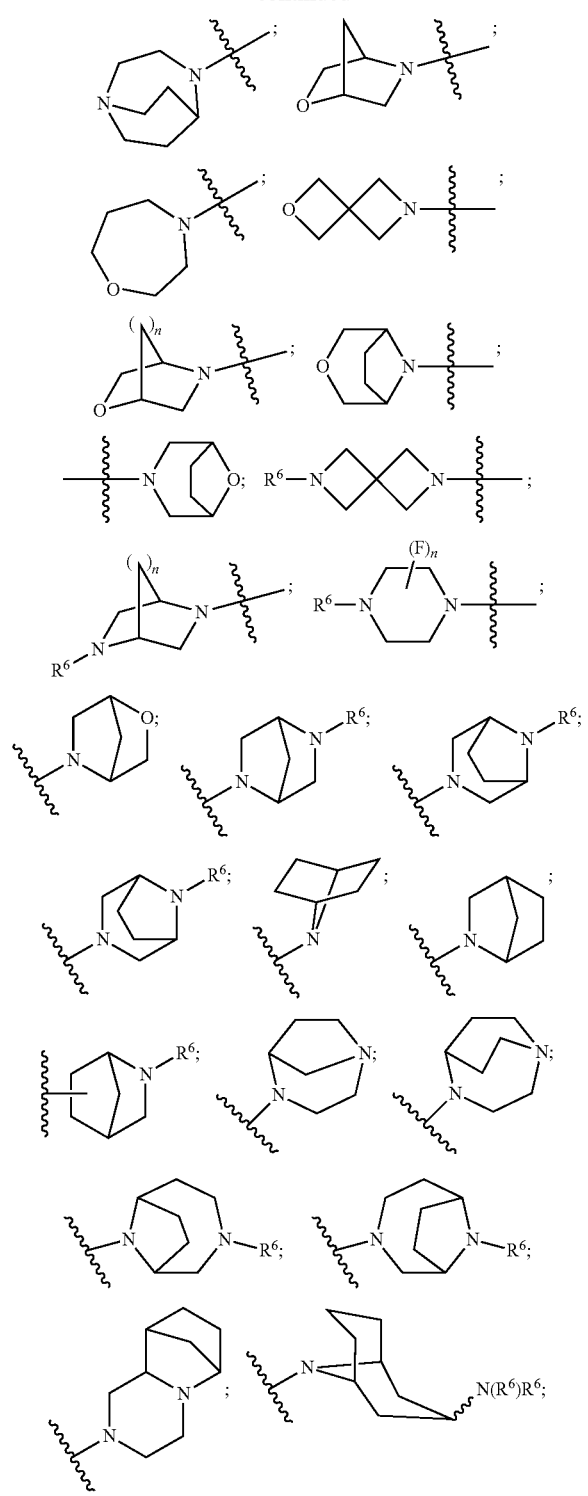

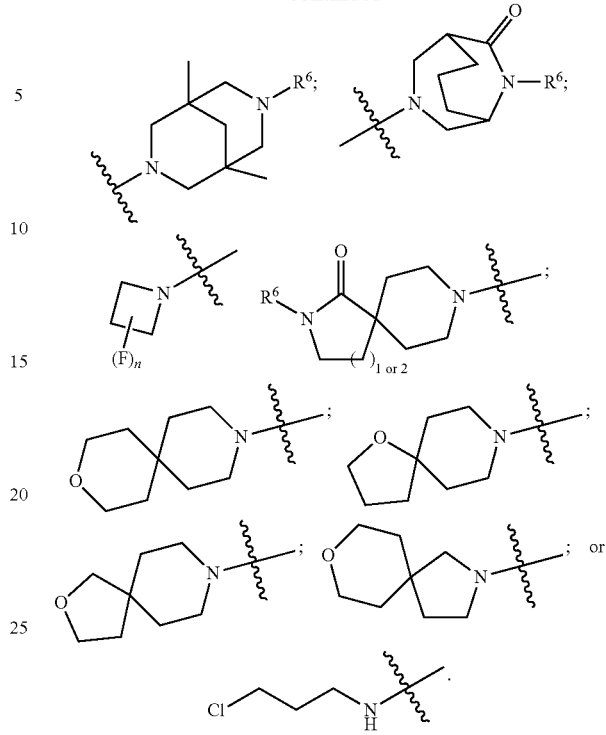

With respect to Formulas I, IA, IB, IC, II, III, IV, IVA and IVB, $Y^1$, $Y^2$ and $Y^3$ are independently selected from the group consisting of N, $N(R^a)$, O, $C(R^b)_{1-2}$ and C=O. In one embodiment of the Formulas above the disclosed compounds have Formula V Formula V

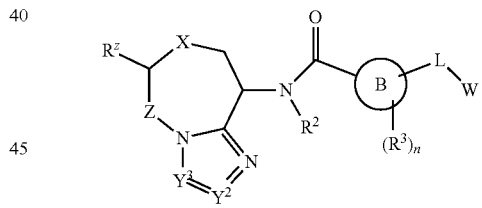

wherein the bond between $Y^2$ and $Y^3$ is single or double, such as in Formulas VA, VB, VC or VD illustrated below. With continued reference to Formula V, in certain embodiments $Y^2$ and $Y^3$ are each $CH_2$. In other embodiments of Formula V, $Y^2$ and $Y^3$ are independently selected from the group consisting of $CH_2$ and CHCl, such as when $Y^2$ is $CH_2$ and $Y^3$ is CHCl, or $Y^2$ is CHCl and $Y^3$ is $CH_2$.

Formula VA

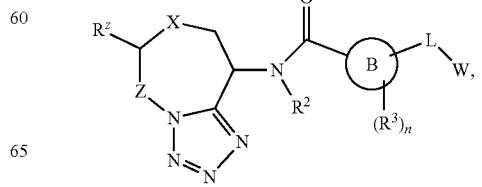

-continued

Formula VB

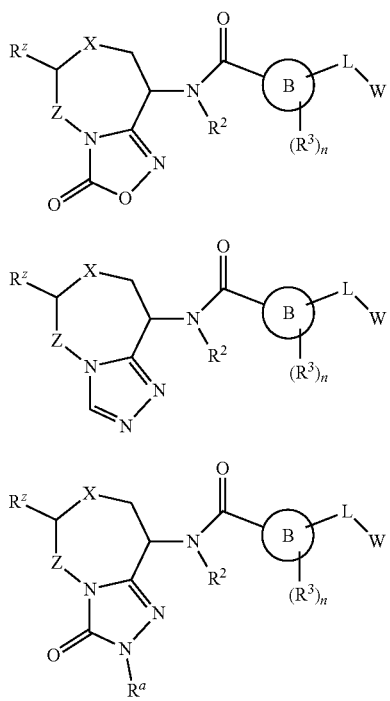

Formula VC

Formula VD

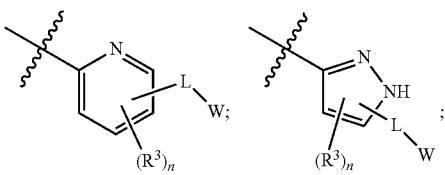

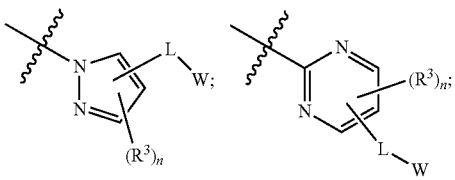

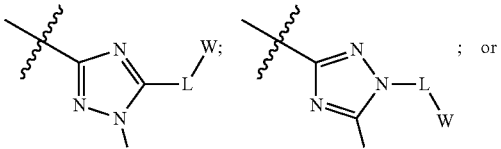

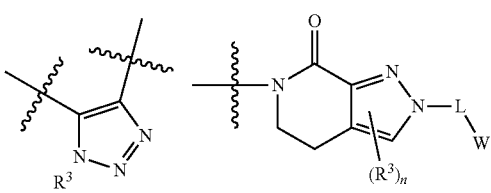

In another embodiment of Formulas I, IA, IB, II, III, IV, IVA and IVB, the disclosed compounds have Formula VI Formula VI

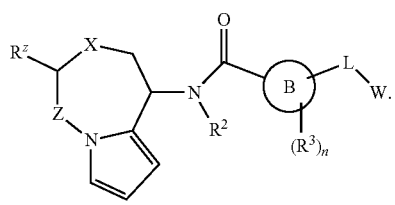

With reference to the Formulas above, $R^2$ can be any suitable substituent, such as an $R^a$ moiety, such as hydrogen, $C_{1-6}$alkyl or $C_{1-6}$acyl, for example hydrogen or methyl. When $R^2$ is methyl, the methyl moiety may be —$CD_3$—that is, the methyl group may be enriched in deuterium relative to its natural abundance.

With respect to Formulas IA, IB, II, III, IV, IVA, IVB, V, VA, VB, VC, VD and VI, ring B is heteroaryl, such as a 5-10 membered heteroaryl group, for example a 5-membered or 6-membered heteroaryl. In some embodiments, ring B is a 5-membered or 6-membered heteroaryl wherein the heteroaryl has one or two ring or three nitrogen atoms and the remainder of the ring atoms are carbon, such as a pyrrole, diazole or triazole. In other embodiments, ring B is oxazole, thiazole or isoxazole. In certain embodiments, ring B is pyrazolyl, and in other particular embodiments, ring B is pyridinyl or pyrimidinyl. In certain embodiments ring B is a bicyclic ring system wherein at least one ring is aromatic. Examples of such bicyclic ring systems for B include, without limitation dihydropyrrolotriazole, triazolopyridine, imidazolopyridine, tetrahydrotriazolopyrazine, tetrahydropyrazolopyridine and the like. In certain embodiments, the group B has the formula In particular embodiments of Formulas IA, IB, II, III, IV, IVA, IVB, V, VA, VB, VC, VD and VI, wherein ring B is a 5-membered heteroaryl group, ring B can have a structure satisfying formula

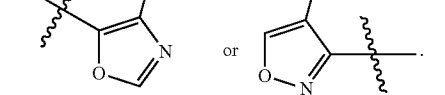

wherein at least one W is nitrogen, and each remaining W independently is selected from carbon, CH, oxygen, sulfur, nitrogen, or NH. In some embodiments, the 5-membered heteroaryl group is a diazole, a triazole, an oxadiazole, or an oxazole. Exemplary triazoles include any of the following:

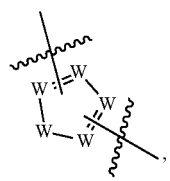

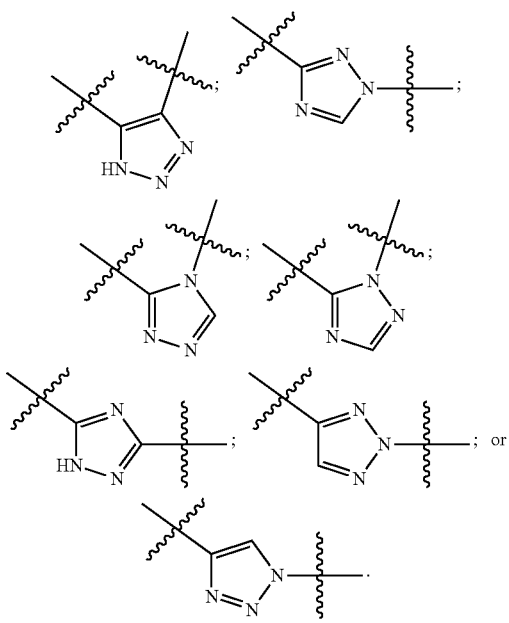

Exemplary diazoles are selected from any of the following:

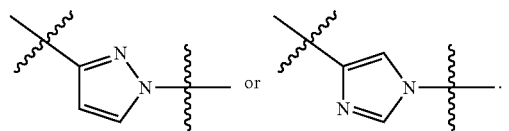 [SMILES: *c1ccn(*)n1 ; *c1cn(*)cn1]

Exemplary oxazoles are selected from any of the following:

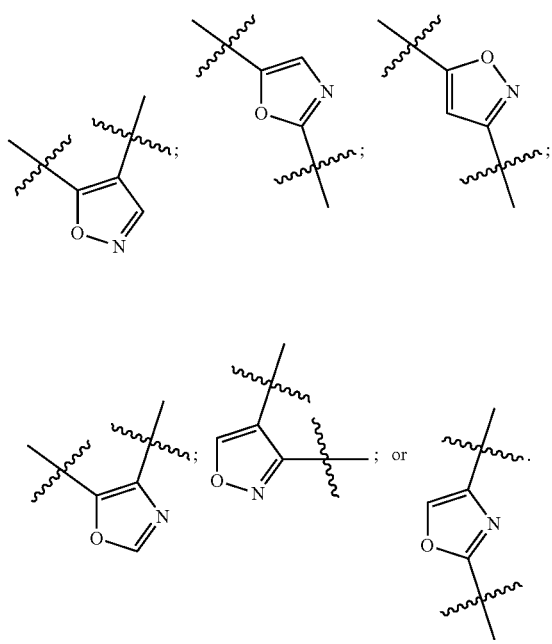

Exemplary oxadiazoles are selected from any of the following:

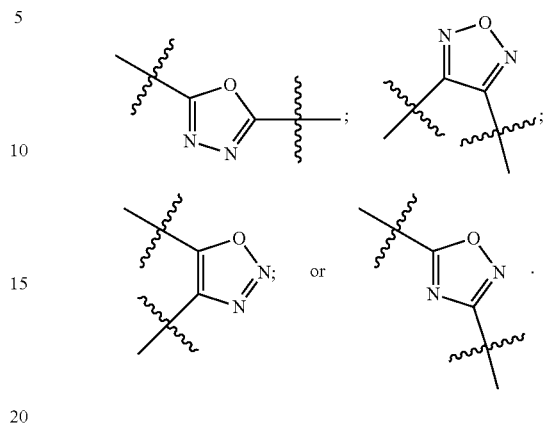

As noted above with reference to I, IA, IB, II, III, IV, IVA, IVB, V, VA, VB, VC, VD and VI, the "B" ring optionally is substituted, such as with $R^b$ and $OR^a$, wherein for each occurrence $R^b$ is selected from $C_{1-6}$alkyl, such as methyl, and halo, such as fluoro or chloro.

With continued reference to Formulas I, IA, IB, II, III, IV, IVA, IVB, V, VA, VB, VC, VD and VI, L is a linker moiety such as O, $N(R^a)$, $-NR^a-$, alkylene, cycloalkanyl or a combination thereof. The alkylene moiety may be optionally interrupted with one or more $-O-$, $-N(R^a)-$ or $-NR^a-$. By way of example, such linker moieties include, without limitation, $-(CH_2)_m-R^e$, $-(CHR^a)_m-R^e$, $-O-(CH_2)_m-R^e$, $-C(O)NH-(CH_2)_m-R^e$, $-C(O)NH-(CHR^a)_m-R^e$, $-O-(CH_2)_m-C(O)NH-(CH_2)_m-R^e$, such as $-CH_2-$, $-CH(Me)-$, $-C(Me)_2-$, $-CH_2CH_2-$, $-CH_2CH_2CH_2-$, $-CH_2CH_2CH_2CH_2-$, $-CF_2-$, $-CH(F)$; as well as cycloalkanyl, such as cyclopropyl, cyclobutyl, cyclopentyl and cyclohexyl groups, optionally substituted with one or more $R^b$.

In Formulas IA, IB, II, III, IV, IVA, IVB, V, VA, VB, VC, VD and VI, the W moiety is a 5-10 membered aryl or heteroaryl optionally substituted by p $R^4$ groups, wherein; $R^4$ is, for each occurrence, selected from $R^b$ and $OR^a$. In certain embodiments of the disclosed compounds, W is selected from

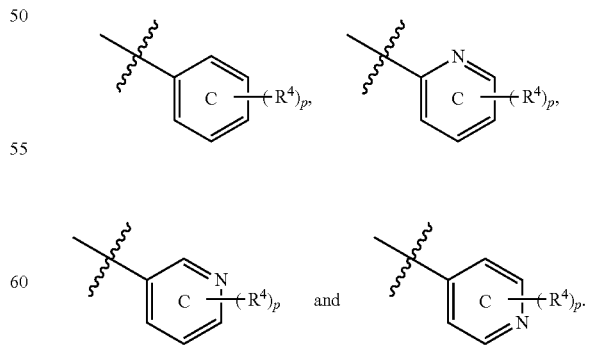

Certain disclosed exemplary compounds within the scope of one or more of Formulas I, IA, IB, II, III, IV, IVA, IVB, V, VA, VB, VC, VD and VI are listed in Table 1.

TABLE 1
| Compound structure | |
|---|---|
| 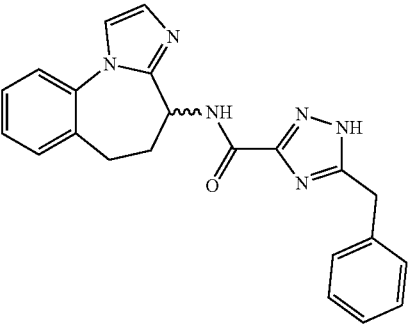 [SMILES: O=C(NC1CCc2ccccc2-n2ccnc21)c1n[nH]c(Cc2ccccc2)n1] | I-1 |
| 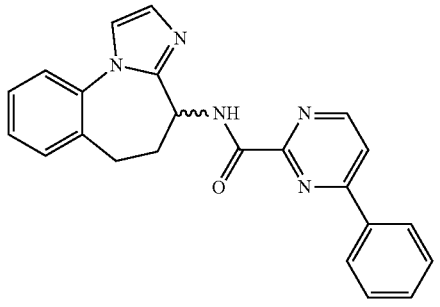 [SMILES: O=C(NC1CCc2ccccc2-n2ccnc21)c1nccc(-c2ccccc2)n1] | I-2 |
| 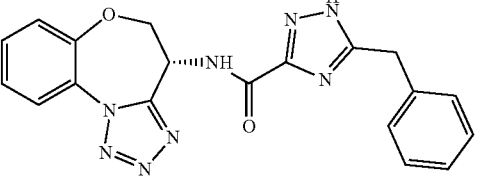 | I-3 |
| 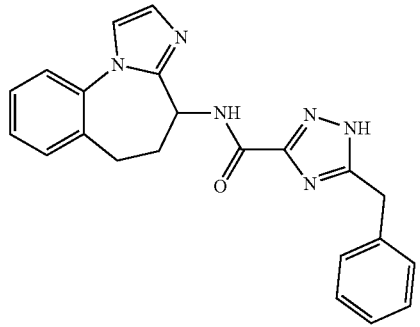 [SMILES: O=C(NC1CCc2ccccc2-n2ccnc21)c1n[nH]c(Cc2ccccc2)n1] | I-4 |
| 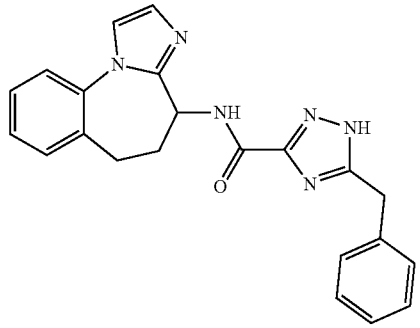 [SMILES: O=C(NC1CCc2ccccc2-n2ccnc21)c1n[nH]c(Cc2ccccc2)n1] | I-5 |

TABLE 1-continued
Compound structure
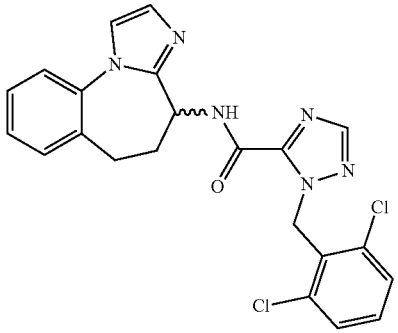 [SMILES: O=C(NC1CCc2ccccc2-n2ccnc21)c1ncnn1Cc1c(Cl)cccc1Cl]
I-6
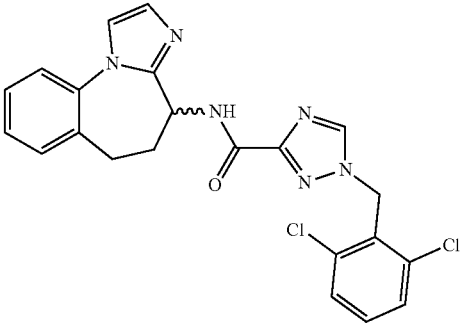 [SMILES: O=C(NC1CCc2ccccc2-n2ccnc21)c1ncn(Cc2c(Cl)cccc2Cl)n1]
I-7
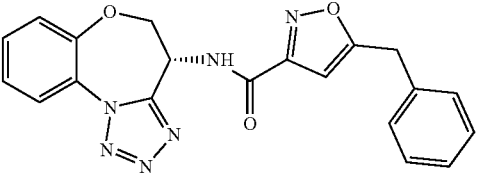 [SMILES: O=C(N[C@H]1COc2ccccc2-n2nnnc21)c1cc(Cc2ccccc2)on1]
I-8
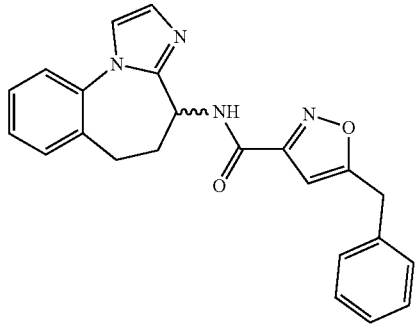 [SMILES: O=C(NC1CCc2ccccc2-n2ccnc21)c1cc(Cc2ccccc2)on1]
I-9
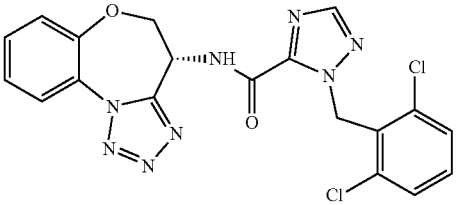 [SMILES: O=C(N[C@H]1COc2ccccc2-n2nnnc21)c1ncnn1Cc1c(Cl)cccc1Cl]
I-10
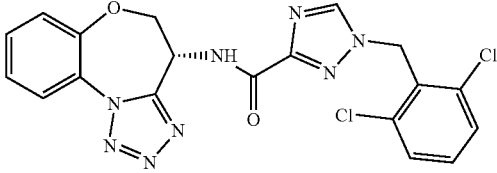 [SMILES: O=C(N[C@H]1COc2ccccc2-n2nnnc21)c1ncn(Cc2c(Cl)cccc2Cl)n1]
I-11

TABLE 1-continued
Compound structure
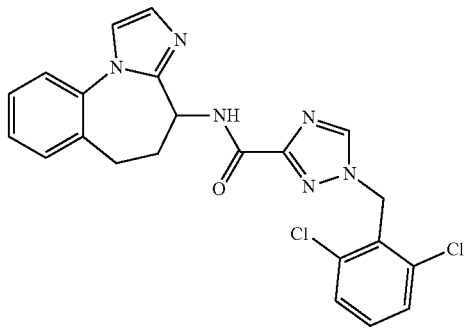 [SMILES: O=C(NC1CCc2ccccc2-n2ccnc21)c1ncn(Cc2c(Cl)cccc2Cl)n1]
I-12
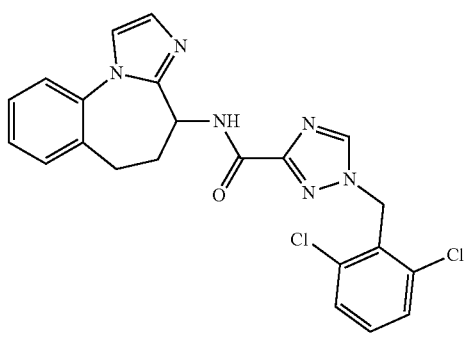 [SMILES: O=C(NC1CCc2ccccc2-n2ccnc21)c1ncn(Cc2c(Cl)cccc2Cl)n1]
I-13
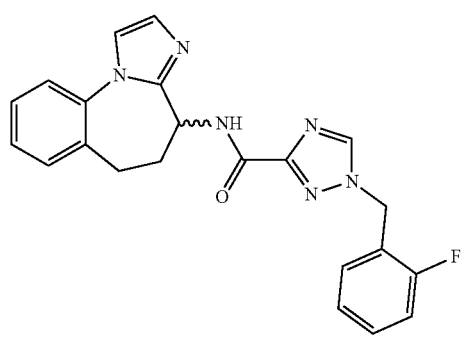 [SMILES: O=C(NC1CCc2ccccc2-n2ccnc21)c1ncn(Cc2ccccc2F)n1]
I-14
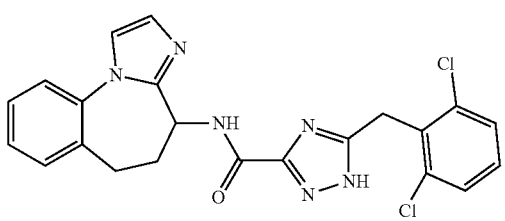 [SMILES: O=C(NC1CCc2ccccc2-n2ccnc21)c1n[nH]c(Cc2c(Cl)cccc2Cl)n1]
I-19
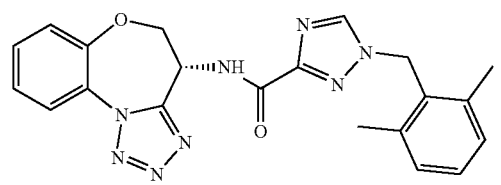 [SMILES: Cc1cccc(C)c1Cn1cnc(C(=O)N[C@H]2COc3ccccc3-n3nnnc32)n1]
I-20
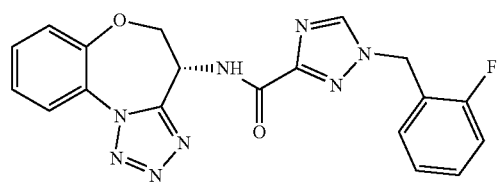 [SMILES: O=C(N[C@H]1COc2ccccc2-n2nnnc21)c1ncn(Cc2ccccc2F)n1]
I-21

TABLE 1-continued
Compound structure
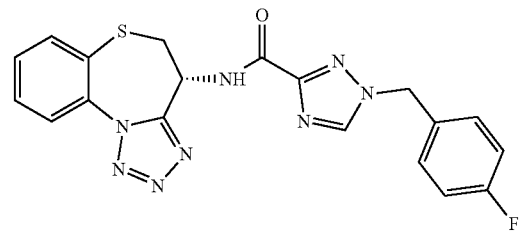 [SMILES: O=C(N[C@H]1CSc2ccccc2-n2nnnc21)c1ncn(Cc2ccc(F)cc2)n1] I-22
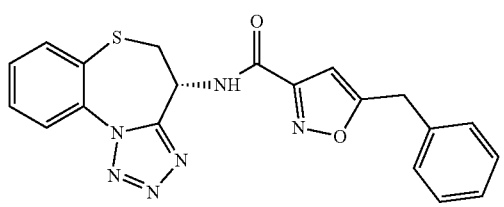 [SMILES: O=C(N[C@H]1CSc2ccccc2-n2nnnc21)c1cc(Cc2ccccc2)on1] I-23
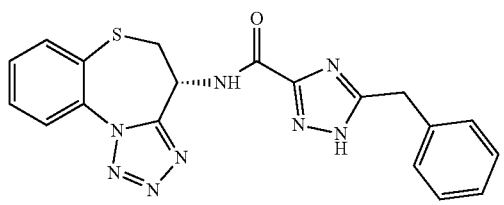 [SMILES: O=C(N[C@H]1CSc2ccccc2-n2nnnc21)c1n[nH]c(Cc2ccccc2)n1] I-24
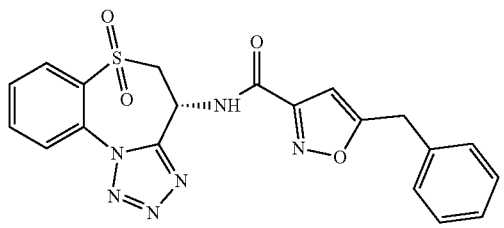 I-25
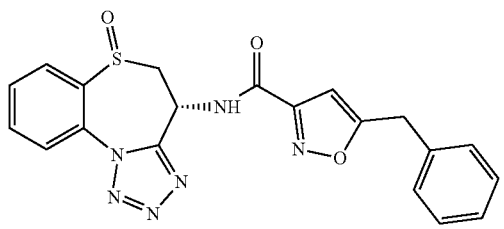 [SMILES: O=C(N[C@H]1CS(=O)c2ccccc2-n2nnnc21)c1cc(Cc2ccccc2)on1] I-26
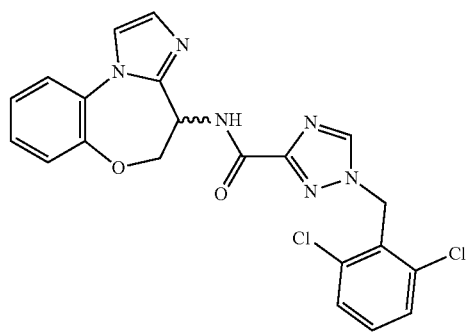 [SMILES: O=C(NC1COc2ccccc2-n2ccnc21)c1ncn(Cc2c(Cl)cccc2Cl)n1] I-27

TABLE 1-continued
Compound structure
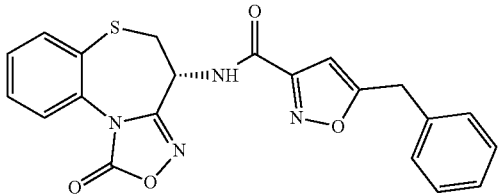 [SMILES: O=C(N[C@H]1CSc2ccccc2-n2c1noc2=O)c1cc(Cc2ccccc2)on1] I-28
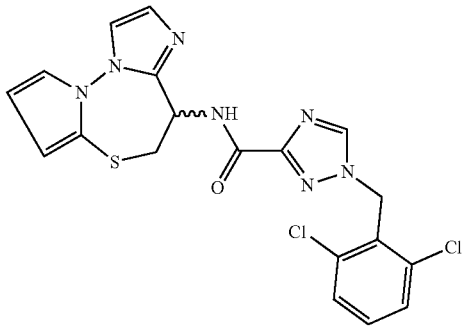 [SMILES: O=C(NC1CSc2cccn2-n2ccnc21)c1ncn(Cc2c(Cl)cccc2Cl)n1] I-29
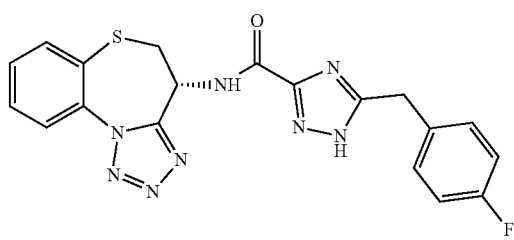 [SMILES: O=C(N[C@H]1CSc2ccccc2-n2nnnc21)c1n[nH]c(Cc2ccc(F)cc2)n1] I-30
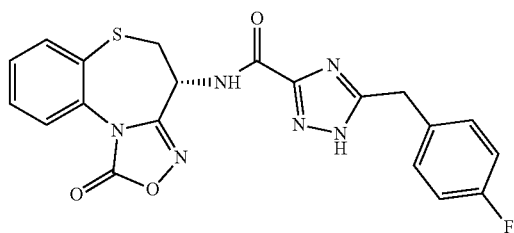 [SMILES: O=C(N[C@H]1CSc2ccccc2-n2c1noc2=O)c1n[nH]c(Cc2ccc(F)cc2)n1] I-31
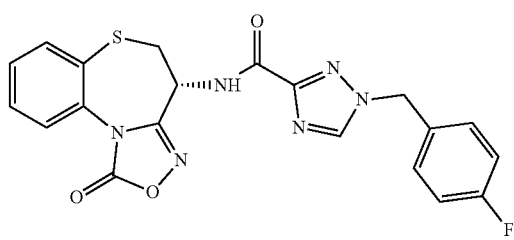 [SMILES: O=C(N[C@H]1CSc2ccccc2-n2c1noc2=O)c1ncn(Cc2ccc(F)cc2)n1] I-32
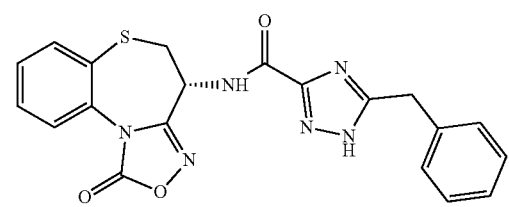 [SMILES: O=C(N[C@H]1CSc2ccccc2-n2c1noc2=O)c1n[nH]c(Cc2ccccc2)n1] I-33

TABLE 1-continued

| Compound structure | |
|---|---|
| (structure) | I-34 |
| (structure) | I-35 |
| (structure) | I-36 |
| (structure) | I-37 |
| (structure) | I-38 |

TABLE 1-continued

Compound structure

I-39

I-40

I-41

I-42

I-43

TABLE 1-continued

| Compound structure | |
|---|---|
| (structure) | I-44 |
| (structure) | I-45 |
| (structure) | I-46 |
| (structure) | I-47 |
| (structure) | I-48 |
| (structure) | I-49 |

TABLE 1-continued
| Compound structure | |
|---|---|
| 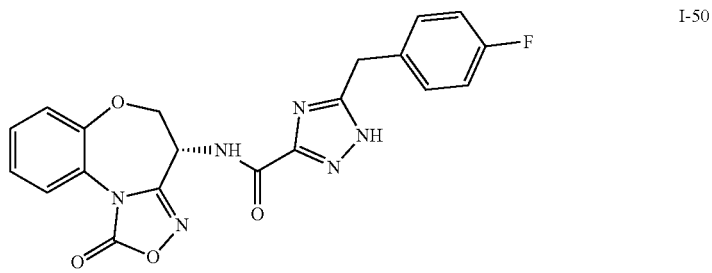 | I-50 |
| 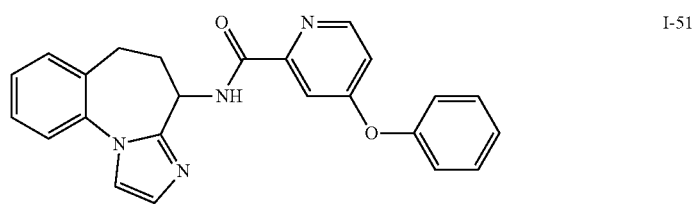 | I-51 |
| 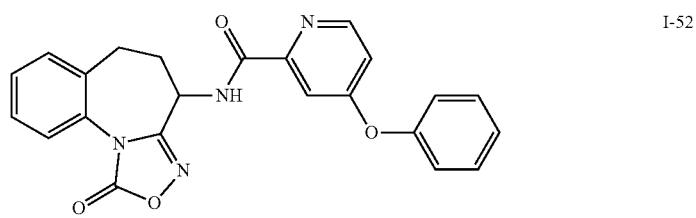 | I-52 |
| 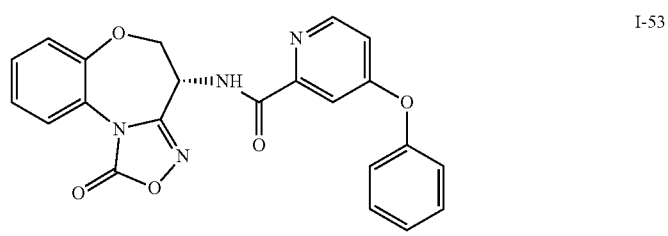 | I-53 |
| 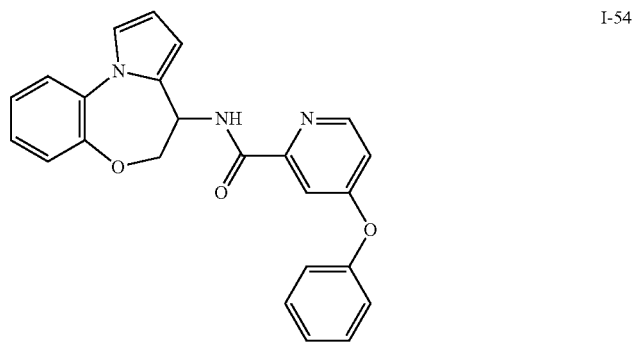 | I-54 |
| 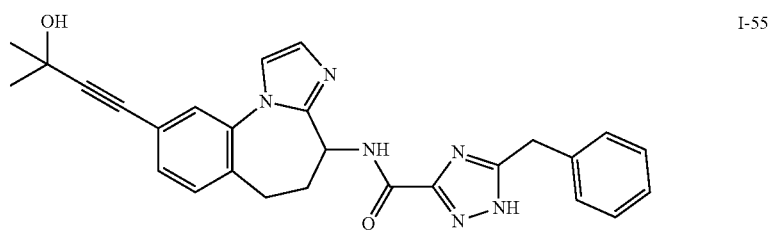 | I-55 |

TABLE 1-continued

| Compound structure | |
|---|---|
| (structure) | I-56 |
| (structure) | I-57 |
| (structure) | I-58 |
| (structure) | I-59 |

TABLE 1-continued
Compound structure
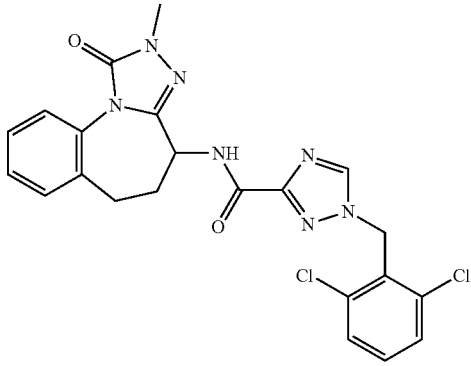 [SMILES: Cn1nc2n(c1=O)-c1ccccc1CCC2NC(=O)c1ncn(Cc2c(Cl)cccc2Cl)n1]
I-60
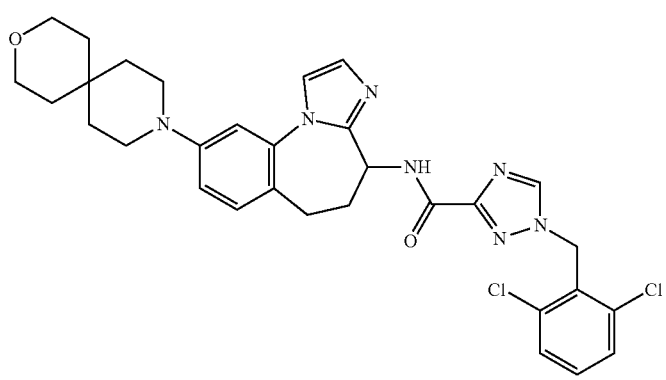 [SMILES: O=C(NC1CCc2ccc(N3CCC4(CCOCC4)CC3)cc2-n2ccnc21)c1ncn(Cc2c(Cl)cccc2Cl)n1]
I-61
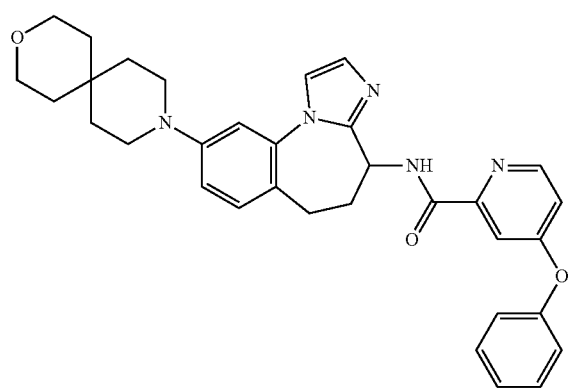 [SMILES: O=C(NC1CCc2ccc(N3CCC4(CCOCC4)CC3)cc2-n2ccnc21)c1cc(Oc2ccccc2)ccn1]
I-62
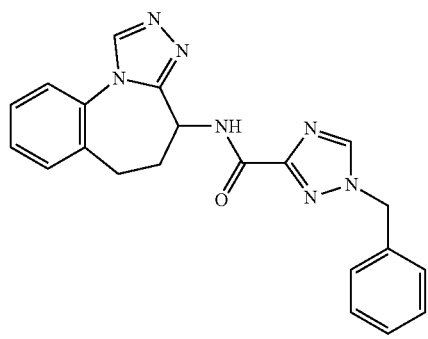 [SMILES: O=C(NC1CCc2ccccc2-n2cnnc21)c1ncn(Cc2ccccc2)n1]
I-63

TABLE 1-continued

Compound structure

I-64

I-65

I-66

I-67

I-68

TABLE 1-continued
Compound structure
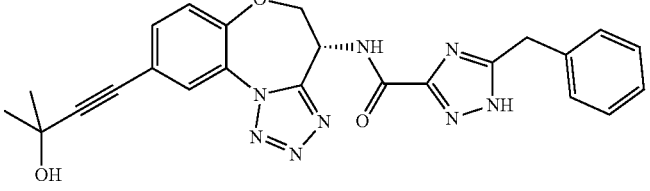 I-69
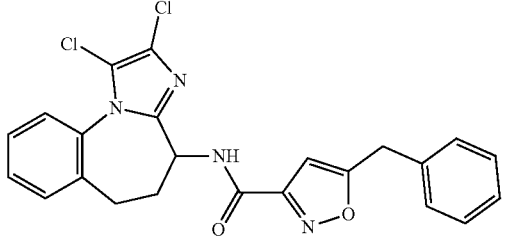 [SMILES: O=C(NC1CCc2ccccc2-n2c1nc(Cl)c2Cl)c1cc(Cc2ccccc2)on1] I-70
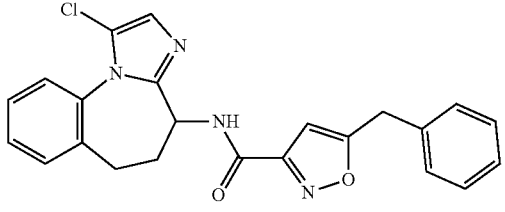 [SMILES: O=C(NC1CCc2ccccc2-n2c(Cl)cnc21)c1cc(Cc2ccccc2)on1] I-71
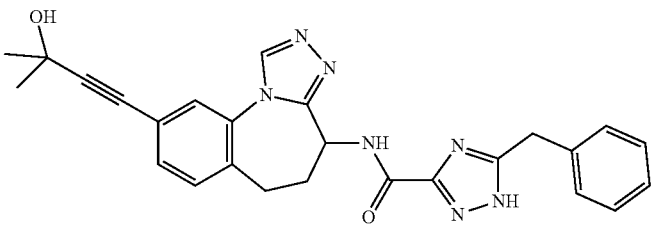 [SMILES: CC(C)(O)C#Cc1ccc2c(c1)-n1cnnc1C(NC(=O)c1n[nH]c(Cc3ccccc3)n1)CC2] I-72
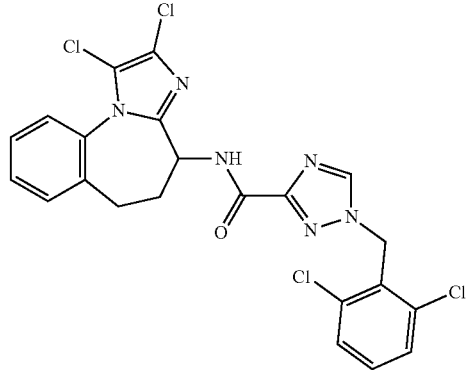 [SMILES: O=C(NC1CCc2ccccc2-n2c1nc(Cl)c2Cl)c1ncn(Cc2c(Cl)cccc2Cl)n1] I-73

TABLE 1-continued
Compound structure
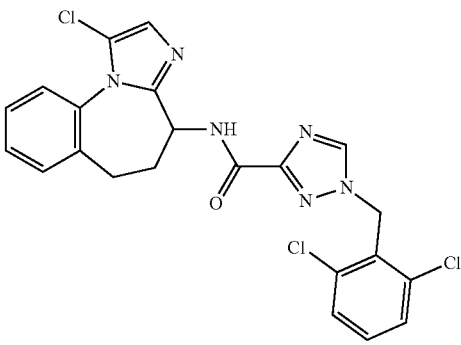 [SMILES: O=C(NC1CCc2ccccc2-n2c(Cl)cnc21)c1ncn(Cc2c(Cl)cccc2Cl)n1]
I-74
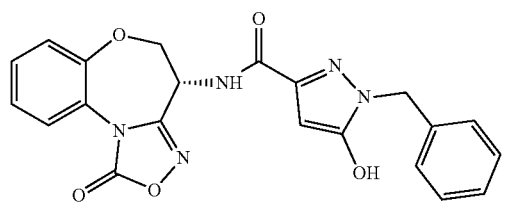 [SMILES: O=C(N[C@H]1COc2ccccc2-n2c1noc2=O)c1cc(O)n(Cc2ccccc2)n1]
I-75
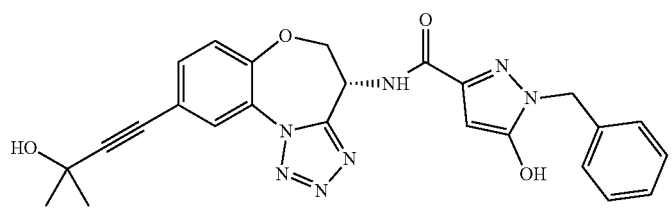 [SMILES: CC(C)(O)C#Cc1ccc2c(c1)-n1nnnc1[C@@H](NC(=O)c1cc(O)n(Cc3ccccc3)n1)CO2]
I-76
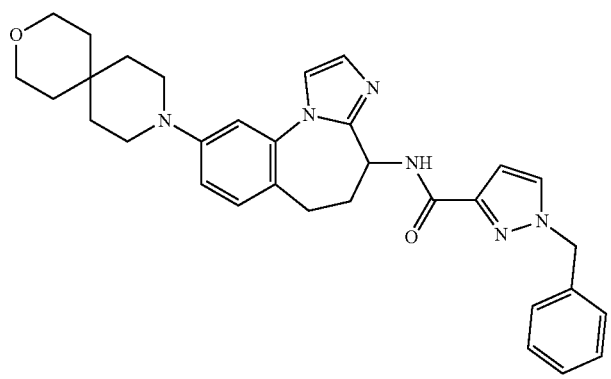 [SMILES: O=C(NC1CCc2ccc(N3CCC4(CCOCC4)CC3)cc2-n2ccnc21)c1ccn(Cc2ccccc2)n1]
I-77
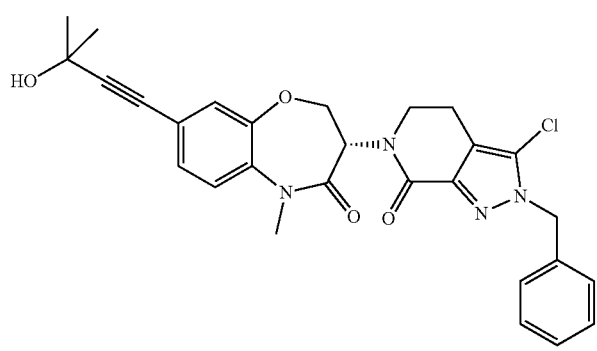 [SMILES: CN1C(=O)[C@@H](N2CCc3c(nn(Cc4ccccc4)c3Cl)C2=O)COc2cc(C#CC(C)(C)O)ccc21]
I-78

TABLE 1-continued
| Compound structure | |
|---|---|
| 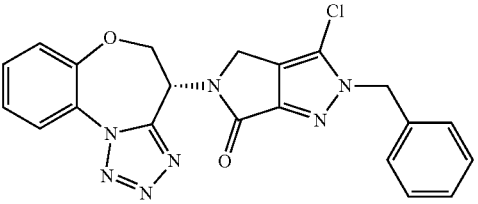 [SMILES: O=C1c2nn(Cc3ccccc3)c(Cl)c2CN1[C@H]1COc2ccccc2-n2nnnc21] | I-79 |
| 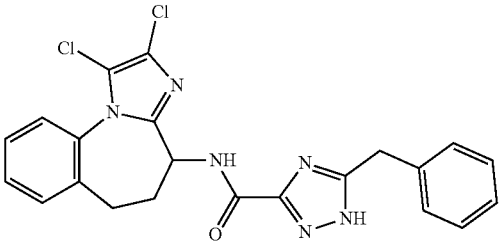 [SMILES: O=C(NC1CCc2ccccc2-n2c1nc(Cl)c2Cl)c1n[nH]c(Cc2ccccc2)n1] | I-80 |
| 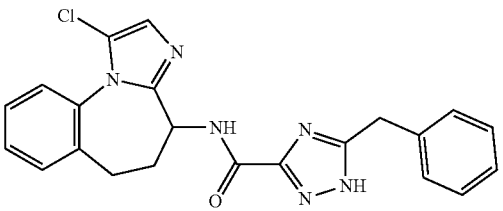 [SMILES: O=C(NC1CCc2ccccc2-n2c(Cl)cnc21)c1n[nH]c(Cc2ccccc2)n1] | I-81 |
| 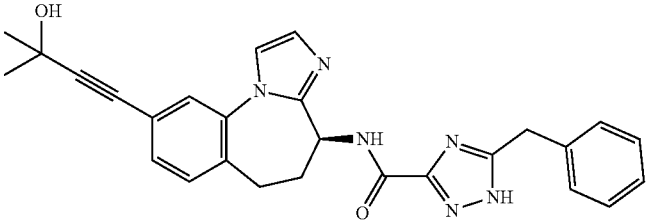 | I-82 |
| 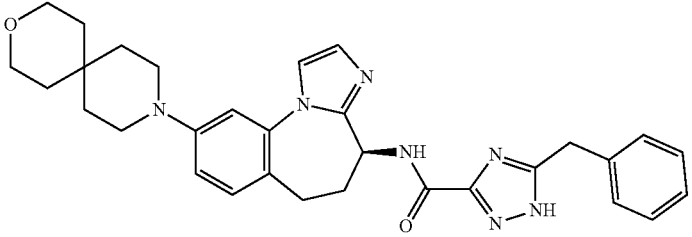 [SMILES: O=C(N[C@H]1CCc2ccc(N3CCC4(CCOCC4)CC3)cc2-n2ccnc21)c1n[nH]c(Cc2ccccc2)n1] | I-83 |
| 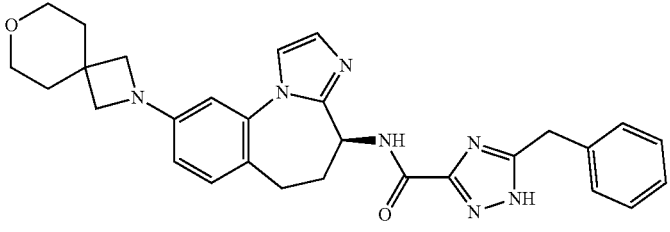 [SMILES: O=C(N[C@H]1CCc2ccc(N3CC4(CCOCC4)C3)cc2-n2ccnc21)c1n[nH]c(Cc2ccccc2)n1] | I-84 |

TABLE 1-continued

| Compound structure | |
|---|---|
| (structure) | I-85 |
| (structure) | I-86 |
| (structure) | I-87 |
| (structure) | I-88 |
| (structure) | I-89 |

TABLE 1-continued

Compound structure

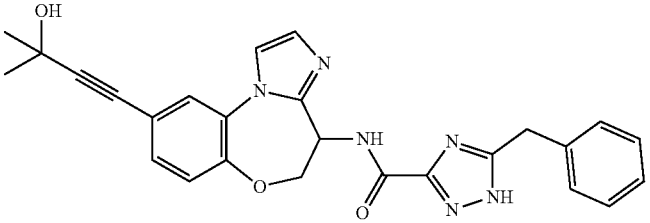 [SMILES: CC(C)(O)C#Cc1ccc2c(c1)-n1ccnc1C(NC(=O)c1n[nH]c(Cc3ccccc3)n1)CO2]

I-90

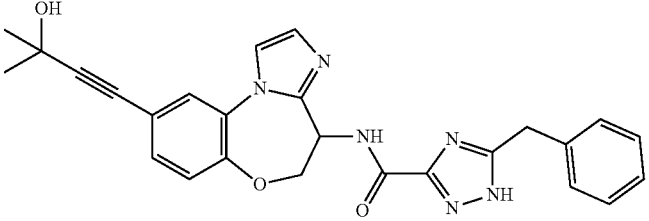 [SMILES: CC(C)(O)C#Cc1ccc2c(c1)-n1ccnc1C(NC(=O)c1n[nH]c(Cc3ccccc3)n1)CO2]

I-91

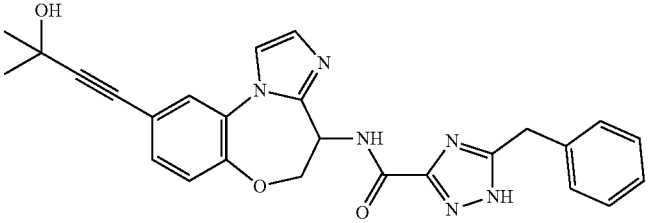 [SMILES: CC(C)(O)C#Cc1ccc2c(c1)-n1ccnc1C(NC(=O)c1n[nH]c(Cc3ccccc3)n1)CO2]

I-92

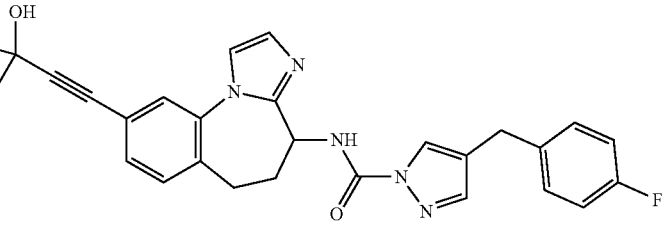

I-93

A person of ordinary skill in the art will appreciate that certain compounds disclosed herein may exhibit the phenomena of tautomerism, conformational isomerism, geometric isomerism, and/or optical isomerism. For example, certain disclosed compounds can include one or more chiral centers and/or double bonds and as a consequence can exist as stereoisomers, such as double-bond isomers (i.e., geometric isomers), enantiomers, diastereomers, and mixtures thereof, such as racemic mixtures. As another example, certain disclosed compounds can exist in several tautomeric forms, including the enol form, the keto form, and mixtures thereof. As the various compound names, formulae and compound drawings within the specification and claims can represent only one of the possible tautomeric, conformational isomeric, optical isomeric, or geometric isomeric forms, a person of ordinary skill in the art will appreciate that the disclosed compounds encompass any tautomeric, conformational isomeric, optical isomeric, and/or geometric isomeric forms of the compounds described herein, as well as mixtures of these various different isomeric forms. Mixtures of different isomeric forms, including mixtures of enantiomers and/or stereoisomers, can be separated to provide each separate stereoisomer techniques known to those of ordinary skill in the art, and those illustrated in the present disclosure. In cases of limited rotation, e.g. around an amide bond or between two directly attached rings such as pyridinyl rings, biphenyl groups, and the like, atropisomers are possible and are simply interconverting forms of compounds of the disclosure.

B. Pharmaceutical Compositions

In some embodiments, one or more of the compounds can be included in a pharmaceutical composition or medicament, and in some embodiments the compound or compounds can be in the form of the parent compound or a pharmaceutically acceptable salt, a co-crystal, a stereoisomer, an N-oxide, a tautomer, a hydrate, a solvate, an isotope, or a prodrug thereof. The pharmaceutical composition typically includes at least one additional component other than a disclosed compound or compounds, such as a pharmaceutically acceptable excipient, an adjuvant, an additional therapeutic agent (described in the following section), or any combination thereof.

Pharmaceutically acceptable excipients can be included in pharmaceutical compositions for a variety of purposes, such as to dilute a pharmaceutical composition for delivery to a subject, to facilitate processing of the formulation, to provide advantageous material properties to the formulation, to facilitate dispersion from a delivery device, to stabilize the formulation (e.g., antioxidants or buffers), to provide a pleasant or palatable taste or consistency to the formulation, or the like. The pharmaceutically acceptable excipient(s) may include a pharmaceutically acceptable carrier(s). Exemplary excipients include, but are not limited to: mono-, di-, and polysaccharides, sugar alcohols and other polyols, such as, lactose, glucose, raffinose, melezitose, lactitol, maltitol, trehalose, sucrose, mannitol, starch, or combinations thereof; surfactants, such as sorbitols, diphosphatidyl choline, and lecithin; bulking agents; buffers, such as phosphate and citrate buffers; anti-adherents, such as magnesium stearate; binders, such as saccharides (including disaccharides, such as sucrose and lactose), polysaccharides (such as starches, cellulose, microcrystalline cellulose, cellulose ethers (such as hydroxypropyl cellulose), gelatin, synthetic polymers (such as polyvinylpyrrolidone, polyalkylene glycols); coatings (such as cellulose ethers, including hydroxypropylmethyl cellulose, shellac, corn protein zein, and gelatin); release aids (such as enteric coatings); disintegrants (such as crospovidone, crosslinked sodium carboxymethyl cellulose, and sodium starch glycolate); fillers (such as dibasic calcium phosphate, vegetable fats and oils, lactose, sucrose, glucose, mannitol, sorbitol, calcium carbonate, and magnesium stearate); flavors and sweeteners (such as mint, cherry, anise, peach, apricot or licorice, raspberry, and vanilla; lubricants (such as minerals, exemplified by talc or silica, fats, exemplified by vegetable stearin, magnesium stearate or stearic acid); preservatives (such as antioxidants exemplified by vitamin A, vitamin E, vitamin C, retinyl palmitate, and selenium, amino acids, exemplified by cysteine and methionine, citric acid and sodium citrate, parabens, exemplified by methyl paraben and propyl paraben); colorants; compression aids; emulsifying agents; encapsulation agents; gums; granulation agents; and combinations thereof.

III. METHODS FOR USING COMPOUNDS

A. Diseases/Disorders

The disclosed compounds, as well as combinations and/or pharmaceutical compositions thereof, may be used to inhibit a RIP1 kinase by contacting the kinase either in vivo or ex vivo, with a compound or compounds of the present disclosure, or a composition comprising a compound or compounds of the present disclosure. Disclosed compound or compounds, or compositions comprising a disclosed compound or compounds also can be used to ameliorate, treat or prevent a variety of diseases and/or disorders. In particular embodiments, the disclosed compound, combinations of disclosed compounds, or pharmaceutical compositions thereof, may be useful for treating conditions in which inhibition of RIP1 or a pathway involving RIP1 is therapeutically useful. In some embodiments, the compounds directly inhibit RIP1 kinase activity. In certain embodiments, disclosed compounds are useful for treating autoimmune diseases, inflammatory disorders, cardiovascular diseases, nerve disorders, neurodegenerative disorders, allergic disorders, respiratory diseases, kidney diseases, cancers, ischemic conditions, erythrocyte deficiencies, lung and brain injuries (e.g., induced by ischemia-reperfusion or cisplatin and/or cerebrovascular accident), and bacterial and viral infections.

In some embodiments, the disclosed compound, combinations of disclosed compounds, or pharmaceutical compositions thereof, may be used to treat or prevent allergic diseases, amyotrophic lateral sclerosis (ALS), spinal muscular atrophy, systemic lupus erythematosus, rheumatoid arthritis, type I diabetes mellitus, inflammatory bowel disease, biliary cirrhosis, uveitis, multiple sclerosis, Crohn's disease, ulcerative colitis, bullous pemphigoid, sarcoidosis, psoriasis, autoimmune myositis, Wegener's granulomatosis, ichthyosis, Graves ophthalmyopathy, or asthma.

The disclosed compound, combinations of disclosed compounds, or pharmaceutical compositions thereof, may also be useful for treating immune regulatory disorders related to bone marrow or organ transplant rejection or graft-versus-host disease. Examples of inflammatory and immune regulatory disorders that can be treated with the compounds (or pharmaceutical compositions or combinations thereof) include, but are not limited to, transplantation of organs or tissue, graft-versus-host diseases brought about by transplantation, autoimmune syndromes including rheumatoid arthritis, systemic lupus erythematosus, Hashimoto's thyroiditis, multiple sclerosis, systemic sclerosis, systemic inflammatory response syndrome, myasthenia gravis, type I diabetes, uveitis, posterior uveitis, allergic encephalomyelitis, glomerulonephritis, postinfectious autoimmune diseases including rheumatic fever and post-infectious glomerulonephritis, inflammatory and hyperproliferative skin diseases, psoriasis, atopic dermatitis, contact dermatitis, eczematous dermatitis, seborrhoeic dermatitis, hidradenitis suppurativa, lichen planus, pemphigus, bullous pemphigoid, epidermolysis bullosa, urticaria, angioedemas, vasculitis, erythema, cutaneous eosinophilia, lupus erythematosus, acne, alopecia areata, keratoconjunctivitis, vernal conjunctivitis, uveitis associated with Behcet's disease, keratitis, herpetic keratitis, conical cornea, dystrophia epithelialis corneae, corneal leukoma, ocular pemphigus, Mooren's ulcer, scleritis, Graves' opthalmopathy, Vogt-Koyanagi-Harada syndrome, sarcoidosis, pollen allergies, reversible obstructive airway disease, bronchial asthma, allergic asthma, intrinsic asthma, extrinsic asthma, dust asthma, chronic or inveterate asthma, late asthma and airway hyper-responsiveness, bronchitis, gastric ulcers, vascular damage caused by ischemic diseases and thrombosis, ischemic bowel diseases, ischemia-reperfusion injuries, inflammatory bowel diseases, necrotizing enterocolitis, intestinal lesions associated with thermal burns, celiac diseases, proctitis, eosinophilic gastroenteritis, mastocytosis, Crohn's disease, ulcerative colitis, migraine, rhinitis, eczema, interstitial nephritis, Goodpasture's syndrome, hemolytic-uremic syndrome, diabetic nephropathy, multiple myositis, Guillain-Barre syndrome, Meniere's disease, polyneuritis, multiple neuritis, mononeuritis, radiculopathy, hyperthyroidism, Basedow's disease, pure red cell aplasia, aplastic anemia, hypoplastic anemia, idiopathic thrombocytopenic purpura, autoimmune hemolytic anemia, agranulocytosis, pernicious anemia, megaloblastic anemia, anerythroplasia, osteoporosis, sarcoidosis, fibroid lung, idiopathic interstitial pneumonia, dermatomyositis, leukoderma vulgaris, ichthyosis vulgaris, photoallergic sensitivity, cutaneous T cell lymphoma, chronic lymphocytic leukemia, arteriosclerosis, atherosclerosis, aortitis syndrome, polyarteritis nodosa, myocardosis or myocardial infarction, scleroderma (including systemic scleroderma), anti-phospholipid syndrome, Wegener's granuloma, Sjögren's syndrome, adiposis, eosinophilic fasciitis, lesions of gingiva, periodontium, alveolar bone, substantia ossea dentis, glomerulonephritis, male pattern alopecia or alopecia senilis by preventing epilation or providing hair germination and/or promoting hair generation and hair growth, muscular dystrophy, pyoderma and Sezary's syndrome, Addison's disease, ischemia-reperfusion injury of organs which occurs upon preservation, transplantation or ischemic disease, endotoxin-shock, pseudomembranous colitis, colitis caused by drug or radiation, ischemic acute renal insufficiency, chronic renal insufficiency, toxinosis caused by lung-oxygen or drugs, lung cancer, pulmonary emphysema, cataracta, siderosis, retinitis pigmentosa, retinal degeneration, retinal detachment, senile macular degeneration, vitreal scarring, corneal alkali burn, dermatitis erythema multiforme, linear IgA ballous dermatitis and cement dermatitis, gingivitis, periodontitis, sepsis, pancreatitis, diseases caused by environmental pollution, aging, carcinogenesis, metastasis of carcinoma and hypobaropathy, disease caused by histamine or leukotriene-C4 release, Behcet's disease, autoimmune hepatitis, primary biliary cirrhosis, sclerosing cholangitis, partial liver resection, acute liver necrosis, necrosis caused by toxin, viral hepatitis, shock, or anoxia, B-virus hepatitis, non-A/non-B hepatitis, cirrhosis, alcoholic liver disease, including alcoholic cirrhosis, alcoholic steatohepatitis, non-alcoholic steatohepatitis (NASH), autoimmune hepatobiliary diseases, acetaminophen toxicity, hepatotoxicity, hepatic failure, fulminant hepatic failure, late-onset hepatic failure, "acute-on-chronic" liver failure, chronic kidney diseases, kidney damage/injury (caused by, for example, nephritis, renal transplant, surgery, administration of nephrotoxic drugs, acute kidney injury), augmentation of chemotherapeutic effect, cytomegalovirus infection, HCMV infection, AIDS, cancer, senile dementia, Parkinson's disease, trauma, or chronic bacterial infection.

In certain embodiments the present compounds are useful for treating nerve pain, including neuropathic pain and inflammation induced pain.

In certain embodiments, the compounds are useful for treating interleukin-1 converting enzyme-associated associated fever syndrome, tumor necrosis factor receptor-associated periodic syndrome, NEMO-deficiency syndrome, HOIL-1 deficiency, linear ubiquitin chain assembly complex deficiency syndrome, lysosomal storage diseases (e.g., Gaucher disease, GM2 gangliosidosis, alpha-mannosidosis, aspartylglucosaminuria, cholesteryl ester storage disease, chronic hexosaminidase A deficiency, cystinosis, Danon disease, Fabry disease, Farber disease, fucosidosis, galactosialidosis, GM1 gangliosidosis, mucolipidosis, infantile free sialic acid storage disease, juvenile hexosaminidase A deficiency, Krabbe disease, lysosomal acid lipase deficiency, metachromatic leukodystrophy, mucopolysaccharidoses disorders, multiple sulfatase deficiency, Niemann-Pick disease, neuronal ceroid lipofuscinoses, Pompe disease, pycnodysostosis, Sandhoff disease, Schindler disease, sialic acid storage disease, Tay-Sach disease, and Wolman disease).

In certain embodiments, the disclosed compound, combinations of disclosed compounds, or pharmaceutical compositions thereof, are useful for treating and/or preventing rheumatoid arthritis, psoriatic arthritis, osteoarthritis, systemic lupus erythematosus, lupus nephritis, ankylosing spondylitis, osteoporosis, systemic sclerosis, multiple sclerosis, psoriasis, in particular pustular psoriasis, type I diabetes, type II diabetes, inflammatory bowel disease (Crohn's disease and ulcerative colitis), hyperimmunoglobulinemia D syndrome and periodic fever syndrome, such as cryopyrin-associated periodic syndromes, Familial Mediterranean Fever (FMF) syndrome, Schnitzler's syndrome, and TNF-Receptor-Associated Periodic fever syndrome (TRAPS), systemic juvenile idiopathic arthritis, adult's onset Still's disease, gout, gout flares, pseudogout, sapho syndrome, Castleman's disease, sepsis, stroke, atherosclerosis, celiac disease, DIRA (deficiency of Il-1 receptor antagonist), The disclosed RIP1K inhibitors are particularly useful for the treatment of neurological disorders, including, as mentioned above, neurodegenerative disorders. By way of example the present compounds can be used to treat Alzheimer's disease, ALS, Huntington's disease, and Parkinson's disease.

Proliferative diseases that may be treated by the disclosed compound, combinations of disclosed compounds, or pharmaceutical compositions thereof, include benign or malignant tumors, solid tumor, carcinoma of the brain, kidney, liver, adrenal gland, bladder, breast, stomach, gastric tumors, ovaries, colon, rectum, prostate, pancreas, lung, vagina, cervix, testis, genitourinary tract, esophagus, larynx, skin, bone or thyroid, sarcoma, glioblastomas, neuroblastomas, multiple myeloma, gastrointestinal cancer, especially colon carcinoma or colorectal adenoma, a tumor of the neck and head, an epidermal hyperproliferation, psoriasis, prostate hyperplasia, a neoplasia, a neoplasia of epithelial character, adenoma, adenocarcinoma, keratoacanthoma, epidermoid carcinoma, large cell carcinoma, non-small-cell lung carcinoma, lymphomas, Hodgkins and Non-Hodgkins, a mammary carcinoma, follicular carcinoma, undifferentiated carcinoma, papillary carcinoma, seminoma, melanoma, IL-1 driven disorders, a MyD88 driven disorder (such as ABC diffuse large B-cell lymphoma (DLBCL), Waldenström's macroglobulinemia, Hodgkin's lymphoma, primary cutaneous T-cell lymphoma or chronic lymphocytic leukemia), smoldering or indolent multiple myeloma, or hematological malignancies (including leukemia, acute myeloid leukemia (AML), DLBCL, ABC DLBCL, chronic lymphocytic leukemia (CLL), chronic myeloid leukemia (CML), primary effusion lymphoma, Burkitt lymphoma/leukemia, acute lymphocytic leukemia, B-cell prolymphocytic leukemia, lymphoplasmacytic lymphoma, myelodysplastic/myeloproliferative neoplasms (MDS/MPN) such as chronic myelomonocytic leukemia (CMML, including CMML-0, CMML-1 and CMML-2), myelofibrosis, polycythemia vera, Kaposi's sarcoma, Waldenström's macroglobulinemia (WM), splenic marginal zone lymphoma, multiple myeloma, plasmacytoma, intravascular large B-cell lymphoma). In particular, the presently disclosed compounds are useful in treating drug resistant malignancies, such as those resistant to JAK inhibitors or BTK inhibitors, such as ibrutinib resistant malignancies, including ibrutinib resistant hematological malignancies, such as ibrutinib resistant CLL and ibrutinib resistant Waldenström's macroglobulinemia.

Despite CMML having certain clinical and pathological features of both a myeloproliferative neoplasm (MPN) and a myelodysplastic syndrome (MDS), CMML is classified by the World Health Organization (WHO) in a separate category of an MDS/MPN overlap group. (Arber et al. "*The 2016 revision to the World Health Organization classification of myeloid neoplasms and acute leukemia*" Blood, vol. 127, number 20, pages 2391-2405, May 19, 2016.) According to the WHO, the diagnosis of CMML now requires both the presence of persistent peripheral blood monocytosis of $\geq 1 \times 10^9$/L and monocytes accounting for $\geq 10\%$ of the white blood cell (WBC) differential count. Additionally, CMML can only be diagnosed per the definition when rearrangements in PDGFRA, PDGFRB or FGFR1 genes have been excluded, and in the 2016 update, the PCM1-JAK2 fusion gene was added as an excluding criterion. In some embodiments, a method for treating CMML comprises identifying a subject having the WHO diagnosis criteria (i.e., persistent peripheral blood monocytosis of $\geq 1 \times 10^9$/L and monocytes accounting for $\geq 10\%$ of the white blood cell differential count) and excluding rearrangements in PDGFRA, PDGFRB, FGFR1, or PCM1-JAK2 genes), and treating the subject by administering a RIP1 inhibitor disclosed herein, combinations of such compounds, and/or compositions thereof.

Examples of allergic disorders that may be treated using the disclosed compound, combinations of disclosed compounds, or pharmaceutical compositions thereof, include, but are not limited to, asthma (e.g. atopic asthma, allergic asthma, atopic bronchial IgE-mediated asthma, non-atopic asthma, bronchial asthma, non-allergic asthma, essential asthma, true asthma, intrinsic asthma caused by pathophysiologic disturbances, essential asthma of unknown or unapparent cause, emphysematous asthma, exercise-induced asthma, emotion-induced asthma, extrinsic asthma caused by environmental factors, cold air induced asthma, occupational asthma, infective asthma caused by or associated with bacterial, fungal, protozoal, or viral infection, incipient asthma, wheezy infant syndrome, bronchiolitis, cough variant asthma or drug-induced asthma), allergic bronchopulmonary aspergillosis (ABPA), allergic rhinitis, perennial allergic rhinitis, perennial rhinitis, vasomotor rhinitis, post-nasal drip, purulent or non-purulent sinusitis, acute or chronic sinusitis, and ethmoid, frontal, maxillary, or sphenoid sinusitis.

As another example, rheumatoid arthritis (RA) typically results in swelling, pain, loss of motion and tenderness of target joints throughout the body. RA is characterized by chronically inflamed synovium that is densely crowded with lymphocytes. The synovial membrane, which is typically one cell layer thick, becomes intensely cellular and assumes a form similar to lymphoid tissue, including dendritic cells, T-, B- and NK cells, macrophages and clusters of plasma cells. This process, as well as a plethora of immunopathological mechanisms including the formation of antigen-immunoglobulin complexes, eventually result in destruction of the integrity of the joint, resulting in deformity, permanent loss of function and/or bone erosion at or near the joint. The disclosed compound, combinations of disclosed compounds, or pharmaceutical compositions thereof, may be used to treat, ameliorate or prevent any one, several or all of these symptoms of RA. Thus, in the context of RA, the compounds are considered to provide therapeutic benefit when a reduction or amelioration of any of the symptoms commonly associated with RA is achieved, regardless of whether the treatment results in a concomitant treatment of the underlying RA and/or a reduction in the amount of circulating rheumatoid factor ("RF").

The American College of Rheumatology (ACR) has developed criteria for defining improvement and clinical remission in RA. Once such parameter, the ACR20 (ACR criteria for 20% clinical improvement), requires a 20% improvement in the tender and swollen joint count, as well as a 20% improvement in 3 of the following 5 parameters: patient's global assessment, physician's global assessment, patient's assessment of pain, degree of disability, and level of acute phase reactant. These criteria have been expanded for 50% and 70% improvement in ACR50 and ACR70, respectively. Other criteria include Paulu's criteria and radiographic progression (e.g. Sharp score).

In some embodiments, therapeutic benefit in patients suffering from RA is achieved when the patient exhibits an ACR20. In specific embodiments, ACR improvements of ACRC50 or even ACR70 may be achieved.

Additional diseases or disorders that can be treated and/or prevented using compounds and compositions of the present invention include spondyloarthritis, including axial spondyloarthritis, such as ankylosing spondylitis, SoJIA, autoimmune hepatitis, autoimmune hepatobiliary diseases, autoimmune ITP, cerebrovascular accident, myocardial infarction, allergic diseases, chronic obstructive pulmonary disease, cardiac infarction, HIV-associated dementia, glaucoma, Friedreich's ataxia, Lewy body disease, spinal cord injury, diabetic neuropathy, polyglutamine (polyQ) diseases, stroke, Fahr disease, Menke's disease, Wilson's disease, cerebral ischemia, prion disorder, destructive bone disorders such as bone resorption disease, multiple myeloma-related bone disorder; proliferative disorders such as acute myelogenous leukemia, chronic myelogenous leukemia; angiogenic disorders such as angiogenic disorders including solid tumors, ocular neovascularization, and infantile haemangiomas; infectious diseases such as sepsis, septic shock, and Shigellosis; neurodegenerative diseases such as metastatic melanoma, HIV infection and CMV retinitis, fibrotic conditions such as, nonalcoholic steatohepatitis and cardiac conditions such as, ischemia reperfusion; allergies, adult respiratory distress syndrome, chronic obstructive pulmonary disease, glomerulonephriti, erythematosis, chronic thyroiditis, Graves' disease, autoimmune gastritis, autoimmune neutropenia, thrombocytopenia, graft versus host disease, inflammatory reaction induced by endotoxin, tuberculosis, atherosclerosis, muscle degeneration, cachexia, Reiter's syndrome, rubella arthritis, acute synovitis, pancreatic 3-cell disease; diseases characterized by massive neutrophil infiltration; rheumatoid spondylitis, gouty arthritis and other arthritic conditions, cerebral malaria, chronic pulmonary inflammatory disease, silicosis, pulmonary sarcoisosis, allograft rejections, fever and myalgias due to infection, meloid formation, scar tissue formation, ulcerative colitis, pyresis, influenza, chronic myelogenous leukemia; angiogenic disorders including solid tumors; viral diseases including acute hepatitis infection (including hepatitis A, hepatitis B and hepatitis C), AIDS, ARC or malignancy, herpes; stroke, myocardial ischemia, ischemia in stroke heart attacks, organ hyposia, vascular hyperplasia, cardiac and renal reperfusion injury, cardiac hypertrophy, thrombin-induced platelet aggregation, endotoxemia and/or toxic shock syndrome, conditions associated with prostaglandin endoperoxidase syndase-2, pemphigus vulgaris, ischemia reperfusion injury, including cerebral ischemia reperfusions injury arising from stroke, cardiac ischemia reperfusion injury arising from myocardial infarction, multiple system atrophy, Parkinson-plus syndromes, frontotemporal dementia, intracranial hemorrhage, cerebral hemorrhage, progressive muscular atrophy, pseudobulbar palsy, progressive bulbar palsy, spinal muscular atrophy, inherited muscular atrophy, peripheral neuropathies, progressive supranuclear palsy, corticobasal degeneration, demyelinating diseases, spondylarthritis, systemic onset juvenile idiopathic arthritis (SoJIA), systemic lupus erythematosus (SLE), Sjogren's syndrome, anti-phospholipid syndrome (APS), primary sclerosing cholangitis (PSC), renal transplant, surgery, acute kidney injury (AKI), systemic inflammatory response syndrome (SIRS), cerebrovascular accident (CVA), pulmonary sarcoidosis, interleukin-1 converting enzyme (ICE, also known as caspase-1) associated fever syndrome, chronic obstructive pulmonary disease (COPD), periodontitis, NEMO-deficiency syndrome (F-kappa-B essential modulator gene (also known as IKK gamma or IKKG) deficiency syndrome), hematological and solid organ malignancies, Lysosomal storage diseases, glaucoma, spondyloarthritis, retinal degenerative disease, retinal ischemia/reperfusion injury, renal ischemia reperfusion injury, anthrax lethal toxin induced septic shock, cell death induced by LPS, infectious encephalopathy, encephalitis, autoimmune uveoretinitis, giant cell arteritis, regional enteritis, granulomatous enteritis,
distal ileitis, regional ileitis, terminal ileitis, insulin-dependent diabetes mellitus, scleroderma, systemic lupus erythematosus, macular edema, diabetic retinopathy, central areolar choroidal dystrophy, BEST disease, adult vitelliform disease, pattern dystrophy, myopic
degeneration, central serous retinopathy, Stargardt's disease, Cone-Rod dystrophy, North Carolina dystrophy, infectious retinitis, inflammatory retinitis, uveitis, toxic retinitis and light-induced toxicity, macular edema, diabetic retinopathy, central areolar choroidal dystrophy, BEST disease, adult vitelliform disease, pattern dystrophy, optic nerve injury, optic neuritis, optic neuropathies, diabetic retinopathy, central retinal artery occlusion, ischemic optic neuropathy (e.g., arteritic or non-arteritic anterior ischemic neuropathy and posterior ischemic optic neuropathy), compressive optic neuropathy, infiltrative optic neuropathy, traumatic optic neuropathy, mitochondrial optic neuropathy (e.g., Leber's optic neuropathy), nutritional optic neuropathy, toxic optic neuropathy and hereditary optic neuropathy, Dominant Optic Atrophy, Behr's syndrome, Creutzfeldt-Jakob disease), progressive supranuclear palsy, hereditary spastic paresis, subarachnoid hemorrhage, perinatal brain injury, subclinical brain injury, spinal cord injury, anoxic-ischemic brain injury, focal cerebral ischemia, global cerebral ischemia, and hypoxic hypoxia, peritoneal damage caused by peritoneal dialysis fluid (PDF) and PD-related side effects, glomerular diseases, tubulointerstitial diseases, obstruction, polycystic kidney disease), focal glomerulosclerosis, immune complex nephropathy, hepatocellular cancer, pancreatic cancer, urological cancer, bladder cancer, colorectal cancer, colon cancer, breast cancer, prostate cancer, renal cancer, thyroid cancer, gall bladder cancer, peritoneal cancer, ovarian cancer, cervical cancer, gastric cancer, endometrial cancer, esophageal cancer, head and neck cancer, neuroendocrine cancer, CNS cancer, brain tumors (e.g., glioma, anaplastic
oligodendroglioma, adult glioblastoma multiforme, and adult anaplastic astrocytoma), bone cancer, soft tissue sarcoma, retinoblastomas, neuroblastomas, peritoneal effusions, malignant pleural effusions, mesotheliomas, Wilms tumors, trophoblastic neoplasms, hemangiopericytomas, myxoid carcinoma, round cell carcinoma, squamous cell carcinomas, esophageal squamous cell carcinomas, oral carcinomas, vulval cancer, cancers of the adrenal cortex, ACTH producing tumors, lymphoma, and leukemia, respiratory infectious viruses, such as influenza virus, rhino virus, corona virus, parainfluenza virus, RS virus, adeno virus, reo virus and the like), herpes zoster caused by herpes virus, diarrhea caused by rotavirus, viral hepatitis, AIDS, bacterial infectious diseases, such as *Bacillus cereus, Vibrio parahaemolyticus*, Enterohemorrhagic *Escherichia coli, Staphylococcus aureus*, MRS A, *Salmonella, Botulinus, Candida*, Paget's disease, achondroplasia, osteochodrytis, hyperparathyroidism, osteogenesis imperfecta, congenital hypophosphatasia, fribromatous lesions, fibrous displasia, bone turnover, osteolytic bone disease, periodontal disease, treating post-traumatic bone surgery, treating post-prosthetic joint surgery, treating post-plastic bone surgery, treating post-dental surgery, bone chemotherapy treatment or bone radiotherapy treatment, bone cancer, fragile plaque, disorder, occlusive disorder, stenosis, coronary artery disorders, peripheral arterial disorders, arterial occlusion, aneurysm formation, post-traumatic aneurysm formation, restenosis, post-operative graft occlusion, autoimmune idiopathic thrombocytopenic purpura (autoimmune ITP), membranous nephritis, autoimmune thyroiditis, cold and warm agglutinin diseases, Evan's syndrome, hemolytic uremic syndrome/thrombotic thrombocytopenic purpura (HUS/TTP), and pemphigus vulgaris.

B. Combinations of Therapeutic Agents

One of ordinary skill in the art will appreciate that the conditions described above for treatment with the presently disclosed RIP1K inhibitors may benefit from treatment with one or more additional therapeutic agent in combination with a RIP1K inhibitor. Indeed, the RIP1K inhibitor compounds described herein may be used alone, in combination with one another, in separate pharmaceutical compositions, together in a single pharmaceutical composition, or as an adjunct to, or in combination with, other established therapies. The compound or compounds or composition comprising the compound (or compounds) may be administered once, or in plural administrations. In some embodiments, the compounds of the present invention may be used in combination with other therapeutic agents useful for the disorder or condition being treated. These other therapeutic agents may be administered simultaneously, sequentially in any order, by the same route of administration, or by a different route as the presently disclosed compounds. For sequential administration, the compound(s) and the therapeutic agent (s) may be administered such that an effective time period of at least one compound and the therapeutic agent overlaps with an effective time period of at least one other compound and/or therapeutic agent. In an exemplary embodiment of a combination comprising four components, the effective time period of the first component administered may overlap with the effective time periods of the second, third and fourth components, but the effective time periods of the second, third and fourth components independently may or may not overlap with one another. In another exemplary embodiment of a combination comprising four components, the effective time period of the first component administered overlaps with the effective time period of the second component, but not that of the third or fourth; the effective time period of the second component overlaps with those of the first and third components; and the effective time period of the fourth component overlaps with that of the third component only. In some embodiments, the effective time periods of all compounds and/or therapeutic agents overlap with each other.

In some embodiments, the compounds are administered with another therapeutic agent, such as an analgesic, an antibiotic, an anticoagulant, an antibody, an anti-inflammatory agent, an immunosuppressant, a guanylate cyclase-C agonist, an intestinal secretagogue, an antiviral, anticancer, antifungal, or a combination thereof. The anti-inflammatory agent may be a steroid or a nonsteroidal anti-inflammatory agent. In certain embodiments, the nonsteroidal anti-inflammatory agent is selected from aminosalicylates, cyclooxygenase inhibitors, diclofenac, etodolac, famotidine, fenoprofen, flurbiprofen, ketoprofen, ketorolac, ibuprofen, indomethacin, meclofenamate, mefenamic acid, meloxicam, nambumetone, naproxen, oxaprozin, piroxicam, salsalate, sulindac, tolmetin, or a combination thereof. In some embodiments, the immunosuppressant is mercaptopurine, a corticosteroid, an alkylating agent, a calcineurin inhibitor, an inosine monophosphate dehydrogenase inhibitor, antilymphocyte globulin, antithymocyte globulin, an anti-T-cell antibody, or a combination thereof. In one embodiment, the antibody is infliximab.

A compound described herein may be administered in combination with other anti-inflammatory or immune modulating agents for any of the indications above, including oral or topical corticosteroids, anti-TNF agents, 5-aminosalicyclic acid and mesalamine preparations, hydroxycloroquine, thiopurines, methotrexate, cyclophosphamide, cyclosporine, calcineurin inhibitors, mycophenolic acid, mTOR inhibitors, JAK inhibitors, Syk inhibitors, anti-inflammatory biologic agents, including anti-TL6 biologics, anti-IL1 agents, anti-IL17 biologics, anti-CD22, anti-integrin agents, anti-IFNa, anti-CD20 or CD4 biologics and other cytokine inhibitors or biologics to T-cell or B-cell receptors or interleukins.

Particularly in the treatment of rheumatoid arthritis the present RIP1K inhibitors are useful in combination with ibuprofen, naproxen, prednisone, methotrexate, leflunomide, hydroxychloroquine, sulfasalazine, abatacept, adalimumab, anakinra, baracitinib, certolizumab, etanercept, fostamatinib, golimumab, infliximab, rituximab, tocilizumab and tofacitinib.

In some embodiments, the present compounds may be used with anti-cancer or cytotoxic agents. Various classes of anti-cancer and anti-neoplastic compounds include, but are not limited to, alkylating agents, antimetabolites, BCL-2 inhibitors, vinca alkyloids, taxanes, antibiotics, enzymes, cytokines, platinum coordination complexes, proteasome inhibitors, substituted ureas, kinase inhibitors, hormones and hormone antagonists, and hypomethylating agents, for example DNMT inhibitors, such as azacitidine and decitabine. Exemplary alkylating agents include, without limitation, mechlorothamine, cyclophosphamide, ifosfamide, melphalan, chlorambucil, ethyleneimines, methylmelamines, alkyl sulfonates (e.g., busulfan), and carmustine. Exemplary antimetabolites include, by way of example and not limitation, folic acid analog methotrexate; pyrmidine analog fluorouracil, cytosine arbinoside; purine analogs mercaptopurine, thioguanine, and azathioprine. Exemplary vinca alkyloids include, by way of example and not limitation, vinblastine, vincristine, paclitaxel, and colchicine. Exemplary antibiotics include, by way of example and not limitation, actinomycin D, daunorubicin, and bleomycin. An exemplary enzyme effective as an anti-neoplastic agent includes L-asparaginase. Exemplary coordination compounds include, by way of example and not limitation, cisplatin and carboplatin. Exemplary hormones and hormone related compounds include, by way of example and not limitation, adrenocorticosteroids prednisone and dexamethasone; aromatase inhibitors amino glutethimide, formestane, and anastrozole; progestin compounds hydroxyprogesterone caproate, medroxyprogesterone; and anti-estrogen compound tamoxifen.

In one aspect, the present compounds are useful in blocking a cytokine response. Overproduction of pro-inflammatory cytokines can result in a "cytokine storm," during which inflammation spreads throughout the body via the circulation. These cytokines include interferons, interleukins, chemokines, colony-stimulating factors, and tumor necrosis factors and that are produced in an immune response. Overproduction of these cytokines can result in a condition has been referred to as Cytokine Response Syndrome or CRS. The present compounds can be used inhibit production of cytokines and thus ameliorate their destructive effects in CRS. CRS can occur during treatment with therapies wherein the cells express recombinant receptors, such as chimeric antigen receptors (CARs) and/or other transgenic receptors such as T cell receptors (TCRs). Accordingly, the present compounds are useful in combination with CAR-T therapy. Exemplary CAR-T therapies for use in combination with the present compounds include activated T cells; antibodies, including those that activate T cells; YESCARTA; and KYMRIAH are commercially available examples. CRS also can occur in response to serious bacterial and viral infections. In particular on consequence of CRS in response to COVID-19 is acute lung injury that can lead to severe lung damage that results in a condition known as acute respiratory distress syndrome. In one aspect the present compounds are used in patients having or suspected of having COVID-19 to inhibit CRS. In this context the present compounds can be used in combination with anti-viral agents, such as remdesivir. Similarly the present compounds can be used in combination with antibiotics to modulate CRS associated with a bacterial infection.

These and other useful anti-cancer compounds are described in Merck Index, 13th Ed. (O'Neil M. J. et al., ed.) Merck Publishing Group (2001) and Goodman and Gilman's The Pharmacological Basis of Therapeutics, 12th Edition, Brunton L. L. ed., Chapters 60-63, McGraw Hill, (2011), both of which are incorporated by reference herein.

Among the CTLA 4 antibodies that can be used in combination with the presently disclosed inhibitors is ipilimumab, marketed as YERVOY® by Bristol-Myers Squibb.

Other chemotherapeutic agents for combination include immunooncology agents, such as checkpoint pathway inhibitors, for example, PD-1 inhibitors, such as nivolumab and lambrolizumab, and PD-L1 inhibitors, such as pembrolizumab, MEDI-4736 and MPDL3280A/RG7446. Additional checkpoint inhibitors for combination with the compounds disclosed herein include, Anti-LAG-3 agents, such as BMS-986016 (MDX-1408).

Further chemotherapeutic agents for combination with the presently disclosed inhibitors include Anti-SLAMF7 agents, such as the humanized monoclonal antibody elotuzumab (BMS-901608), anti-KIR agents, such as the anti-KIR monoclonal antibody lirilumab (BMS-986015), and anti-CD137 agents, such as the fully human monoclonal antibody urelumab (BMS-663513).

The presently disclosed compounds also may be used advantageously with CAR-T therapies. Example of currently available CAR-T therapies are axicabtagene ciloleucel and tisagenlecleucel.

Additional anti-proliferative compounds useful in combination with the compounds of the present invention include, by way of example and not limitation, antibodies directed against growth factor receptors (e.g., anti-Her2); and cytokines such as interferon-α and interferon-γ, interleukin-2, and GM-CSF.

Additional chemotherapeutic agents useful in combination with the present compounds include proteasome inhibitors, such as bortezomib, carfilzomib, marizomib and the like.

Examples of kinase inhibitors that are useful in combination with the presently disclosed compounds, particularly in treating malignancies include: Btk inhibitors, such as ibrutinib; CDK inhibitors, such as palbociclib; EGFR inhibitors, such as afatinib, erlotinib, gefitinib, lapatinib, osimertinib and vandetinib; Mek inhibitors, such as trametinib; Raf inhibitors, such as dabrafenib, sorafenib and vemurafenib; VEGFR inhibitors, such as axitinib, lenvatinib, nintedanib, pazopanib; BCR-Abl inhibitors, such as bosutinib, dasatinib, imatinib and nilotinib; FLT-3 inhibitors, such as gilteritinib and quizartinib, PI3-kinase inhibitors, such as idelalisib, Syk inhibitors, such as fostamatinib; and JAK inhibitors, such as ruxolitinib and fedratinib.

In other embodiments, the second therapeutic agent may be selected from any of the following:

analgesics-morphine, fentanyl, hydromorphone, oxycodone, codeine, acetaminophen, hydrocodone, buprenorphine, tramadol, venlafaxine, flupirtine, meperidine, pentazocine, dextromoramide, dipipanone;

antibiotics-aminoglycosides (e.g., amikacin, gentamicin, kanamycin, neomycin, netilmicin, tobramycin, and paromycin), carbapenems (e.g., ertapenem, doripenem, imipenem, cilastatin, and meropenem), cephalosporins (e.g., cefadroxil, cefazolin, cefalotin, cephalexin, cefaclor, cefamandole, cefoxitin, cefprozil, cefuroxime, cefixime, cefdinir, cefditoren, cefoperazone, cefotaxime, cefpodoxime, ceftazidime, ceftibuten, ceftizoxime, ceftriaxone, cefepime, and cefobiprole), glycopeptides (e.g., teicoplanin, vancomycin, and telavancin), lincosamides (e.g., clindamycin and incomysin), lipopeptides (e.g., daptomycin), macrolides (azithromycin, clarithromycin, dirithromycin, erythromycin, roxithromycin, troleandomycin, telithromycin, and spectinomycin), monobactams (e.g., aztreonam), nitrofurans (e.g., furazolidone and nitrofurantoin), penicilllins (e.g., amoxicillin, ampicillin, azlocillin, carbenicillin, cloxacillin, dicloxacillin, flucloxacillin, mezlocillin, methicillin, nafcillin, oxacillin, penicillin G, penicillin V, piperacillin, temocillin, and ticarcillin), penicillin combinations (e.g., amoxicillin/clavulanate, ampicillin/sulbactam, piperacillin/tazobactam, and ticarcillin/clavulanate), polypeptides (e.g., bacitracin, colistin, and polymyxin B), quinolones (e.g., ciprofloxacin, enoxacin, gatifloxacin, levofloxacin, lomefloxacin, moxifloxacin, nalidixic acid, norfloxacin, ofloxacin, trovafloxacin, grepafloxacin, sparfloxacin, and temafloxacin), sulfonamides (e.g., mafenide, sulfonamidochrysoidine, sulfacetamide, sulfadiazine, silver sulfadiazine, sulfamethizole, sulfamethoxazole, sulfanilimide, sulfasalazine, sulfisoxazole, trimethoprim, and trimethoprim-sulfamethoxazole), tetracyclines (e.g., demeclocycline, doxycycline, minocycline, oxytetracycline, and tetracycline), antimycobacterial compounds (e.g., clofazimine, dapsone, capreomycin, cycloserine, ethambutol, ethionamide, isoniazid, pyrazinamide, rifampicin (rifampin), rifabutin, rifapentine, and streptomycin), and others, such as arsphenamine, chloramphenicol, fosfomycin, fusidic acid, linezolid, metronidazole, mupirocin, platensimycin, quinuprisin/dalfopristin, rifaximin, thiamphenicol, tigecycline, and timidazole;

antibodies-anti-TNF-α antibodies, e.g., infliximab (Remicade™), adalimumab, golimumab, certolizumab; anti-B cell antibodies, e.g., rituximab; anti-IL-6 antibodies, e.g., tocilizumab; anti-IL-1 antibodies, e.g., anakinra; anti PD-1 and/or anti-PD-L1 antibodies, e.g. nivolumab, pembrolizumab, pidilizumab, BMS-936559, MPDL3280A, AMP-224, MEDI4736; ixekizumab, brodalumab, ofatumumab, sirukumab, clenoliximab, clazakiumab, fezakinumab, fletikumab, mavrilimumab, ocrelizumab, sarilumab, secukinumab, toralizumab, zanolimumab;

anticoagulants-warfarin (Coumadin™), acenocoumarol, phenprocoumon, atromentin, phenindione, heparin, fondaparinux, idraparinux, rivaroxaban, apixaban, hirudin, lepirudin, bivalirudin, argatroban, dabigatran, ximelagatran, batroxobin, hementin;

anti-inflammatory agents-steroids, e.g., budesonide, non-steroidal anti-inflammatory agents, e.g., aminosalicylates (e.g., sulfasalazine, mesalamine, olsalazine, and balsalazide), cyclooxygenase inhibitors (COX-2 inhibitors, such as rofecoxib, celecoxib), diclofenac, etodolac, famotidine, fenoprofen, flurbiprofen, ketoprofen, ketorolac, ibuprofen, indomethacin, meclofenamate, mefenamic acid, meloxicam, nambumetone, naproxen, oxaprozin, piroxicam, salsalate, sulindac, tolmetin;

immunosuppressants-mercaptopurine, corticosteroids such as dexamethasone, hydrocortisone, prednisone, methylprednisolone and prednisolone, alkylating agents such as cyclophosphamide, calcineurin inhibitors such as cyclosporine, sirolimus and tacrolimus, inhibitors of inosine monophosphate dehydrogenase (IMPDH) such as mycophenolate, mycophenolate mofetil and azathioprine, and agents designed to suppress cellular immunity while leaving the recipient's humoral immunologic response intact, including various antibodies (for example, antilymphocyte globulin (ALG), antithymocyte globulin (ATG), monoclonal anti-T-cell antibodies (OKT3)) and irradiation. Azathioprine is currently available from Salix Pharmaceuticals, Inc. under the brand name Azasan; mercaptopurine is currently available from Gate Pharmaceuticals, Inc. under the brand name Purinethol; prednisone and prednisolone are currently available from Roxane Laboratories, Inc.; Methyl prednisolone is currently available from Pfizer; sirolimus (rapamycin) is currently available from Wyeth-Ayerst under the brand name Rapamune; tacrolimus is currently available from Fujisawa under the brand name Prograf; cyclosporine is current available from Novartis under the brand name Sandimmune and Abbott under the brand name Gengraf; EMIPDH inhibitors such as mycophenolate mofetil and mycophenolic acid are currently available from Roche under the brand name Cellcept and Novartis under the brand name Myfortic; azathioprine is currently available from Glaxo Smith Kline under the brand name Imuran; and antibodies are currently available from Ortho Biotech under the brand name Orthoclone, Novartis under the brand name Simulect (basiliximab) and Roche under the brand name Zenapax (daclizumab); and Guanylate cyclase-C receptor agonists or intestinal secretagogues, for example linaclotide, sold under the name Linzess.

These various agents can be used in accordance with their standard or common dosages, as specified in the prescribing information accompanying commercially available forms of the drugs (see also, the prescribing information in the 2006 Edition of The Physician's Desk Reference), the disclosures of which are incorporated herein by reference.

IV. METHODS FOR MAKING COMPOUNDS

The disclosed compounds can be prepared by any suitable method as will be understood by a person of ordinary skill in the art. An overview for assembly of the tricyclic core moieties of the present compounds is provided in Scheme 1 below.

Scheme 1: Construction of tricyclic cores
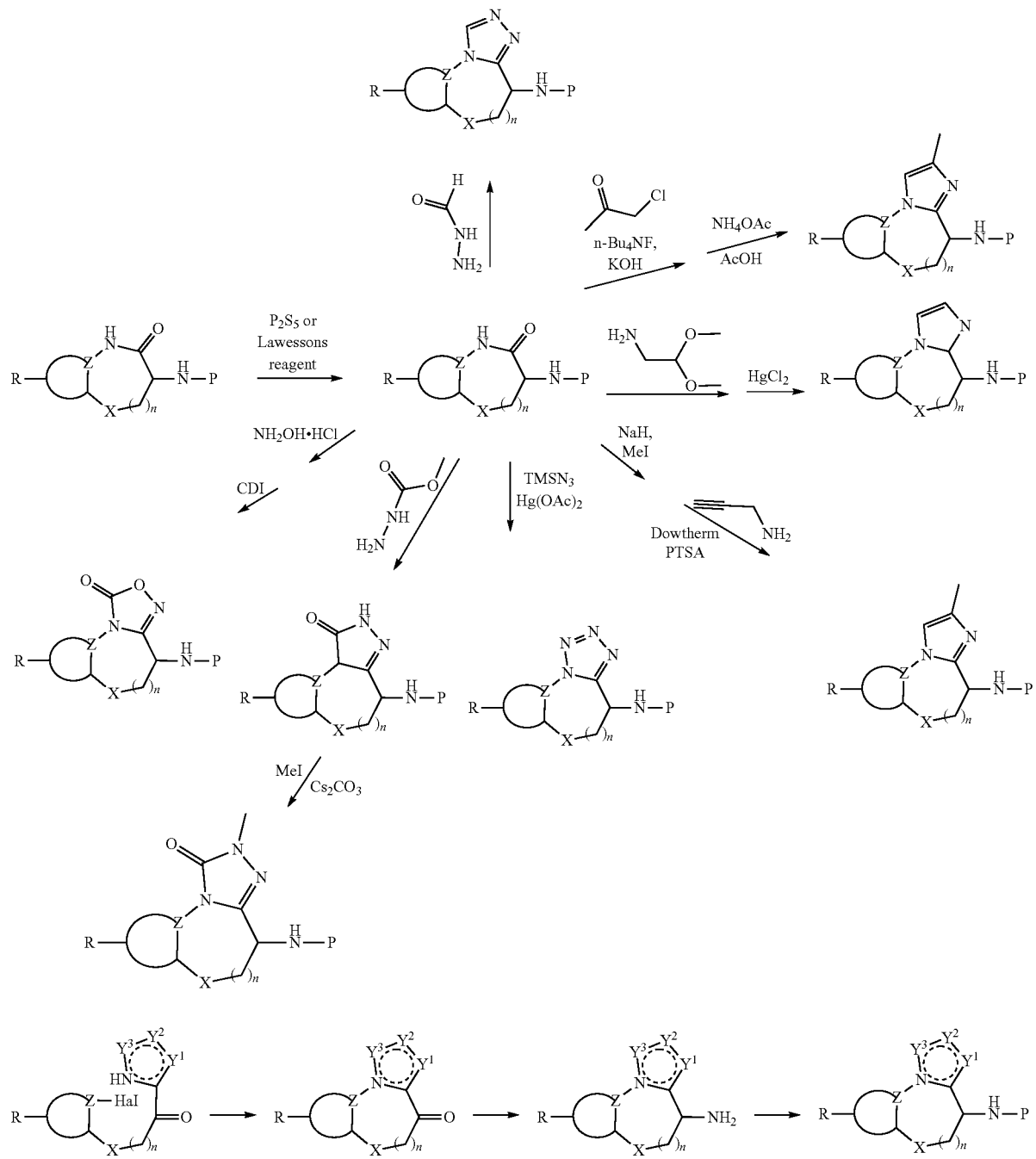
Scheme 2 provides another overview of methods for synthesizing RIP1K inhibitory compounds disclosed herein.
Scheme 2: General methods for forming tricyclic rings
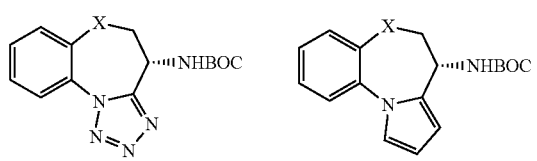

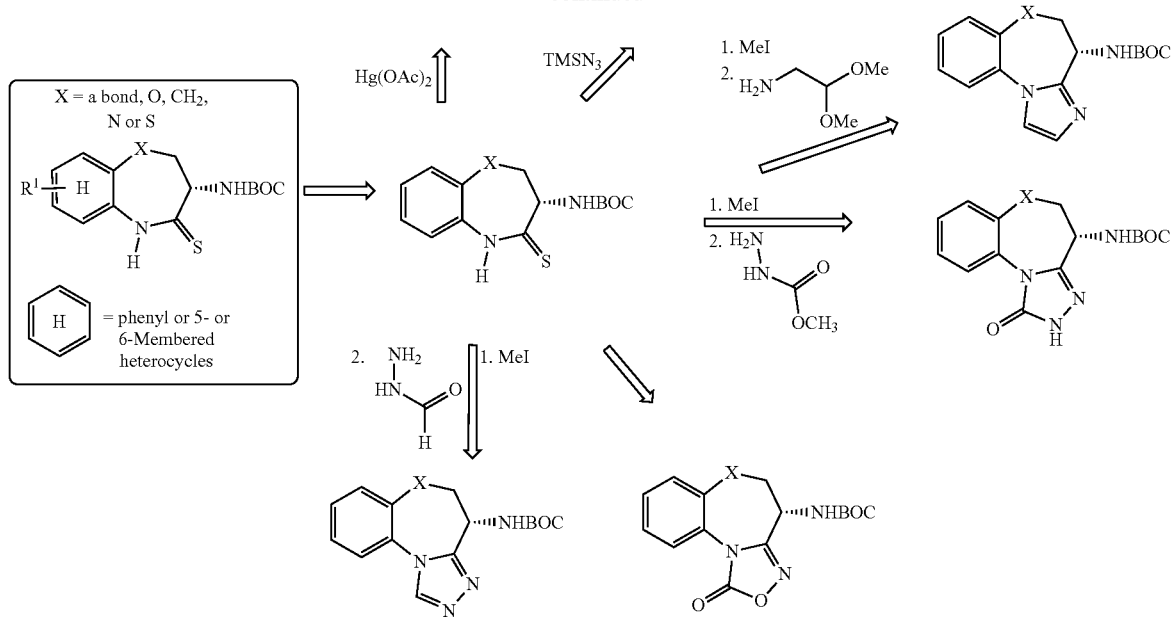
Scheme 3 provides an overview of methods for functionalizing the tricyclic intermediates described herein. Such methods can be used to introduce $R^1$ moieties, the B ring, and the $R^3$, L and W groups described herein.

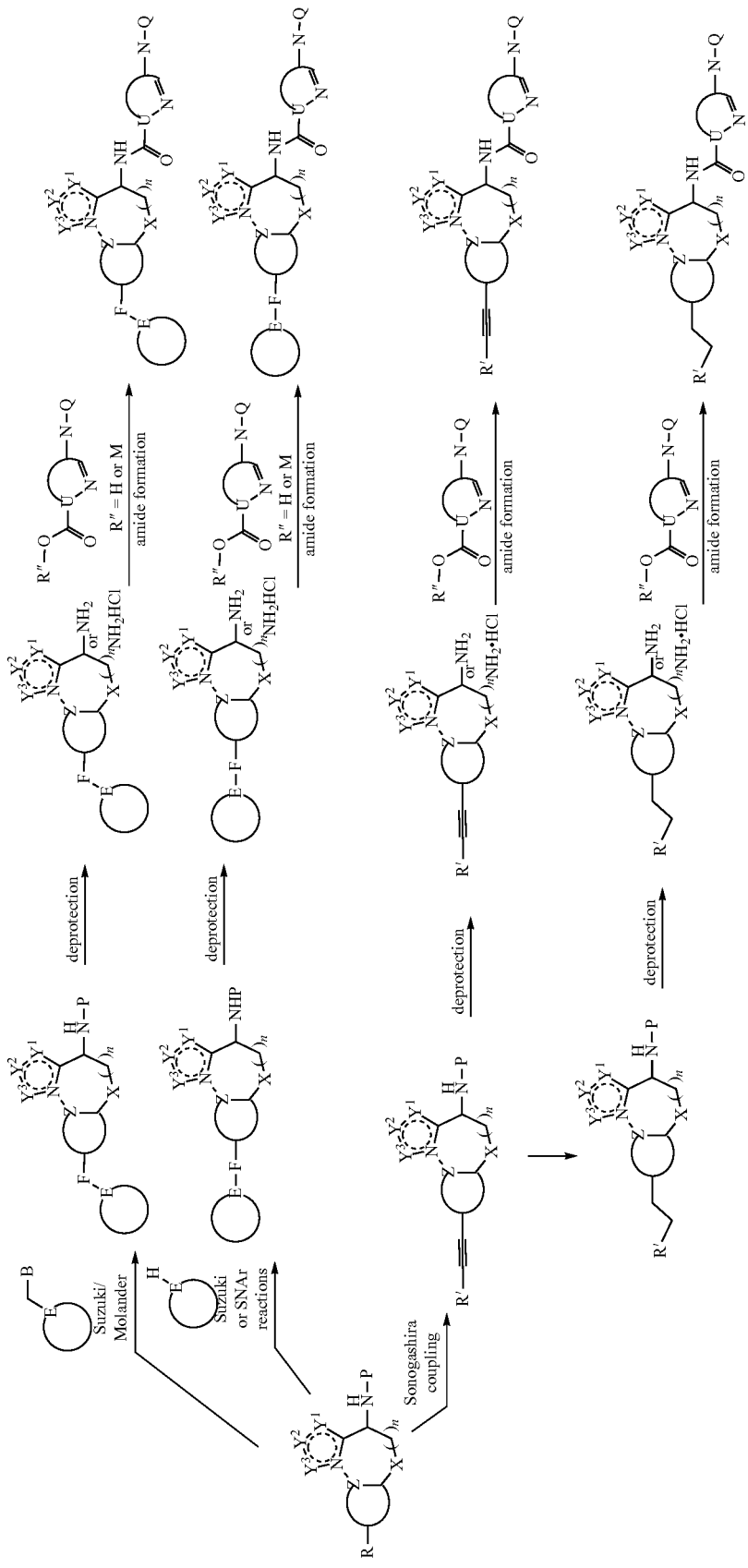

One exemplary suitable method is provided below with reference to specific compounds in the examples, is set forth in Scheme 4. This example provides a general method for linking the tricyclic core molecule (prepared as set forth in Scheme 1) to the B ring set forth in Formula I.

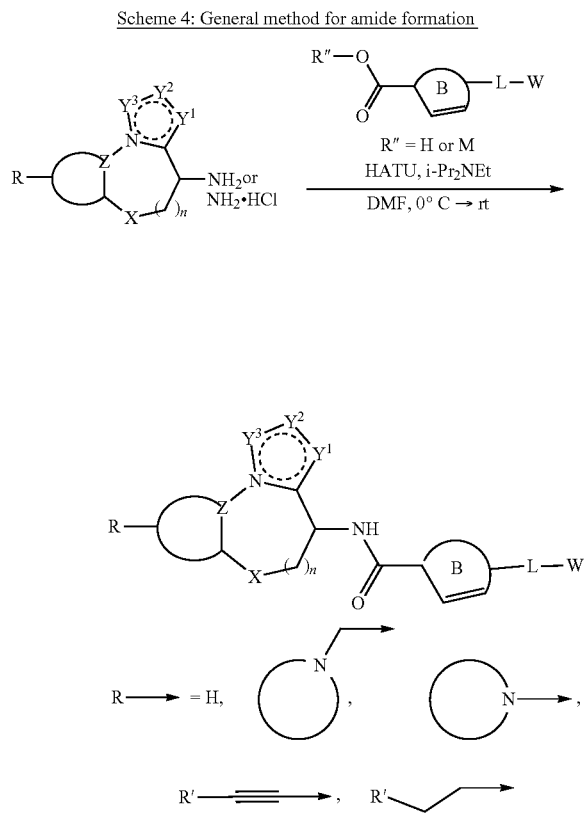

With reference to Scheme 4, a stirring mixture of amine/amine hydrochloride (1 eq), aryl/heteroaryl acid/salt (1.2 eq) and HATU (1.3-1.4 eq) in dry DMF (0.3-0.8 mL/0.1 mmol) was degassed under vacuum and back filled with argon. After three degassing cycles, i-Pr$_2$NEt (4-7 eq) was added to the above stirring mixture at either 0° C. or room temperature and stirred till the consumption of amine. The reaction solution was processed in one of the methods such as a) the usual extractive work-up with either EtOAc or CH$_2$Cl$_2$, after diluting with ice-water (b) usual work-up after reaction solution concentration to dryness or c) crude concentrate was diluted with ice-water, sonicated, allowed the slurry warm to room temperature and filtered to obtain crude grey/dark solid after suction drying. Purification of the crude material from any of the processing methods by either normal phase silica gel or reverse phase chromatography provided the respective amide compounds. (Yield: 31-82%).

With reference to Schemes 1, 2, 3 and 4, the variables X, Y$^1$, Y$^2$, Y$^3$ and Z are as hereinbefore described; P is a protecting group as is known to those of skill in the art and as further exemplified herein. R is one or more of any suitable substituent as is known to those of skill in the art, such an R$^1$ moiety described herein or a precursor thereto.

Scheme 5 describes a method for halogenating certain intermediate compounds to produce RIP1K inhibitors described herein.

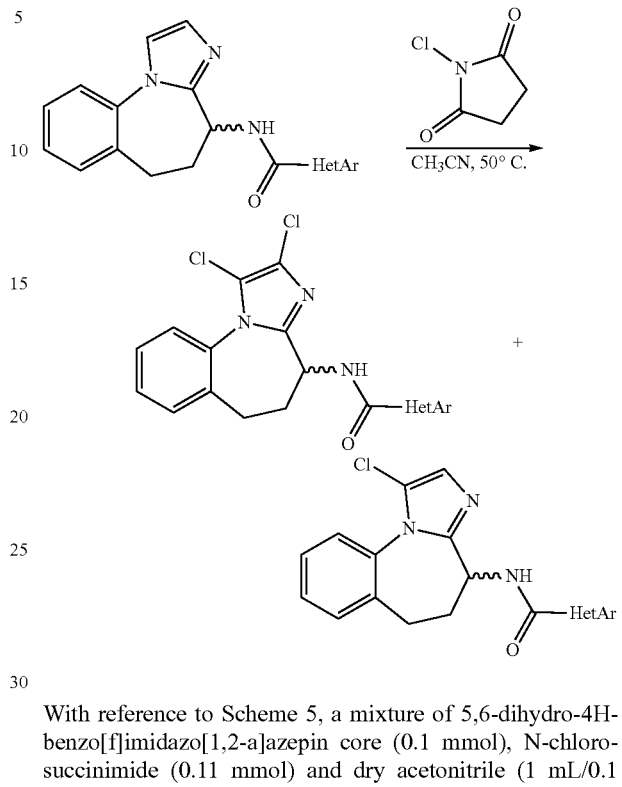

With reference to Scheme 5, a mixture of 5,6-dihydro-4H-benzo[f]imidazo[1,2-a]azepin core (0.1 mmol), N-chlorosuccinimide (0.11 mmol) and dry acetonitrile (1 mL/0.1 mmol)) was stirred at 50° C. overnight, diluted with water and filtered. The solid on the funnel upon drying dissolved in CH$_2$Cl$_2$ and loaded onto a silica gel column. Flash silica gel column chromatographic purification provided dichloro-substituted compound (fast eluting) and monochloro-substituted compound (slow eluting) respectively.

The following compounds were synthesized using the methods disclosed herein and those known to those of ordinary skill in the art of organic synthesis and medicinal chemistry.

I-1 (±)-5-Benzyl-N-(5,6-dihydro-4H-benzo[f]imidazo[1,2-a]azepin-4-yl)-1H-1,2,4-triazole-3-carboxamide

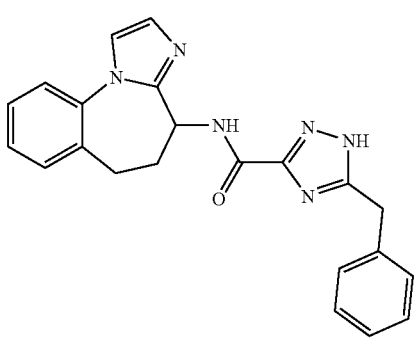 [SMILES: O=C(NC1CCc2ccccc2-n2ccnc21)c1n[nH]c(Cc2ccccc2)n1]

$^1$H NMR (400 MHz, Chloroform-d) δ 7.94 (d, J=9.0 Hz, 1H), 7.45-7.17 (m, 9H), 7.11 (d, J=1.4 Hz, 1H), 6.70 (s, 1H), 5.32-5.21 (m, 1H), 4.11 (s, 2H), 2.76-2.66 (m, 2H), 2.58-

2.48 (m, 1H), 2.22 (td, J=11.7, 7.6 Hz, 1H). LCMS: Purity 95%, MS (m/e) 385 (M+H)⁺.

I-2 (±)—N-(5,6-Dihydro-4H-benzo[f]imidazo[1,2-a]azepin-4-yl)-4-phenylpyrimidine-2-carboxamide

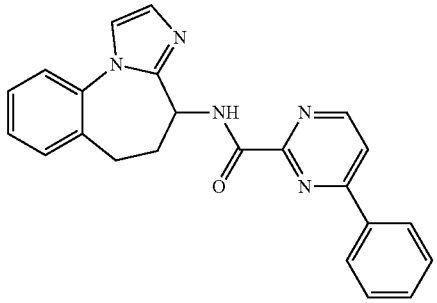 [SMILES: O=C(NC1CCc2ccccc2-n2ccnc21)c1nccc(-c2ccccc2)n1]

$^1$H NMR (400 MHz, Chloroform-d) δ 9.44 (d, J=7.5 Hz, 1H), 8.93 (d, J=5.3 Hz, 1H), 8.25-8.16 (m, 2H), 7.81 (d, J=5.3 Hz, 1H), 7.62-7.50 (m, 3H), 7.44-7.29 (m, 4H), 7.23 (d, J=1.4 Hz, 1H), 7.18 (d, J=1.4 Hz, 1H), 5.22 (dt, J=10.2, 7.7 Hz, 1H), 3.19-3.05 (m, 1H), 2.74 (ddd, J=14.0, 6.7, 2.0 Hz, 1H), 2.64 (td, J=13.1, 7.4 Hz, 1H), 2.27-2.14 (m, 1H). LCMS: Purity 99%, MS (m/e) 382 (M+H)⁺.

I-7 (±)-1-(2,6-dichlorobenzyl)-N-(5,6-dihydro-4H-benzo[f]imidazo[1,2-a]azepin-4-yl)-1H-1,2,4-triazole-3-carboxamide

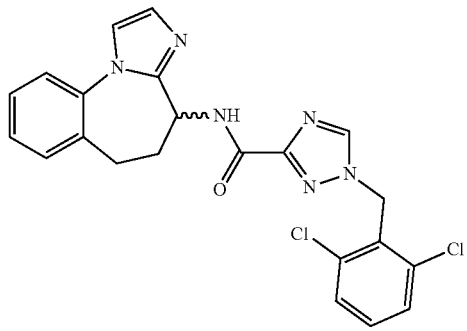

$^1$H NMR (400 MHz, Chloroform-d) δ 8.44 (d, J=7.7 Hz, 1H), 7.95 (s, 1H), 7.46-7.27 (m, 7H), 7.20 (d, J=1.4 Hz, 1H), 7.15 (d, J=1.4 Hz, 1H), 5.71 (s, 2H), 5.15 (dt, J=10.5, 7.7 Hz, 1H), 3.10-2.95 (m, 1H), 2.73-2.56 (m, 2H), 2.17 (app td, J=11.1, 7.2 Hz, 1H). LCMS: Purity 98%, MS (m/e) 454 (M+H)⁺.

I-6 (±)-1-(2,6-Dichlorobenzyl)-N-(5,6-dihydro-4H-benzo[f]imidazo[1,2-a]azepin-4-yl)-1H-1,2,4-triazole-5-carboxamide

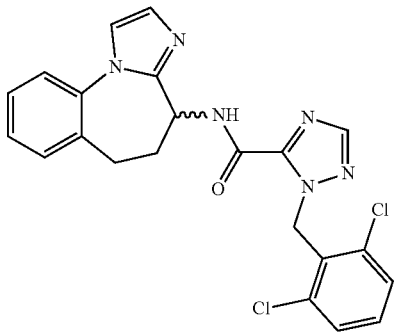 [SMILES: O=C(NC1CCc2ccccc2-n2ccnc21)c1ncnn1Cc1c(Cl)cccc1Cl]

$^1$H NMR (400 MHz, Chloroform-d) δ 8.69 (d, J=7.5 Hz, 1H), 7.84 (s, 1H), 7.44-7.30 (m, 6H), 7.28-7.19 (m, 2H), 7.17 (d, J=1.4 Hz, 1H), 6.15 (app q, J=17.7 Hz, 2H), 5.10 (dt, J=10.4, 7.6 Hz, 1H), 3.02 (tt, J=12.6, 7.2 Hz, 1H), 2.82-2.58 (m, 2H), 2.28-2.16 (m, 1H). LCMS: Purity 98%, MS (m/e) 454 (M+H)⁺.

I-9 (±)-5-Benzyl-N-(5,6-dihydro-4H-benzo[f]imidazo[1,2-a]azepin-4-yl)isoxazole-3-carboxamide

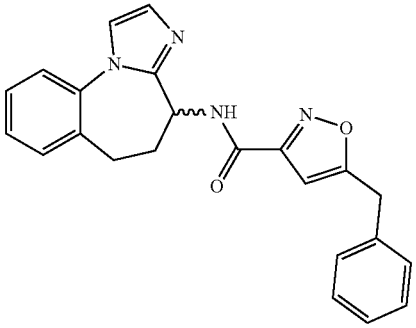 [SMILES: O=C(NC1CCc2ccccc2-n2ccnc21)c1cc(Cc2ccccc2)on1]

$^1$H NMR (400 MHz, Chloroform-d) δ 8.10 (d, J=7.4 Hz, 1H), 7.41-7.25 (m, 8H), 7.25-7.21 (m, 2H), 7.19 (d, J=1.4 Hz, 1H), 7.13 (d, J=1.4 Hz, 1H), 6.33 (t, J=0.8 Hz, 1H), 5.06 (dt, J=10.3, 7.6 Hz, 1H), 4.11 (s, 2H), 2.97 (tdd, J=12.7, 7.8, 6.8 Hz, 1H), 2.70 (ddd, J=14.0, 6.8, 1.8 Hz, 1H), 2.60 (td, J=13.2, 7.5 Hz, 1H), 2.19-2.09 (m, 1H). LCMS: Purity 98%, MS (m/e) 385 (M+H)⁺.

I-14 (±)—N-(5,6-Dihydro-4H-benzo[f]imidazo[1,2-a]azepin-4-yl)-1-(2-fluorobenzyl)-1H-1,2,4-triazole-3-carboxamide

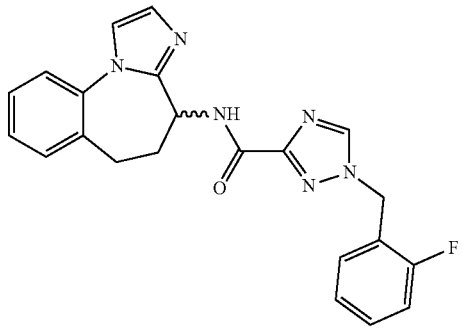 [SMILES: O=C(NC1CCc2ccccc2-n2ccnc21)c1ncn(Cc2ccccc2F)n1]

LCMS: Purity 98%, MS (m/e) 403(M+H)⁺.

I-19 (±)-5-(2,6-Dichlorobenzyl)-N-(5,6-dihydro-4H-benzo[f]imidazo[1,2-a]azepin-4-yl)-1H-1,2,4-triazole-3-carboxamide

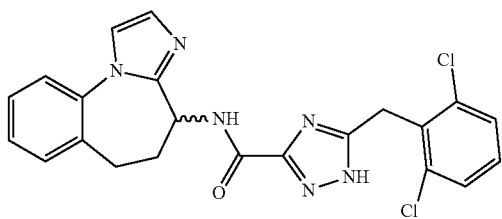 [SMILES: O=C(NC1CCc2ccccc2-n2ccnc21)c1n[nH]c(Cc2c(Cl)cccc2Cl)n1]

¹H NMR (400 MHz, Chloroform-d) δ 8.03 (br s, 1H), 7.44-7.29 (m, 6H), 7.19-7.10 (m, 2H), 6.91 (s, 1H), 5.14 (dt, J=10.7, 8.0 Hz, 1H), 4.48 (s, 2H), 2.87-2.71 (m, 2H), 2.57 (app td, J=13.2, 7.3 Hz, 1H), 2.32-2.22 (m, 1H). LCMS: Purity 98%, MS (m/e) 454 (M+H)⁺.

I-27 (±)-1-(2,6-Dichlorobenzyl)-N-(6,7-dihydrobenzo[b]pyrrolo[1,2-d][1,4]oxazepin-7-yl)-1H-1,2,4-triazole-3-carboxamide

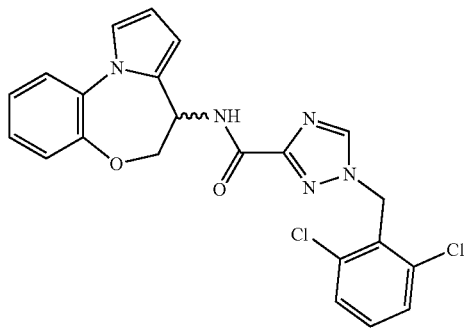 [SMILES: O=C(NC1COc2ccccc2-n2cccc21)c1ncn(Cc2c(Cl)cccc2Cl)n1]

¹H NMR (400 MHz, Chloroform-d) δ 7.93 (d, J=0.6 Hz, 1H), 7.43-7.16 (m, 8H), 7.00 (t, J=2.3 Hz, 1H), 6.28 (d, J=2.3 Hz, 2H), 5.66 (s, 2H), 5.62 (ddd, J=9.1, 6.7, 6.0 Hz, 1H), 4.68 (dd, J=10.8, 6.0 Hz, 1H), 4.35 (dd, J=10.8, 6.8 Hz, 1H). LCMS: Purity 99%, MS (m/e) 455 (M+H)⁺.

I-29 (±)-1-(2,6-Dichlorobenzyl)-N-(4,5-dihydroimidazo[1,2-d]pyrrolo[2,1-b][1,3,4]thiadiazepin-4-yl)-1H-1,2,4-triazole-3-carboxamide

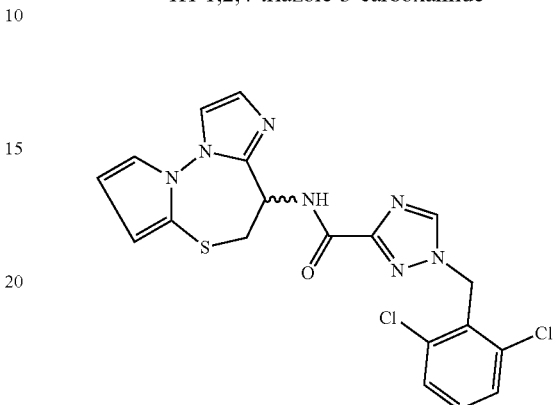

¹H NMR (400 MHz, Chloroform-d) δ 8.38 (d, J=7.9 Hz, 1H), 7.96 (s, 1H), 7.43 (d, J=1.2 Hz, 1H), 7.41 (s, 1H), 7.33 (dd, J=8.9, 7.1 Hz, 1H), 7.27 (d, J=1.5 Hz, 1H), 7.16 (d, J=1.5 Hz, 1H), 7.11 (dd, J=3.2, 1.7 Hz, 1H), 6.52 (dd, J=4.0, 1.7 Hz, 1H), 6.31 (dd, J=4.0, 3.2 Hz, 1H), 5.71 (s, 2H), 5.22 (ddd, J=10.2, 7.9, 6.7 Hz, 1H), 3.97 (dd, J=11.4, 6.7 Hz, 1H), 2.76 (dd, J=11.4, 10.2 Hz, 1H). LCMS: Purity 99%, MS (m/e) 461 (M+H)⁺.

I-34 (±)-5-Benzyl-N-(6,7-dihydrobenzo[b]pyrrolo[1,2-d][1,4]oxazepin-7-yl)-1H-1,2,4-triazole-3-carboxamide

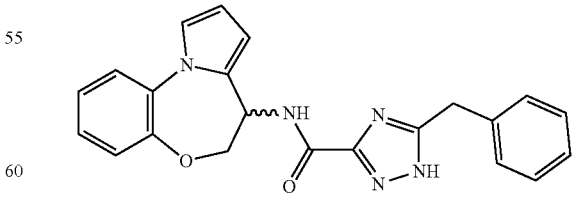

¹H NMR (400 MHz, Chloroform-d) δ 11.86 (s, 1H), 7.47-7.35 (m, 2H), 7.34-7.18 (m, 8H), 7.02 (t, J=2.3 Hz, 1H), 6.33-6.26 (app m, 2H), 5.58 (dt, J=8.9, 6.4 Hz, 1H), 4.65 (dd, J=10.9, 6.0 Hz, 1H), 4.36 (dd, J=10.9, 6.9 Hz, 1H), 4.14 (s, 2H). LCMS: Purity 96%, MS (m/e) 386 (M+H)⁺.

I-35 (±)-1-(2,6-Dichlorobenzyl)-N-(2-methyl-5,6-dihydro-4H-benzo[f]imidazo[1,2-a]azepin-4-yl)-1H-1,2,4-triazole-3-carboxamide

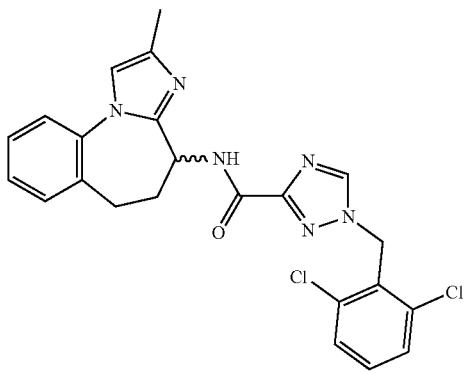 [SMILES: Cc1cn2c(n1)C(NC(=O)c1ncn(Cc3c(Cl)cccc3Cl)n1)CCc1ccccc1-2]

¹H NMR (400 MHz, Chloroform-d) δ 8.41 (d, J=7.5 Hz, 1H), 7.96 (d, J=0.7 Hz, 1H), 7.47-7.20 (m, 7H), 6.90 (q, J=1.0 Hz, 1H), 5.71 (app s, 2H), 5.09 (dt, J=10.4, 7.6 Hz, 1H), 3.03 (tt, J=12.6, 7.3 Hz, 1H), 2.72-2.54 (m, 2H), 2.30 (d, J=1.0 Hz, 3H), 2.18-2.05 (m, 1H). LCMS: Purity 95%, MS (m/e) 468 (M+H)⁺.

I-36 (±)-1-(2,6-Dichlorobenzyl)-N-(1-oxo-2,4,5,6-tetrahydro-1H-benzo[f][1,2,4]triazolo[4,3-a]azepin-4-yl)-1H-1,2,4-triazole-3-carboxamide

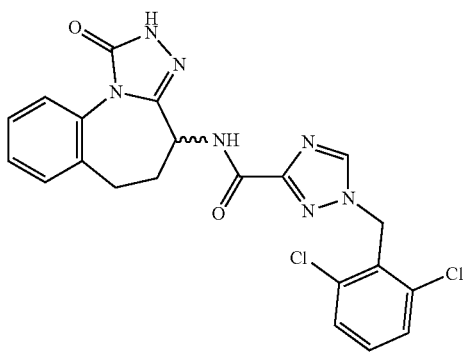 [SMILES: O=C(NC1CCc2ccccc2-n2c1n[nH]c2=O)c1ncn(Cc2c(Cl)cccc2Cl)n1]

¹H NMR (400 MHz, Methanol-d₄) δ 8.53 (s, 1H), 7.58 (dd, J=8.0, 1.4 Hz, 1H), 7.53-7.34 (m, 7H), 5.79 (s, 2H), 4.89 (dd, J=10.3, 8.0 Hz, 1H), 2.89-2.68 (m, 2H), 2.66-2.51 (m, 1H), 2.37-2.25 (m, 1H). Purity 95%, MS (m/e) 471 (M+H)⁺.

I-37 (±)—N-(6,7-Dihydrobenzo[b]pyrrolo[1,2-d][1,4]oxazepin-7-yl)-5-(4-fluorobenzyl)-1H-1,2,4-triazole-3-carboxamide

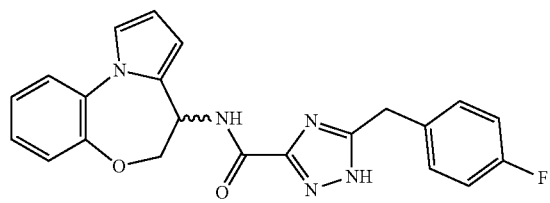 [SMILES: O=C(NC1COc2ccccc2-n2cccc21)c1n[nH]c(Cc2ccc(F)cc2)n1]

¹H NMR (400 MHz, Chloroform-d) δ 13.40 (br s, 1H), 7.50 (d, J=9.0 Hz, 1H), 7.44-7.36 (m, 1H), 7.30-7.17 (m, 3H), 7.17 (dd, J=8.6, 5.4 Hz, 2H), 7.02 (dd, J=2.9, 1.7 Hz, 1H), 6.91 (t, J=8.6 Hz, 2H), 6.32-6.23 (m, 2H), 5.55 (dt, J=9.0, 6.4 Hz, 1H), 4.63 (dd, J=10.9, 6.0 Hz, 1H), 4.36 (dd, J=10.9, 6.8 Hz, 1H), 4.12 (s, 2H). ¹⁹F NMR (376 MHz, Chloroform-d) δ −115.74. Purity 98%, MS (m/e) 404 (M+H)⁺.

I-38 (±)—N-(6,7-Dihydrobenzo[b]pyrrolo[1,2-d][1,4]oxazepin-7-yl)-1-(2-fluorobenzyl)-1H-1,2,4-triazole-3-carboxamide

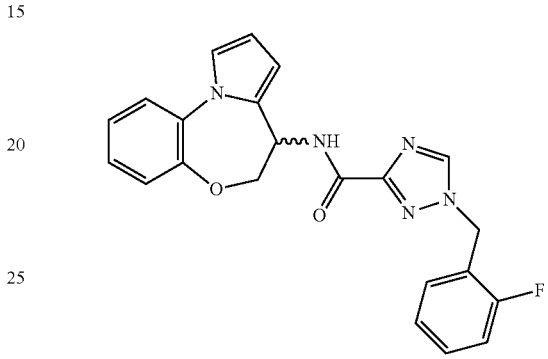

¹H NMR (400 MHz, Chloroform-d) δ 8.06 (d, J=0.9 Hz, 1H), 7.45-7.32 (m, 3H), 7.37-7.29 (m, 1H), 7.28-7.19 (m, 3H), 7.23-7.06 (m, 2H), 7.01 (t, J=2.3 Hz, 1H), 6.29 (app d, J=2.4 Hz, 2H), 5.63 (ddd, J=9.1, 6.9, 6.0 Hz, 1H), 5.41 (app d, J=1.2 Hz, 2H), 4.68 (dd, J=10.8, 6.0 Hz, 1H), 4.35 (dd, J=10.8, 6.9 Hz, 1H). ¹⁹F NMR (376 MHz, Chloroform-d) δ −118.06--118.09 (m). Purity 97%, MS (m/e) 404 (M+H)⁺.

I-39 (±)-5-Benzyl-N-(9-((4-(pyridin-4-yl)piperazin-1-yl)methyl)-5,6-dihydro-4H-benzo[f]imidazo[1,2-a]azepin-4-yl)-1H-1,2,4-triazole-3-carboxamide

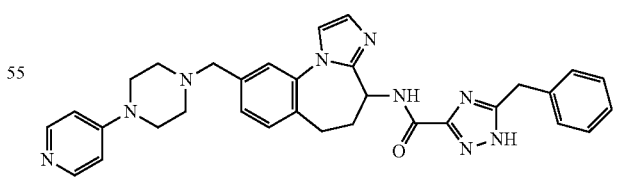

¹H NMR (400 MHz, Methanol-d₄) δ 8.10-8.06 (m, 2H), 7.47 (d, J=1.6 Hz, 1H), 7.44-7.36 (m, 3H), 7.33-7.19 (m, 5H), 7.03 (d, J=1.5 Hz, 1H), 6.85-6.80 (m, 2H), 5.03 (dd, J=10.6, 7.5 Hz, 1H), 4.14 (s, 4H), 3.62 (app q, J=17.3 Hz, 2H), 3.41 (app t, J=5.2 Hz, 4H), 2.82-2.74 (m, 1H), 2.74-2.62 (m, 1H), 2.59 (app t, J=5.2 Hz, 4H), 2.56-2.47 (m, 1H), 2.37-2.32 9 (m, 1H). Purity 96%, MS (m/e) 560 (M+H)⁺.

I-40 (±)-5-Benzyl-N-(1-methyl-5,6-dihydro-4H-benzo[f]imidazo[1,2-a]azepin-4-yl)-1H-1,2,4-triazole-3-carboxamide

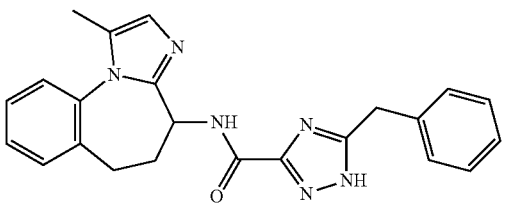 [SMILES: Cc1cnc2n1-c1ccccc1CCC2NC(=O)c1n[nH]c(Cc2ccccc2)n1]

¹H NMR (400 MHz, Methanol-d₄) δ 7.50-7.43 (m, 2H), 7.43-7.35 (m, 2H), 7.33-7.17 (m, 5H), 6.77 (q, J=1.0 Hz, 1H), 4.88 (dd, J=11.2, 7.5 Hz, 1H), 4.14 (s, 2H), 2.73 (dd, J=13.4, 6.2 Hz, 1H), 2.63-2.53 (m, 1H), 2.43-2.34 (m, 1H), 2.27-2.19 (m, 1H), 2.22 (d, J=1.1 Hz, 3H). Purity 95%, MS (m/e) 399 (M+H)⁺.

I-44 (±)-1-(2,6-Dichlorobenzyl)-N-(1-methyl-5,6-dihydro-4H-benzo[f]imidazo[1,2-a]azepin-4-yl)-1H-1,2,4-triazole-3-carboxamide

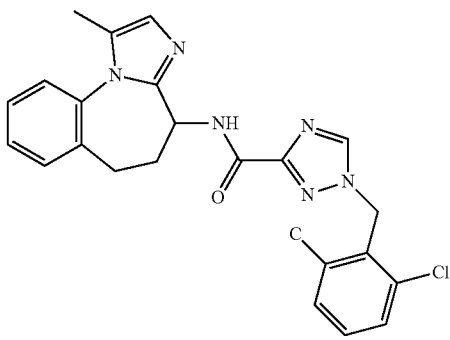 [SMILES: Cc1cccc(Cl)c1Cn1cnc(C(=O)NC2CCc3ccccc3-n3c(C)cnc32)n1]

¹H NMR (400 MHz, Chloroform-d) δ 8.49-8.42 (app m, 1H), 7.91 (s, 1H), 7.44-7.26 (m, 6H), 7.24-7.17 (m, 1H), 6.85 (t, J=1.1 Hz, 1H), 5.69 (s, 2H), 5.06-4.95 (m, 1H), 3.01-2.87 (m, 1H), 2.67-2.57 (m, 1H), 2.48-2.44 (m, 1H), 2.23 (d, J=1.1 Hz, 3H), 2.10-1.97 (m, 1H). Purity 92%, MS (m/e) 468 (M+H)⁺.

I-45 (±)-5-Benzyl-N-(4,5-dihydroimidazo[1,2-d]pyrrolo[2,1-b][1,3,4]thiadiazepin-4-yl)-1H-1,2,4-triazole-3-carboxamide

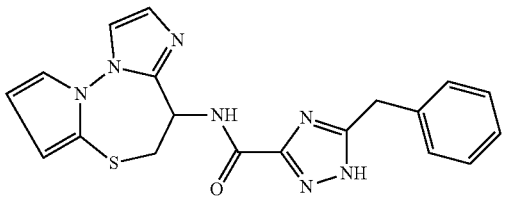 [SMILES: O=C(NC1CSc2cccn2-n2ccnc21)c1n[nH]c(Cc2ccccc2)n1]

¹H NMR (400 MHz, Chloroform-d) δ 9.09 (s, 1H), 7.35-7.20 (m, 6H), 7.18 (d, J=1.6 Hz, 1H), 7.15 (dd, J=3.3, 1.7 Hz, 1H), 6.63 (s, 1H), 6.50 (dd, J=4.0, 1.7 Hz, 1H), 6.31 (dd, J=4.0, 3.2 Hz, 1H), 5.29 (q, J=9.1 Hz, 1H), 4.18 (s, 2H), 3.74 (dd, J=11.3, 6.7 Hz, 1H), 2.80 (t, J=11.2 Hz, 1H). Purity 96%, MS (m/e) 392 (M+H)⁺.

I-47 (±)-1-(2,6-Dichlorobenzyl)-N-(9-((4-(pyridin-4-yl)piperazin-1-yl)methyl)-5,6-dihydro-4H-benzo[f]imidazo[1,2-a]azepin-4-yl)-1H-1,2,4-triazole-3-carboxamide

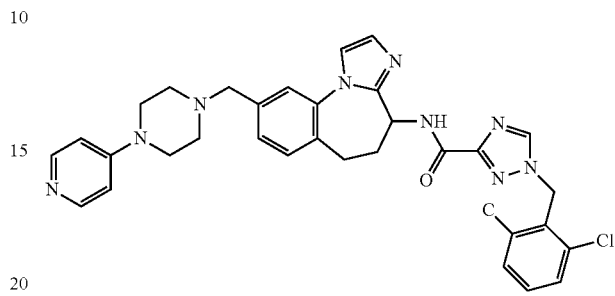

¹H NMR (400 MHz, Chloroform-d) δ 8.44 (d, J=7.7 Hz, 1H), 8.28-8.21 (m, 2H), 7.93 (d, J=0.6 Hz, 1H), 7.41 (dd, J=8.0, 0.9 Hz, 2H), 7.36-7.24 (m, 4H), 7.19 (d, J=1.4 Hz, 1H), 7.12 (d, J=1.4 Hz, 1H), 6.67-6.60 (m, 2H), 5.70 (s, 2H), 5.15 (dt, J=10.5, 7.8 Hz, 1H), 3.63-3.50 (m, 2H), 3.39-3.31 (m, 4H), 3.07-2.92 (m, 1H), 2.68 (dd, J=13.9, 6.4 Hz, 1H), 2.62-2.52 (m, 5H), 2.12-2.08 (m, 1H). Purity 97%, MS (m/e) 629 (M+H)⁺.

R955314 (±)-5-Benzyl-N-(1-oxo-5,6-dihydro-1H,4H-benzo[f][1,2,4]oxadiazolo[4,3-a]azepin-4-yl)-1H-1,2,4-triazole-3-carboxamide

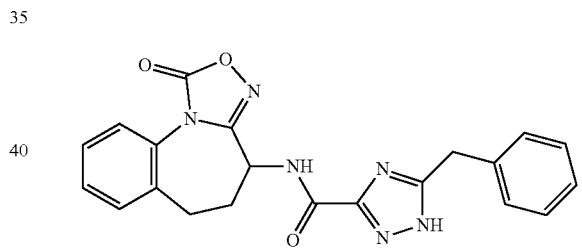

¹H NMR (400 MHz, Methanol-d₄) δ 7.58 (dd, J=7.9, 1.4 Hz, 1H), 7.50-7.36 (m, 3H), 7.36-7.16 (m, 5H), 4.94 (dd, J=10.4, 8.3 Hz, 1H), 4.15 (s, 2H), 2.91-2.84 (m, 2H), 2.60-2.50 (m, 1H), 2.48-2.32 (m, 1H). Purity 93%, MS (m/e) 403 (M+H)⁺.

I-51 (±)—N-(5,6-Dihydro-4H-benzo[f]imidazo[1,2-a]azepin-4-yl)-4-phenoxypicolinamide

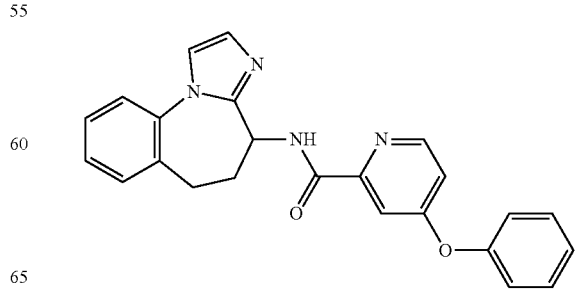

¹H NMR (400 MHz, Chloroform-d) δ 9.21 (d, J=7.7 Hz, 1H), 8.46 (dd, J=5.6, 0.6 Hz, 1H), 7.65 (d, J=2.6 Hz, 1H), 7.43-7.26 (m, 5H), 7.25-7.19 (m, 2H), 7.18 (d, J=1.4 Hz, 1H), 7.15 (d, J=1.4 Hz, 1H), 7.08-7.03 (m, 2H), 6.93 (dd, J=5.6, 2.5 Hz, 1H), 5.07 (dt, J=10.5, 7.7 Hz, 1H), 3.01-2.92 (m, 1H), 2.72-2.56 (m, 2H), 2.19-2.11 (m, 1H). Purity 94%, MS (m/e) 397 (M+H)⁺.

I-52 (±)—N-(1-Oxo-5,6-dihydro-1H,4H-benzo[f][1,2,4]oxadiazolo[4,3-a]azepin-4-yl)-4-phenoxypicolinamide

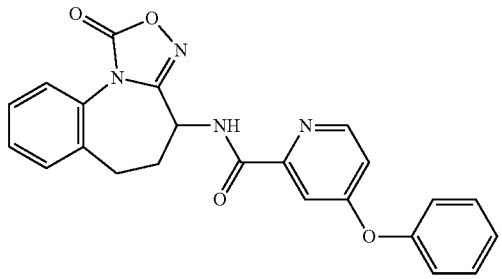 [SMILES: O=C(NC1CCc2ccccc2-n2c1noc2=O)c1cc(Oc2ccccc2)ccn1]

¹H NMR (400 MHz, Chloroform-d) δ 8.53 (d, J=8.8 Hz, 1H), 8.38 (d, J=5.6 Hz, 1H), 7.62 (d, J=2.5 Hz, 1H), 7.58 (dd, J=7.9, 1.3 Hz, 1H), 7.48-7.30 (m, 5H), 7.24 (app dt, J=14.9, 1.2 Hz, 1H), 7.10-7.01 (m, 2H), 6.95 (dd, J=5.6, 2.5 Hz, 1H), 5.10 (dt, J=9.8, 8.3 Hz, 1H), 2.91-2.80 (m, 2H), 2.80-2.56 (m, 1H), 2.33-2.12 (m, 1H). Purity 95%, MS (m/e) 415 (M+H)⁺.

I-54 (±)—N-(6,7-Dihydrobenzo[b]pyrrolo[1,2-d][1,4]oxazepin-7-yl)-4-phenoxypicolinamide

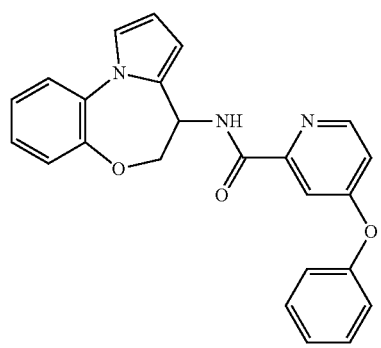 [SMILES: O=C(NC1COc2ccccc2-n2cccc21)c1cc(Oc2ccccc2)ccn1]

¹H NMR (400 MHz, Chloroform-d) δ 8.38-8.29 (m, 2H), 7.66-7.61 (m, 1H), 7.46-7.36 (m, 3H), 7.29-7.18 (m, 4H), 7.10-7.02 (m, 2H), 7.00 (t, J=2.3 Hz, 1H), 6.93 (dd, J=5.6, 2.5 Hz, 1H), 6.32-6.25 (m, 2H), 5.54 (ddd, J=9.2, 7.3, 6.1 Hz, 1H), 4.67 (dd, J=10.7, 6.1 Hz, 1H), 4.35 (dd, J=10.7, 7.3 Hz, 1H). Purity 99%, MS (m/e) 398 (M+H)⁺.

I-55 (±)-5-Benzyl-N-(9-(3-hydroxy-3-methylbut-1-yn-1-yl)-5,6-dihydro-4H-benzo[f]imidazo[1,2-a]azepin-4-yl)-1H-1,2,4-triazole-3-carboxamide

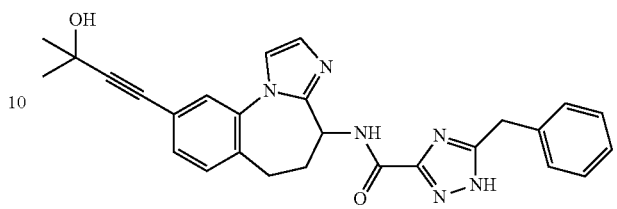

¹H NMR (400 MHz, Methanol-d₄) δ 7.49 (d, J=1.4 Hz, 1H), 7.43-7.36 (m, 3H), 7.34-7.19 (m, 5H), 7.03 (d, J=1.5 Hz, 1H), 5.02 (dd, J=10.7, 7.5 Hz, 1H), 4.15 (s, 2H), 2.84-2.76 (m, 1H), 2.73-2.61 (m, 1H), 2.52-2.48 (m, 1H), 2.38-2.34 (m, 1H), 1.55 (s, 6H). Purity 960, MS (m/e) 467 (M+H)⁺.

I-56 (±)—N-(9-(3-Hydroxy-3-methylbut-1-yn-1-yl)-5,6-dihydro-4H-benzo[f]imidazo[1,2-a]azepin-4-yl)-4-phenoxypicolinamide

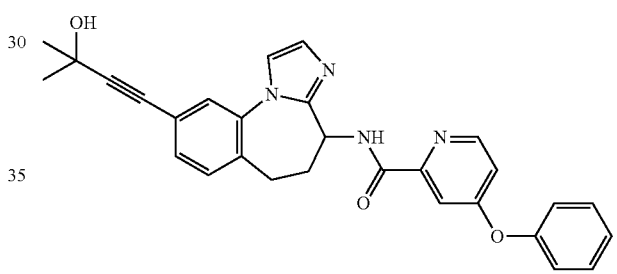

¹H NMR (400 MHz, Methanol-d₄) δ 8.49 (dd, J=5.6, 0.5 Hz, 1H), 7.51-7.37 (m, 7H), 7.29 (ddt, J=7.9, 7.0, 1.1 Hz, 1H), 7.18-7.09 (m, 2H), 7.13-7.02 (m, 2H), 5.02 (dd, J=10.3, 7.3 Hz, 1H), 2.84-2.66 (m, 2H), 2.60-2.48 (m, 1H), 2.39-2.26 (m, 1H), 1.55 (s, 6H). Purity 97%, MS (m/e) 479 (M+H)⁺.

I-57 (±)-5-Benzyl-N-(5,6-dihydro-4H-benzo[f][1,2,4]triazolo[4,3-a]azepin-4-yl)-1H-1,2,4-triazole-3-carboxamide

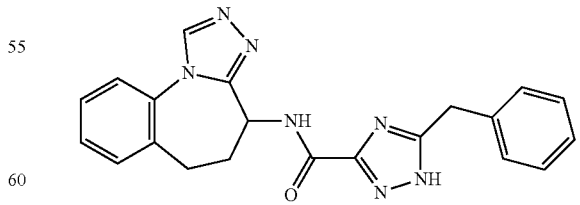

¹H NMR (400 MHz, Methanol-d₄) δ 8.84 (s, 1H), 7.70-7.38 (m, 4H), 7.38-7.08 (m, 5H), 5.13 (dd, J=10.6, 7.9 Hz, 1H), 4.16 (s, 2H), 2.90-2.81 (m, 1H), 2.77-2.63 (m, 1H), 2.64-2.52 (m, 1H), 2.48-2.37 (m, 1H). Purity 90%, MS (m/e) 386 (M+H)⁺.

I-58 (±)-1-(2,6-Dichlorobenzyl)-N-(5,6-dihydro-4H-benzo[f][1,2,4]triazolo[4,3-a]azepin-4-yl)-1H-1,2,4-triazole-3-carboxamide

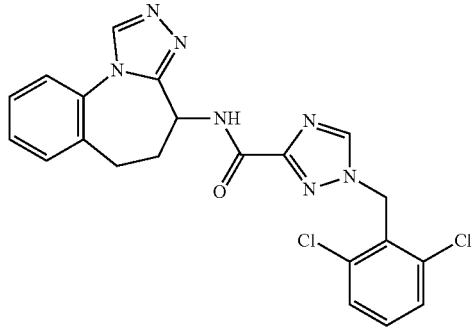 [SMILES: O=C(NC1CCc2ccccc2-n2cnnc21)c1ncn(Cc2c(Cl)cccc2Cl)n1]

$^1$H NMR (400 MHz, Methanol-d$_4$) δ 8.83 (s, 1H), 8.52 (s, 1H), 7.58-7.43 (m, 6H), 7.47-7.35 (m, 1H), 5.78 (s, 2H), 5.13 (dd, J=10.5, 7.9 Hz, 1H), 2.85 (ddd, J=13.6, 5.9, 2.2 Hz, 1H), 2.77-2.63 (m, 1H), 2.64-2.52 (m, 1H), 2.49-2.36 (m, 1H). Purity 91%, MS (m/e) 455 (M+H)$^+$.

I-60 (±)-1-(2,6-Dichlorobenzyl)-N-(2-methyl-1-oxo-2,4,5,6-tetrahydro-1H-benzo[f][1,2,4]triazolo[4,3-a]azepin-4-yl)-1H-1,2,4-triazole-3-carboxamide

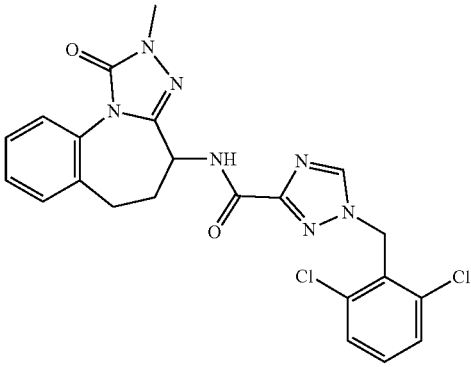

$^1$H NMR (400 MHz, Chloroform-d) δ 7.96 (s, 1H), 7.76 (d, J=8.4 Hz, 1H), 7.60 (dt, J=7.9, 1.0 Hz, 1H), 7.45-7.25 (m, 6H), 5.70 (s, 2H), 5.08 (dt, J=10.2, 8.1 Hz, 1H), 3.52 (s, 3H), 2.90-2.75 (m, 1H), 2.74-2.71 (m, 2H), 2.12-2.00 (m, 1H). Purity 96%, MS (m/e) 485 (M+H)$^+$.

I-59 (±)—N-(5,6-Dihydro-4H-benzo[f][1,2,4]triazolo[4,3-a]azepin-4-yl)-4-phenoxypicolinamide

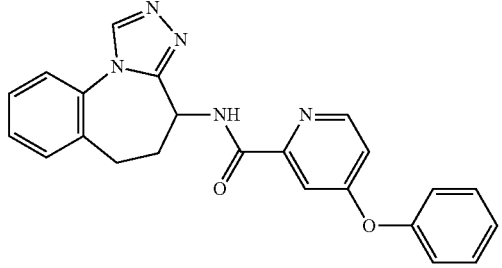 [SMILES: O=C(NC1CCc2ccccc2-n2cnnc21)c1cc(Oc2ccccc2)ccn1]

$^1$H NMR (400 MHz, Methanol-d$_4$) δ 8.84 (s, 1H), 8.50 (d, J=5.6 Hz, 1H), 7.58-7.41 (m, 7H), 7.33-7.24 (m, 1H), 7.18-7.10 (m, 2H), 7.07 (dd, J=5.6, 2.6 Hz, 1H), 5.13 (dd, J=10.3, 7.9 Hz, 1H), 2.86 (ddd, J=13.5, 6.2, 2.3 Hz, 1H), 2.82-2.68 (m, 1H), 2.68-2.55 (m, 1H), 2.49-2.36 (m, 1H). Purity 90%, MS (m/e) 398 (M+H)$^+$.

I-61 (±)—N-(9-(3-Oxa-9-azaspiro[5.5]undecan-9-yl)-5,6-dihydro-4H-benzo[f]imidazo[1,2-a]azepin-4-yl)-1-(2,6-dichlorobenzyl)-1H-1,2,4-triazole-3-carboxamide

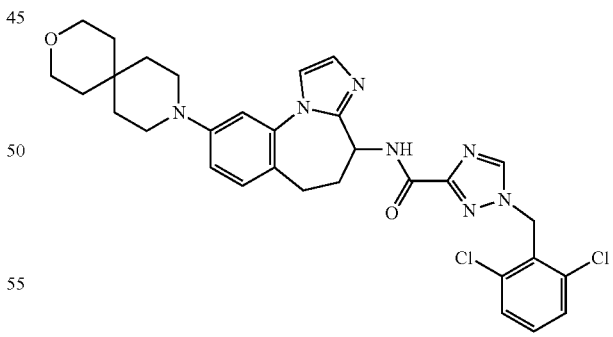

$^1$H NMR (400 MHz, Chloroform-d) δ 8.41 (d, J=7.8 Hz, 1H), 7.92 (d, J=0.6 Hz, 1H), 7.41 (dd, J=8.0, 0.9 Hz, 2H), 7.31 (dd, J=8.9, 7.1 Hz, 1H), 7.22-7.14 (m, 2H), 7.11 (d, J=1.4 Hz, 1H), 6.85 (dd, J=8.4, 2.5 Hz, 1H), 6.80 (d, J=2.6 Hz, 1H), 5.70 (s, 2H), 5.14 (dt, J=10.4, 7.7 Hz, 1H), 3.72-3.65 (m, 4H), 3.19 (dd, J=7.0, 4.6 Hz, 4H), 3.02-2.87 (m, 1H), 2.63-2.54 (m, 1H), 2.48 (td, J=13.3, 7.4 Hz, 1H), 2.12-2.00 (m, 1H), 1.74-1.66 (m, 4H), 1.59-1.51 (m, 4H). Purity 99%, MS (m/e) 607 (M+H)$^+$.

I-62 (±)—N-(9-(3-Oxa-9-azaspiro[5.5]undecan-9-yl)-5,6-dihydro-4H-benzo[f]imidazo[1,2-a]azepin-4-yl)-4-phenoxypicolinamide

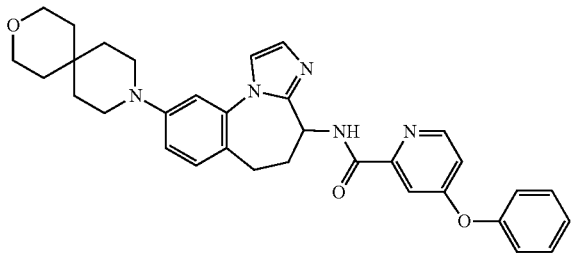 [SMILES: O=C(NC1CCc2ccc(N3CCC4(CCOCC4)CC3)cc2-n2ccnc21)c1cc(Oc2ccccc2)ccn1]

$^1$H NMR (400 MHz, Chloroform-d) δ 9.19 (d, J=7.8 Hz, 1H), 8.46 (dd, J=5.6, 0.6 Hz, 1H), 7.68-7.63 (m, 1H), 7.44-7.35 (m, 2H), 7.24-7.18 (m, 2H), 7.15 (dd, J=15.9, 1.4 Hz, 2H), 7.09-7.04 (m, 2H), 6.93 (dd, J=5.6, 2.6 Hz, 1H), 6.86 (dd, J=8.4, 2.5 Hz, 1H), 6.81 (d, J=2.5 Hz, 1H), 5.09 (dt, J=10.5, 7.8 Hz, 1H), 3.72-3.65 (m, 4H), 3.23-3.14 (m, 4H), 2.97-2.79 (m, 1H), 2.64-2.41 (m, 2H), 2.16-2.04 (m, 1H), 1.74-1.67 (m, 4H), 1.57-1.53 (m, 4H). Purity 99%, MS (m/e) 550 (M+H)$^+$.

I-63 (±)-1-Benzyl-N-(5,6-Dihydro-4H-benzo[f][1,2,4]triazolo[4,3-a]azepin-4-yl)-1H-1,2,4-triazole-3-carboxamide

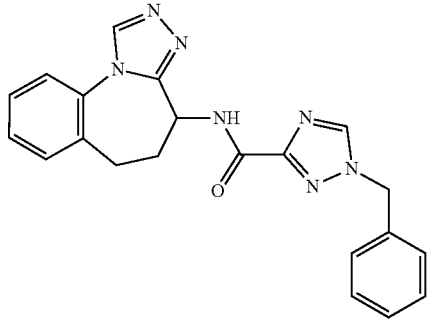 [SMILES: O=C(NC1CCc2ccccc2-n2cnnc21)c1ncn(Cc2ccccc2)n1]

$^1$H NMR (400 MHz, Chloroform-d) δ 8.40 (s, 1H), 8.37 (d, J=8.1 Hz, 1H), 8.01 (s, 1H), 7.46-7.31 (m, 7H), 7.31-7.25 (m, 2H), 5.38 (s, 2H), 5.30 (dt, J=10.4, 8.1 Hz, 1H), 3.10-2.93 (m, 1H), 2.83-2.67 (m, 1H), 2.67-2.47 (m, 1H), 2.25-2.11 (m, 1H). Purity 98%, MS (m/e) 386 (M+H)$^+$.

I-64 (±)—N-(9-(3-Oxa-9-azaspiro[5.5]undecan-9-yl)-5,6-dihydro-4H-benzo[f]imidazo[1,2-a]azepin-4-yl)-5-benzyl-1H-1,2,4-triazole-3-carboxamide

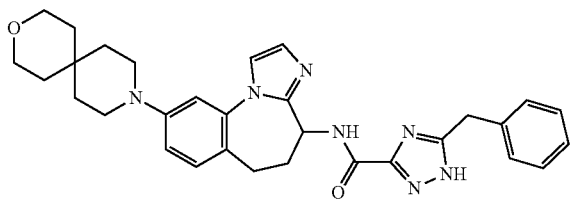 [SMILES: O=C(NC1CCc2ccc(N3CCC4(CCOCC4)CC3)cc2-n2ccnc21)c1n[nH]c(Cc2ccccc2)n1]

$^1$H NMR (400 MHz, Chloroform-d) δ 8.02 (d, J=8.8 Hz, 1H), 7.33-7.26 (m, 1H), 7.30-7.23 (m, 2H), 7.26-7.18 (m, 2H), 7.17 (d, J=8.4 Hz, 1H), 7.11 (d, J=1.4 Hz, 1H), 6.90-6.80 (m, 2H), 6.76 (s, 1H), 5.31-5.17 (m, 1H), 4.10 (s, 2H), 3.73-3.66 (m, 5H), 3.24-3.17 (m, 5H), 2.74-2.55 (m, 2H), 2.50-2.37 (m, 1H), 2.21-2.09 (m, 1H), 1.74-1.69 (m, 4H), 1.56-1.52 (m, 4H). $^1$H NMR (400 MHz, Methanol-d$_4$) δ 7.41 (d, J=1.5 Hz, 1H), 7.36-7.20 (m, 6H), 7.05-6.95 (m, 3H), 5.05 (dd, J=10.4, 7.1 Hz, 1H), 4.16 (s, 2H), 3.73-3.66 (m, 4H), 3.28-3.20 (m, 4H), 2.73-2.56 (m, 2H), 2.49-2.36 (m, 1H), 2.32-2.24 (m, 1H), 1.76-1.68 (m, 4H), 1.60-1.53 (m, 4H). Purity 99%, MS (m/e) 538 (M+H)$^+$.

I-65 (±)-5-Benzyl-N-(1-oxo-9-(3-oxa-9-azaspiro[5.5]undecan-9-yl)-5,6-dihydro-1H,4H-benzo[f][1,2,4]oxadiazolo[4,3-a]azepin-4-yl)-1H-1,2,4-triazole-3-carboxamide

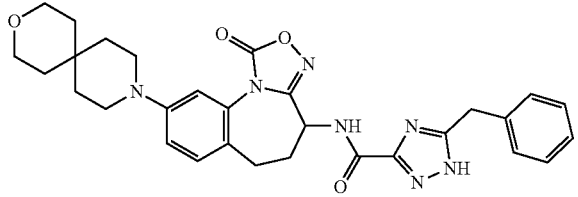 [SMILES: O=C(NC1CCc2ccc(N3CCC4(CCOCC4)CC3)cc2-n2c1noc2=O)c1n[nH]c(Cc2ccccc2)n1]

$^1$H NMR (400 MHz, Chloroform-d) δ 11.13 (br s, 1H), 7.61 (d, J=8.9 Hz, 1H), 7.38-7.24 (m, 5H), 7.15 (d, J=8.5 Hz, 1H), 7.06 (d, J=2.5 Hz, 1H), 6.87 (dd, J=8.5, 2.6 Hz, 1H), 5.13 (q, J=9.0 Hz, 1H), 4.16 (s, 2H), 3.72-3.65 (m, 4H), 3.20 (app dd, J=7.3, 4.6 Hz, 4H), 2.76-2.59 (m, 3H), 2.20-2.09 (m, 1H), 1.72-1.65 (m, 4H), 1.57-1.52 (m, 4H). Purity 94%, MS (m/e) 556 (M+H)$^+$.

I-66 (±)-5-Benzyl-N-(4,5-dihydroimidazo[1,2-a]quinolin-4-yl)-1H-1,2,4-triazole-3-carboxamide

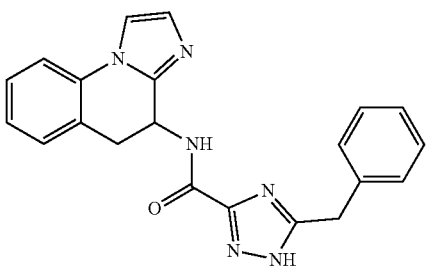 [SMILES: O=C(NC1Cc2ccccc2-n2ccnc21)c1n[nH]c(Cc2ccccc2)n1]

$^1$H NMR (400 MHz, Methanol-d$_4$) δ 7.77 (d, J=1.6 Hz, 1H), 7.58-7.54 (m, 1H), 7.42-7.35 (m, 2H), 7.33-7.17 (m, 6H), 7.10 (d, J=1.6 Hz, 1H), 5.54 (dd, J=9.2, 6.1 Hz, 1H), 4.12 (s, 2H), 3.35-2.87 (app m, 2H). Purity 95%, MS (m/e) 371 (M+H)$^+$.

I-67 (±)—N-(4,5-Dihydroimidazo[1,2-a]quinolin-4-yl)-4-phenoxypicolinamide

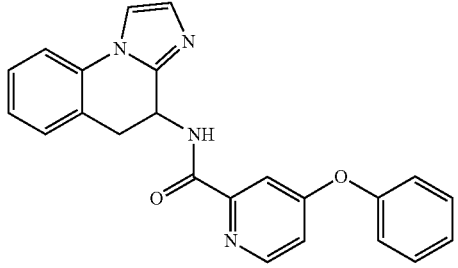 [SMILES: O=C(NC1Cc2ccccc2-n2ccnc21)c1cc(Oc2ccccc2)ccn1]

¹H NMR (400 MHz, Methanol-d₄) δ 8.43 (d, J=5.6 Hz, 1H), 7.77 (d, J=1.6 Hz, 1H), 7.59 (d, J=2.5 Hz, 1H), 7.58-7.54 (m, 1H), 7.51-7.44 (m, 2H), 7.43-7.35 (m, 2H), 7.34-7.27 (m, 1H), 7.23 (td, J=7.5, 1.2 Hz, 1H), 7.17-7.13 (m, 2H), 7.09 (d, J=1.5 Hz, 1H), 7.05 (dd, J=5.6, 2.6 Hz, 1H), 5.48 (dd, J=9.2, 6.1 Hz, 1H), 3.38-3.24 (app m, 2H). Purity 96%, MS (m/e) 383 (M+H)⁺.

I-68 (±)-5-Benzyl-N-(9-(3-hydroxy-3-methylbutyl)-5,6-dihydro-4H-benzo[f]imidazo[1,2-a]azepin-4-yl)-1H-1,2,4-triazole-3-carboxamide

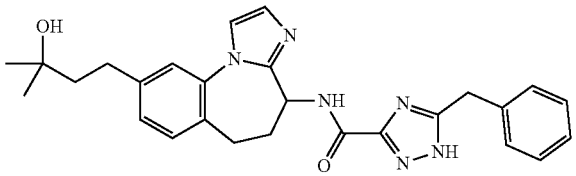 [SMILES: CC(C)(O)CCc1ccc2c(c1)-n1ccnc1C(NC(=O)c1n[nH]c(Cc3ccccc3)n1)CC2]

¹H NMR (400 MHz, Chloroform-d) δ 7.97 (d, J=8.5 Hz, 1H), 7.31-7.27 (m, 1H), 7.26 (d, J=0.9 Hz, 1H), 7.25-7.19 (m, 4H), 7.17-7.14 (m, 2H), 7.11 (d, J=1.4 Hz, 1H), 6.72 (s, 1H), 5.28-5.20 (app m, 1H), 4.10 (s, 2H), 2.80-2.62 (m, 5H), 2.54-2.45 (m, 1H), 2.22-2.18 (m, 1H), 1.86-1.77 (m, 2H), 1.31 (s, 6H). Purity 93%, MS (m/e) 471 (M+H)⁺.

I-72 (±)-5-Benzyl-N-(9-(3-hydroxy-3-methylbut-1-yn-1-yl)-5,6-dihydro-4H-benzo[f][1,2,4]triazolo[4,3-a]azepin-4-yl)-1H-1,2,4-triazole-3-carboxamide

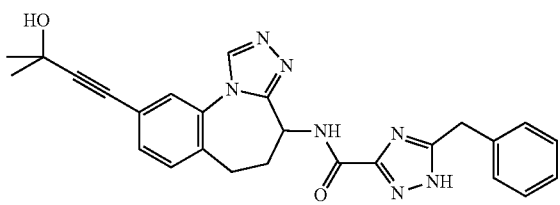 [SMILES: CC(C)(O)C#Cc1ccc2c(c1)-n1cnnc1C(NC(=O)c1n[nH]c(Cc3ccccc3)n1)CC2]

¹H NMR (400 MHz, Methanol-d₄) δ 8.86 (s, 1H), 7.63 (d, J=1.2 Hz, 1H), 7.49 (s, 2H), 7.36-7.20 (m, 5H), 5.15 (dd, J=10.5, 7.9 Hz, 1H), 4.17 (s, 2H), 2.92-2.82 (m, 1H), 2.78-2.64 (m, 1H), 2.64-2.52 (m, 1H), 2.50-2.38 (m, 1H), 1.56 (s, 6H). Purity 98%, MS (m/e) 468 (M+H)⁺.

I-77 (±)—N-(9-(3-Oxa-9-azaspiro[5.5]undecan-9-yl)-5,6-dihydro-4H-benzo[f]imidazo[1,2-a]azepin-4-yl)-1-benzyl-1H-pyrazole-3-carboxamide

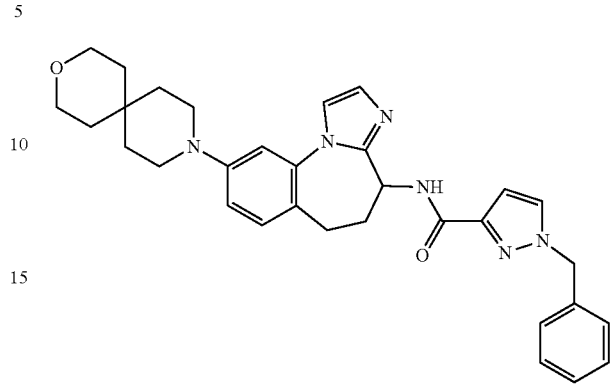

¹H NMR (400 MHz, Chloroform-d) δ 8.11 (d, J=7.9 Hz, 1H), 7.41-7.28 (m, 4H), 7.24 (d, J=2.0 Hz, 1H), 7.26-7.17 (m, 3H), 7.15 (d, J=1.4 Hz, 1H), 6.88 (dd, J=8.4, 2.5 Hz, 1H), 6.83 (d, J=2.5 Hz, 1H), 6.77 (d, J=2.3 Hz, 1H), 5.32 (app q, J=17.3 Hz, 2H), 5.17 (dt, J=10.5, 7.8 Hz, 1H), 3.74-3.66 (m, 4H), 3.24-3.17 (m, 4H), 2.96-2.82 (m, 1H), 2.65-2.56 (m, 1H), 2.43-2.45 (app m, 1H), 2.21-2.09 (m, 1H), 1.75-1.68 (m, 4H), 1.60-1.53 (m, 4H). Purity 95%, MS (m/e) 537 (M+H)⁺.

I-82 (S)-5-Benzyl-N-(9-(3-hydroxy-3-methylbut-1-yn-1-yl)-5,6-dihydro-4H-benzo[f]imidazo[1,2-a]azepin-4-yl)-1H-1,2,4-triazole-3-carboxamide

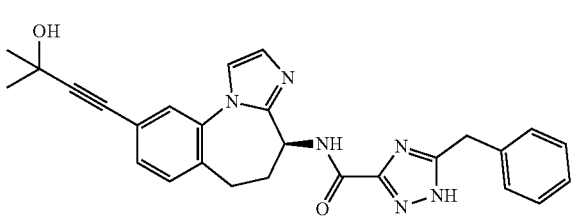 [SMILES: CC(C)(O)C#Cc1ccc2c(c1)-n1ccnc1[C@@H](NC(=O)c1n[nH]c(Cc3ccccc3)n1)CC2]

¹H NMR (400 MHz, Methanol-d₄) δ 7.50 (d, J=1.3 Hz, 1H), 7.45-7.40 (m, 3H), 7.35-7.21 (m, 5H), 7.05 (d, J=1.5 Hz, 1H), 5.04 (dd, J=10.7, 7.5 Hz, 1H), 4.16 (s, 2H), 2.85-2.75 (m, 1H), 2.74-2.65 (m, 1H), 2.58-2.48 (m, 1H), 2.40-2.30 (m, 1H), 1.56 (s, 6H). Purity 97%, MS (m/e) 467 (M+H)⁺.

I-83 (S)—N-(9-(3-Oxa-9-azaspiro[5.5]undecan-9-yl)-5,6-dihydro-4H-benzo[f]imidazo[1,2-a]azepin-4-yl)-5-benzyl-1H-1,2,4-triazole-3-carboxamide

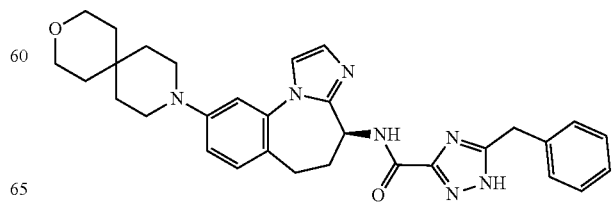

¹H NMR (400 MHz, Methanol-d₄) δ 7.41 (d, J=1.4 Hz, 1H), 7.36-7.18 (m, 6H), 7.03 (d, J=1.4 Hz, 1H), 7.02-6.97 (m, 2H), 5.12-5.01 (app m, 1H), 4.16 (s, 2H), 3.75-3.64 (m, 4H), 3.27-3.20 (m, 4H), 2.75-2.55 (m, 2H), 2.55-2.36 (m, 1H), 2.36-2.17 (m, 1H), 1.79-1.65 (m, 4H), 1.65-1.49 (m, 4H). Purity 95%, MS (m/e) 538 (M+H)⁺.

I-84 (±)—N-(9-(7-Oxa-2-azaspiro[3.5]nonan-2-yl)-5,6-dihydro-4H-benzo[f]imidazo[1,2-a]azepin-4-yl)-5-benzyl-1H-1,2,4-triazole-3-carboxamide

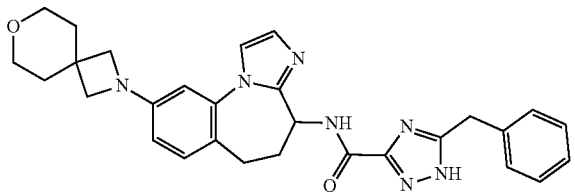 [SMILES: O=C(NC1CCc2ccc(N3CC4(CCOCC4)C3)cc2-n2ccnc21)c1n[nH]c(Cc2ccccc2)n1]

¹H NMR (400 MHz, Methanol-d₄) δ 7.39 (d, J=1.4 Hz, 1H), 7.35-7.18 (m, 6H), 7.02 (d, J=1.4 Hz, 1H), 6.53 (d, J=2.3 Hz, 1H), 6.49 (dd, J=8.2, 2.4 Hz, 1H), 5.05 (dd, J=10.5, 7.0 Hz, 1H), 4.16 (s, 2H), 3.75-3.57 (m, 8H), 2.72-2.53 (m, 2H), 2.52-2.33 (m, 1H), 2.34-2.17 (m, 1H), 1.90-1.76 (m, 4H). Purity 97%, MS (m/e) 510 (M+H)⁺.

I-85 (±)—N-(9-(7-Oxa-2-azaspiro[3.5]nonan-2-yl)-5,6-dihydro-4H-benzo[f]imidazo[1,2-a]azepin-4-yl)-1-benzyl-1H-pyrazole-3-carboxamide

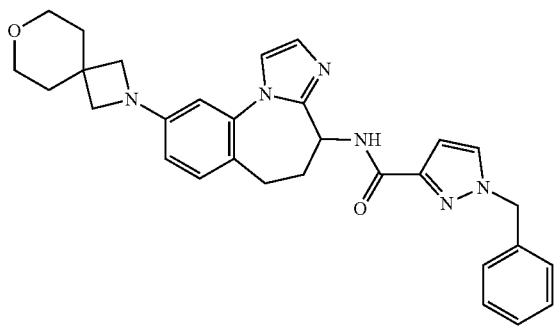 [SMILES: O=C(NC1CCc2ccc(N3CC4(CCOCC4)C3)cc2-n2ccnc21)c1ccn(Cc2ccccc2)n1]

¹H NMR (400 MHz, Methanol-d₄) δ 7.70 (d, J=2.4 Hz, 1H), 7.47 (d, J=1.6 Hz, 1H), 7.39-7.21 (m, 6H), 7.12 (d, J=1.5 Hz, 1H), 6.75 (d, J=2.4 Hz, 1H), 6.55 (d, J=2.3 Hz, 1H), 6.51 (dd, J=8.2, 2.4 Hz, 1H), 5.40 (s, 2H), 5.09 (dd, J=10.3, 7.1 Hz, 1H), 3.74-3.61 (m, 8H), 2.72-2.55 (m, 2H), 2.50-2.38 (m, 1H), 2.38-2.22 (m, 1H), 1.87-1.78 (m, 4H). Purity 96%, MS (m/e) 509 (M+H)⁺.

I-86 (S)—N-(9-(7-Oxa-2-azaspiro[3.5]nonan-2-yl)-5,6-dihydro-4H-benzo[f]imidazo[1,2-a]azepin-4-yl)-5-benzyl-1H-1,2,4-triazole-3-carboxamide

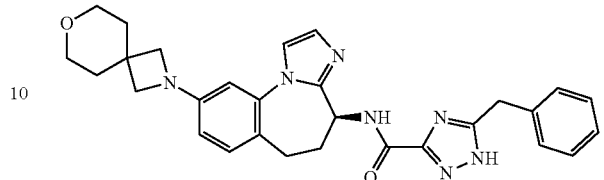

¹H NMR (400 MHz, Methanol-d₄) δ 7.38 (d, J=1.5 Hz, 1H), 7.35-7.20 (m, 6H), 7.02 (d, J=1.5 Hz, 1H), 6.52 (d, J=2.3 Hz, 1H), 6.49 (dd, J=8.2, 2.4 Hz, 1H), 5.05 (dd, J=10.5, 7.0 Hz, 1H), 4.16 (s, 2H), 3.73-3.61 (m, 8H), 2.71-2.53 (m, 2H), 2.52-2.34 (m, 1H), 2.33-2.15 (m, 1H), 1.84 (app t, J=5.3 Hz, 4H). Purity 96%, MS (m/e) 510 (M+H)⁺.

R955395 (R)—N-(9-(7-Oxa-2-azaspiro[3.5]nonan-2-yl)-4,5-dihydrobenzo[b]imidazo[1,2-d][1,4]oxazepin-4-yl)-5-benzyl-1H-1,2,4-triazole-3-carboxamide

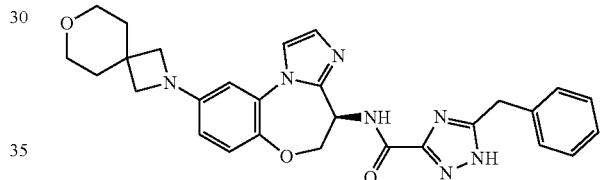

¹H NMR (400 MHz, Methanol-d₄) δ 7.50 (d, J=1.5 Hz, 1H), 7.36-7.19 (m, 5H), 7.14 (d, J=8.7 Hz, 1H), 7.07 (d, J=1.5 Hz, 1H), 6.60 (d, J=2.7 Hz, 1H), 6.48 (dd, J=8.7, 2.7 Hz, 1H), 5.48 (dd, J=9.5, 7.0 Hz, 1H), 4.60 (dd, J=10.6, 7.0 Hz, 1H), 4.38 (dd, J=10.5, 9.5 Hz, 1H), 4.16 (s, 2H), 3.73-3.64 (m, 8H), 1.88-1.80 (m, 4H). Purity 98%, MS (m/e) 512 (M+H)⁺.

I-88 (R)—N-(9-(7-Oxa-2-azaspiro[3.5]nonan-2-yl)-4,5-dihydrobenzo[b]imidazo[1,2-d][1,4]oxazepin-4-yl)-4-phenoxypicolinamide

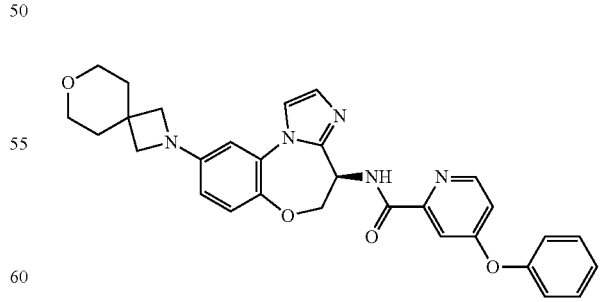

¹H NMR (400 MHz, Chloroform-d) δ 9.18 (d, J=7.6 Hz, 1H), 8.48 (d, J=5.6 Hz, 1H), 7.66 (d, J=2.5 Hz, 1H), 7.48-7.36 (m, 2H), 7.30-7.22 (m, 2H), 7.19 (d, J=1.4 Hz, 1H), 7.17-7.12 (m, 1H), 7.12-7.04 (m, 2H), 6.96 (dd, J=5.6, 2.5 Hz, 1H), 6.38 (app dd, J=6.7, 2.7 Hz, 2H), 5.43 (dt, J=9.8, 7.2 Hz, 1H), 4.84 (dd, J=10.1, 7.0 Hz, 1H), 4.25 (t, J=10.0 Hz, 1H), 3.72-3.63 (m, 8H), 1.34-1.20 (m, 4H). Purity 97%, MS (m/e) 524 (M+H)$^+$.

I-89 (R)-5-Benzyl-N-(9-(pyridin-2-ylethynyl)-4,5-dihydrobenzo[b]imidazo[1,2-d][1,4]oxazepin-4-yl)-1H-1,2,4-triazole-3-carboxamide

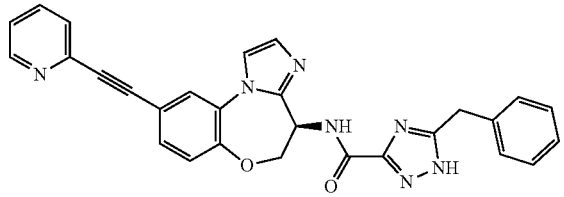 [SMILES: O=C(N[C@H]1COc2ccc(C#Cc3ccccn3)cc2-n2ccnc21)c1n[nH]c(Cc2ccccc2)n1]

$^1$H NMR (400 MHz, Methanol-d$_4$) δ 8.72 (dd, J=2.1, 0.9 Hz, 1H), 8.53 (dd, J=5.0, 1.6 Hz, 1H), 7.99 (dt, J=7.9, 1.9 Hz, 1H), 7.88 (d, J=1.9 Hz, 1H), 7.65 (d, J=1.6 Hz, 1H), 7.57 (dd, J=8.3, 2.0 Hz, 1H), 7.47 (ddd, J=7.9, 5.0, 0.9 Hz, 1H), 7.37-7.19 (m, 6H), 7.13 (d, J=1.5 Hz, 1H), 5.60 (dd, J=8.8, 6.1 Hz, 1H), 4.70 (dd, J=11.0, 6.1 Hz, 1H), 4.54 (dd, J=11.0, 8.9 Hz, 1H), 4.16 (s, 2H). Purity 96%, MS (m/e) 488 (M+H)$^+$.

I-90 (±)-5-Benzyl-N-(9-(3-hydroxy-3-methylbut-1-yn-1-yl)-4,5-dihydrobenzo[b]imidazo[1,2-d][1,4]oxazepin-4-yl)-1H-1,2,4-triazole-3-carboxamide

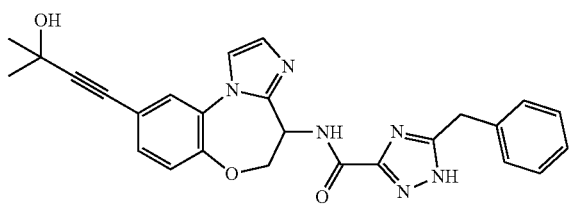 [SMILES: CC(C)(O)C#Cc1ccc2c(c1)-n1ccnc1C(NC(=O)c1n[nH]c(Cc3ccccc3)n1)CO2]

$^1$H NMR (400 MHz, Methanol-d$_4$) δ 7.67 (s, 1H), 7.58 (s, 1H), 7.40 (d, J=8.5 Hz, 1H), 7.33-7.21 (m, 6H), 7.11 (s, 1H), 5.61-5.51 (app m, 1H), 4.67 (app t, J=8.3 Hz, 1H), 4.50 (app t, J=10.0 Hz, 1H), 4.15 (s, 2H), 1.56 (s, 6H). Purity 92%, MS (m/e) 469 (M+H)$^+$.

I-93 (±)-4-(4-Fluorobenzyl)-N-(9-(3-hydroxy-3-methylbut-1-yn-1-yl)-5,6-dihydro-4H-benzo[f]imidazo[1,2-a]azepin-4-yl)-1H-pyrazole-1-carboxamide

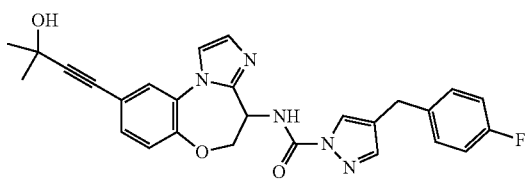 [SMILES: CC(C)(O)C#Cc1ccc2c(c1)-n1ccnc1C(NC(=O)n1cc(Cc3ccc(F)cc3)cn1)CO2]

$^1$H NMR (400 MHz, Dichloromethane-d$_2$) δ 8.31 (d, J=7.2 Hz, 1H), 7.89 (q, J=0.9 Hz, 1H), 7.49 (d, J=0.9 Hz, 1H), 7.41-7.33 (m, 3H), 7.25 (d, J=1.5 Hz, 1H), 7.22-7.15 (m, 2H), 7.13 (d, J=1.4 Hz, 1H), 7.03-6.94 (m, 2H), 4.87 (dt, J=10.5, 7.5 Hz, 1H), 3.81 (s, 2H), 3.04-2.85 (m, 1H), 2.81-2.67 (m, 1H), 2.62-2.54 (m, 1H), 2.25-2.13 (m, 1H), 2.08 (s, 1H), 1.59 (s, 6H). $^{19}$F NMR (376 MHz, Dichloromethane-d$_2$) δ −117.81−−117.88 (ddd, J=14.2, 8.9, 5.4 Hz). Purity 92%, MS (m/e) 484 (M+H)$^+$.

Chromatographic Separation of Enantiomers:

The compounds disclosed herein can be synthesized in racemic or in enantiomerically enriched form as taught herein to those of ordinary skill in the art of organic synthesis. Racemic mixtures of the compounds disclosed herein can be separated into their constituent enantiomers using the following chiral chromatography procedures and adaptations thereof as known to those ordinary skill in the art.

I-4 (S)-5-Benzyl-N-(5,6-dihydro-4H-benzo[f]imidazo[1,2-a]azepin-4-yl)-1H-1,2,4-triazole-3-carboxamide and I-5 (R)-5-Benzyl-N-(5,6-dihydro-4H-benzo[f]imidazo[1,2-a]azepin-4-yl)-1H-1,2,4-triazole-3-carboxamide

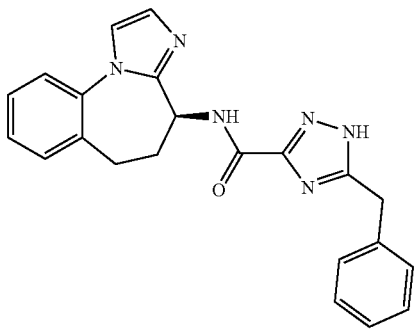

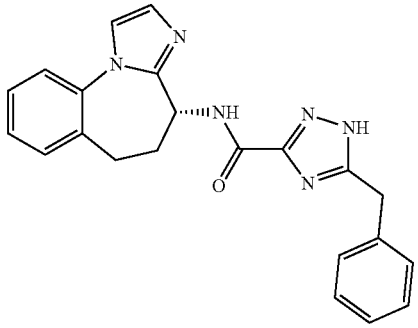

Chiral separation of (±)-5-Benzyl-N-(5,6-dihydro-4H-benzo[f]imidazo[1,2-a]azepin-4-yl)-1H-1,2,4-triazole-3-carboxamide was performed on Thar SFC instrument, fitted with a Chiracel AD-H, 10 micron, 10×250 mm column. Mobile phase was 18% methanol (0.1% DEA) and 82% CO$_2$ total flow rate was 12 mL/minute. Total elution time for enantiomer separation was 14.3 minutes. A total of sixty one 50 μL injections were made at a sample concentration of 11 mg/mL (in methanol) using injection stacking with a cycle time of 4.8 minutes and 0.3 min spacing. Samples were collected by monitoring UV adsorption at 214 nm. Peak-1 (a fast eluting peak) corresponds to (S)-5-Benzyl-N-(5,6-dihydro-4H-benzo[f]imidazo[1,2-a]azepin-4-yl)-1H-1,2,4-triazole-3-carboxamide whereas the Peak-2 (slow eluting peak) corresponds to (R)-5-Benzyl-N-(5,6-dihydro-4H-benzo[f]imidazo[1,2-a]azepin-4-yl)-1H-1,2,4-triazole-3-carboxamide. The solid obtained after concentrating the mixed fractions of each enantiomer dissolved in 5% MeOH/

EtOAc and passed through EtOAc conditioned silica gel. The concentrate of the filtrate dissolved in acetonitrile/water and lyophilized. Enantiomer enrichment was measured by analytical method on the same instrument using using Chiralcel-IA-H, 5 micron, 4.6×250 mm with 20% Methanol (0.1% DEA) 80% $CO_2$ as mobile phase eluting at the flow rate of 3.0 mL/min by 15 µL injection having the concentration of 1 mg/mL at the detector UV wavelength of 214 nm. I-4 (S)-5-Benzyl-N-(5,6-dihydro-4H-benzo[f]imidazo[1,2-a]azepin-4-yl)-1H-1,2,4-triazole-3-carboxamide (white solid). 98.5% ee. $^1$H NMR (400 MHz, Chloroform-d) δ 8.60 (d, J=9.0 Hz, 1H), 7.46-7.39 (m, 1H), 7.36-7.34 (m, 3H), 7.28 (d, J=6.9 Hz, 1H), 7.29-7.17 (m, 4H), 7.10 (d, J=1.4 Hz, 1H), 6.59 (s, 1H), 5.30 (q, J=9.5 Hz, 1H), 4.16 (app q, J=16.1 Hz, 2H), 2.84-2.65 (m, 2H), 2.57-2.49 (m, 1H), 2.28 (td, J=11.4, 10.9, 7.0 Hz, 1H). LCMS: Purity 99%, MS (m/e) 385 (M+H)$^+$. I-5 (R)-5-Benzyl-N-(5,6-dihydro-4H-benzo[f]imidazo[1,2-a]azepin-4-yl)-1H-1,2,4-triazole-3-carboxamide (white solid). 98.8% ee. $^1$H NMR (400 MHz, Chloroform-d) δ 8.59 (d, J=9.0 Hz, 1H), 7.44-7.39 (m, 1H), 7.36-7.33 (m, 3H), 7.30-7.21 (m, 5H), 7.10 (d, J=1.4 Hz, 1H), 6.61 (s, 1H), 5.36-5.15 (m, 1H), 4.16 (app q, J=16.0 Hz, 2H), 2.88-2.63 (m, 2H), 2.57-2.48 (m, 1H), 2.27 (td, J=11.4, 11.0, 7.0 Hz, 1H). LCMS: Purity 99%, MS (m/e) 385 (M+H)$^+$.

I-12 (R)-1-(2,6-Dichlorobenzyl)-N-(5,6-dihydro-4H-benzo[f]imidazo[1,2-a]azepin-4-yl)-1H-1,2,4-triazole-3-carboxamide and I-13 (S)-1-(2,6-dichlorobenzyl)-N-(5,6-dihydro-4H-benzo[f]imidazo[1,2-a]azepin-4-yl)-1H-1,2,4-triazole-3-carboxamide

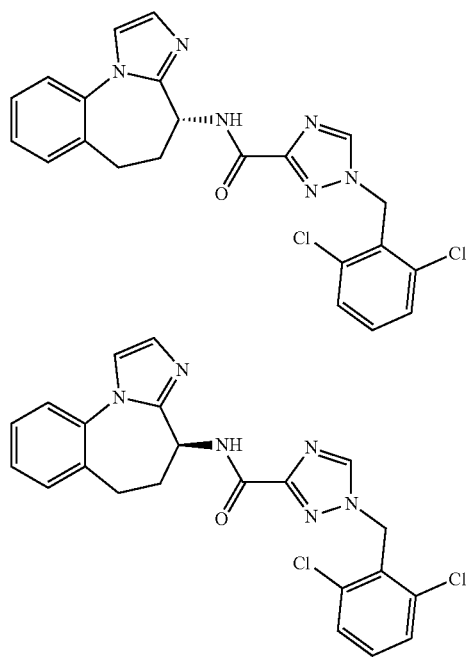

Chiral separation of (±)-1-(2,6-Dichlorobenzyl)-N-(5,6-dihydro-4H-benzo[f]imidazo[1,2-a]azepin-4-yl)-1H-1,2,4-triazole-3-carboxamide was performed on Thar SFC instrument, fitted with a Chiralcel OJ-H, 10 micron, 10×250 mm column. Mobile phase is 27% isopropyl alcohol (0.1% DEA) and 73% $CO_2$ total flow rate is 10.0 mL/minute. Total elution time for enantiomer separation is 12 minutes. A total of sixty one 40 µL injections were made at a sample concentration of 25 mg/mL (in methanol) using injection stacking with a cycle time of five minutes and 0.25 minute spacing. Samples were collected by monitoring UV adsorption at 214 nm. Peak-1 (a fast eluting peak) corresponds to (R)-1-(2,6-Dichlorobenzyl)-N-(5,6-dihydro-4H-benzo[f]imidazo[1,2-a]azepin-4-yl)-1H-1,2,4-triazole-3-carboxamide whereas the Peak-2 (slow eluting peak) corresponds to (S)-1-(2,6-dichlorobenzyl)-N-(5,6-dihydro-4H-benzo[f]imidazo[1,2-a]azepin-4-yl)-1H-1,2,4-triazole-3-carboxamide. The solid obtained after concentrating the mixed fractions of each enantiomer was dissolved in EtOAc and passed through EtOAc conditioned silica gel. The concentrate of the filtrate upon dissolving in acetonitrile/water subjected to lyophilization process. Enantiomeric enrichment was measured by analytical method on the same instrument using using Chiralcel-OJ-H, 5 micron, 4.6×250 mm with 27% isopropyl alcohol (0.1% DEA) 73% CO2 as mobile phase eluting at the flow rate of 3.0 mL/min by 10 µL injection having the concentration of 1 mg/mL at the detector UV wavelength of 214 nm. I-12: (R)-1-(2,6-Dichlorobenzyl)-N-(5,6-dihydro-4H-benzo[f]imidazo[1,2-a]azepin-4-yl)-1H-1,2,4-triazole-3-carboxamide (white solid). 98.9% ee. $^1$H NMR (400 MHz, Chloroform-d) δ 8.45 (d, J=7.6 Hz, 1H), 7.95 (s, 1H), 7.46-7.26 (m, 7H), 7.20 (s, 1H), 7.14 (s, 1H), 5.71 (s, 2H), 5.14 (q, J=8.3 Hz, 1H), 3.11-2.96 (m, 1H), 2.70 (dd, J=13.7, 6.5 Hz, 1H), 2.60 (td, J=13.2, 7.4 Hz, 1H), 2.18-2.10 (m, 1H). LCMS: Purity 99%, MS (m/e) 454 (M+H)$^+$. I-13: (S)-1-(2,6-Dichlorobenzyl)-N-(5,6-dihydro-4H-benzo[f]imidazo[1,2-a]azepin-4-yl)-1H-1,2,4-triazole-3-carboxamide (white solid). 99.6% ee. $^1$H NMR (400 MHz, Chloroform-d) δ 8.47 (d, J=7.7 Hz, 1H), 7.94 (s, 1H), 7.46-7.37 (m, 2H), 7.41-7.27 (m, 5H), 7.19 (d, J=1.4 Hz, 1H), 7.14 (d, J=1.4 Hz, 1H), 5.71 (s, 2H), 5.15 (dt, J=10.5, 7.7 Hz, 1H), 3.10-2.95 (m, 1H), 2.75-2.53 (m, 2H), 2.21-2.11 (m, 1H). LCMS: Purity 99%, MS (m/e) 454 (M+H)$^+$.

I-91 (S)-5-Benzyl-N-(9-(3-hydroxy-3-methylbut-1-yn-1-yl)-4,5-dihydrobenzo[b]imidazo[1,2-d][1,4]oxazepin-4-yl)-1H-1,2,4-triazole-3-carboxamide and I-92 (R)-5-Benzyl-N-(9-(3-hydroxy-3-methylbut-1-yn-1-yl)-4,5-dihydrobenzo[b]imidazo[1,2-d][1,4]oxazepin-4-yl)-1H-1,2,4-triazole-3-carboxamide

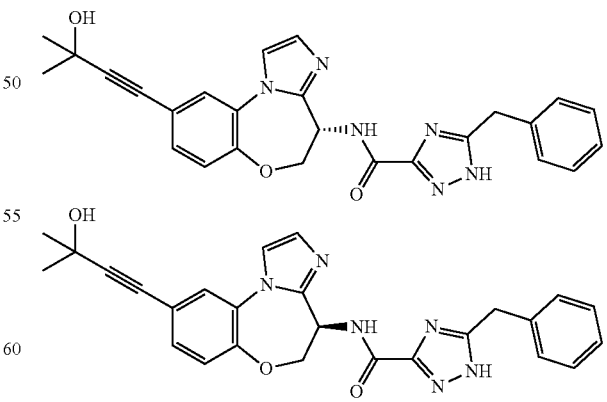

performed on Thar SFC instrument, fitted with Chiralcel OJ-H, 10 micron, 10×250 mm column. Mobile phase is 18% methanol (0.1% DEA) 82% $CO_2$ total flow rate is 10.0 mL/minute. Total elution time for enantiomer separation 11.3 minutes. A total of forty 50 µL injections were made at a sample concentration of 17 mg/mL (in methanol) using injection stacking with a cycle time of 2.9 minutes and 0.3 minute spacing. Samples were collected by monitoring UV adsorption at 214 nm. Peak-1 (a fast eluting peak) corresponds to (S)-5-Benzyl-N-(9-(3-hydroxy-3-methylbut-1-yn-1-yl)-4,5-dihydrobenzo[b]imidazo[1,2-d][1,4]oxazepin-4-yl)-1H-1,2,4-triazole-3-carboxamide whereas the Peak-2 (slow eluting peak) corresponds to (R)-5-Benzyl-N-(9-(3-hydroxy-3-methylbut-1-yn-1-yl)-4,5-dihydrobenzo[b]imidazo[1,2-d][1,4]oxazepin-4-yl)-1H-1,2,4-triazole-3-carboxamide. The solid that was obtained after concentrating the mixed fractions of each enantiomer dissolved in minimum amount of acetonitrile and diluted with water. The precipitous suspension was suction filtered, and thus collected solid dried to provide the respective compounds. Enantiomer enrichment was measured by analytical method on the same instrument using Chiralcel-OJ-H, 5 micron, 4.6×250 mm with 18% methanol (0.1% DEA) 82% $CO_2$ as mobile phase eluting at the flow rate of 3.0 mL/min by 10 µL injection having the concentration of 1 mg/mL at the detector UV wavelength of 214 nm. I-91: (S)-5-Benzyl-N-(9-(3-hydroxy-3-methylbut-1-yn-1-yl)-4,5-dihydrobenzo[b]imidazo[1,2-d][1,4]oxazepin-4-yl)-1H-1,2,4-triazole-3-carboxamide (white solid). 99.7% ee. $^1$H NMR (400 MHz, Methanol-$d_4$) δ 7.67 (d, J=1.9 Hz, 1H), 7.58 (d, J=1.5 Hz, 1H), 7.39 (dd, J=8.3, 1.9 Hz, 1H), 7.36-7.18 (m, 6H), 7.10 (d, J=1.5 Hz, 1H), 5.56 (dd, J=9.0, 6.2 Hz, 1H), 4.67 (dd, J=11.0, 6.2 Hz, 1H), 4.49 (dd, J=10.9, 9.0 Hz, 1H), 4.15 (s, 2H), 1.56 (s, 6H). Purity 99%, MS (m/e) 469 (M+H)$^+$. I-92: (R)-5-Benzyl-N-(9-(3-hydroxy-3-methylbut-1-yn-1-yl)-4,5-dihydrobenzo[b]imidazo[1,2-d][1,4]oxazepin-4-yl)-1H-1,2,4-triazole-3-carboxamide (white solid). 99.7% ee. $^1$H NMR (400 MHz, Methanol-$d_4$) δ 7.67 (d, J=1.9 Hz, 1H), 7.58 (d, J=1.6 Hz, 1H), 7.40 (dd, J=8.3, 1.9 Hz, 1H), 7.33-7.20 (m, 6H), 7.11 (d, J=1.5 Hz, 1H), 5.56 (dd, J=9.0, 6.2 Hz, 1H), 4.67 (dd, J=11.0, 6.2 Hz, 1H), 4.50 (dd, J=10.9, 9.0 Hz, 1H), 4.15 (s, 2H), 1.56 (s, 6H). Purity 95%, MS (m/e) 469 (M+H)$^+$.

I-60: (±)-1-(2,6-Dichlorobenzyl)-N-(2-methyl-1-oxo-2,4,5,6-tetrahydro-1H-benzo[f][1,2,4]triazolo[4,3-a]azepin-4-yl)-1H-1,2,4-triazole-3-carboxamide

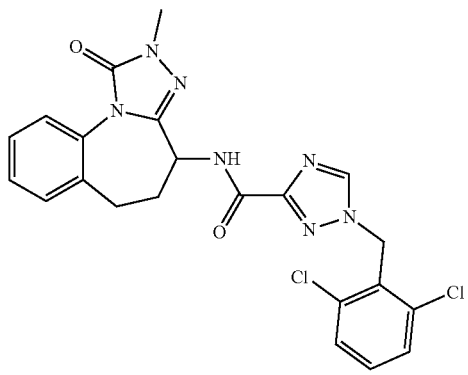 [SMILES: Cn1nc2n(c1=O)-c1ccccc1CCC2NC(=O)c1ncn(Cc2c(Cl)cccc2Cl)n1]

Iodomethane (2.6 µL, 6 mg, 0.042 mmol) was added all at once to a stirring hetereogeneous suspension of (±)-5-benzyl-N-(1-oxo-5,6-dihydro-1H,4H-benzo[f][1,2,4]oxadiazolo[4,3-a]azepin-4-yl)-1H-1,2,4-triazole-3-carboxamide (15 mg, 0.032 mmol) and $Cs_2CO_3$ (11 mg, 0.033 mmol) in dry DMF (0.2 mL) under nitrogen at room temperature. Reaction mixture was stirred for 1d, diluted with water (1 mL) and filtered. Thus collected solid upon suction drying was dissolved in $CH_2Cl_2$, loaded on to silica gel column, purified by flash chromatography [Combiflash© Teledyne RediSep© 50% EtOAc/hexanes conditioned silica gel column (4 G Gold) and eluted with 50-100% EtOAc/hexanes solvent] and obtained (±)-1-(2,6-dichlorobenzyl)-N-(2-methyl-1-oxo-2,4,5,6-tetrahydro-1H-benzo[f][1,2,4]triazolo[4,3-a]azepin-4-yl)-1H-1,2,4-triazole-3-carboxamide (11 mg) as a white solid. $^1$H NMR (400 MHz, Chloroform-d) δ 7.96 (s, 1H), 7.76 (d, J=8.4 Hz, 1H), 7.60 (dt, J=7.9, 1.0 Hz, 1H), 7.45-7.25 (m, 6H), 5.70 (s, 2H), 5.08 (dt, J=10.2, 8.1 Hz, 1H), 3.52 (s, 3H), 2.90-2.75 (m, 1H), 2.74-2.71 (m, 2H), 2.12-2.00 (m, 1H). Purity 96%, MS (m/e) 485 (M+H)$^+$.

I-70 (±)-5-Benzyl-N-(1,2-dichloro-5,6-dihydro-4H-benzo[f]imidazo[1,2-a]azepin-4-yl)isoxazole-3-carboxamide

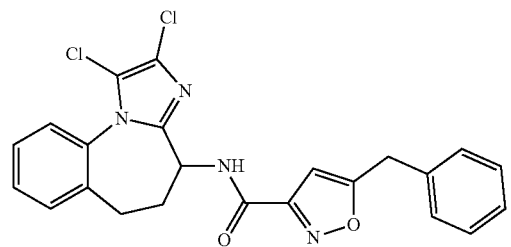 [SMILES: O=C(NC1CCc2ccccc2-n2c1nc(Cl)c2Cl)c1cc(Cc2ccccc2)on1]

$^1$H NMR (400 MHz, Chloroform-d) δ 7.83 (d, J=7.8 Hz, 1H), 7.49-7.20 (m, 9H), 6.32 (d, J=0.9 Hz, 1H), 4.99 (dt, J=10.7, 7.7 Hz, 1H), 4.11 (s, 2H), 2.94-2.79 (m, 1H), 2.76-2.66 (m, 1H), 2.61-2.52 (m, 1H), 2.17-2.04 (m, 1H). Purity 97%, MS (m/e) 454 (M+H)$^+$.

I-71 (1)-5-Benzyl-N-(1-chloro-5,6-dihydro-4H-benzo[f]imidazo[1,2-a]azepin-4-yl)isoxazole-3-carboxamide

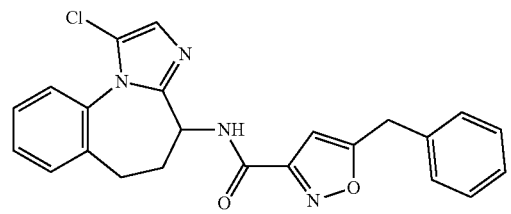 [SMILES: O=C(NC1CCc2ccccc2-n2c(Cl)cnc21)c1cc(Cc2ccccc2)on1]

$^1$H NMR (400 MHz, Chloroform-d) δ 8.02 (d, J=7.6 Hz, 1H), 7.47-7.19 (m, 9H), 7.04 (s, 1H), 6.33 (s, 1H), 4.95 (dt, J=10.6, 7.7 Hz, 1H), 4.11 (s, 2H), 2.96-2.81 (m, 1H), 2.74-2.64 (m, 1H), 2.59-2.50 (m, 1H), 2.15-2.02 (m, 1H). Purity 93%, MS (m/e) 420 (M+H)$^+$.

I-73 (±)—N-(1,2-Dichloro-5,6-dihydro-4H-benzo[f]imidazo[1,2-a]azepin-4-yl)-1-(2,6-dichlorobenzyl)-1H-1,2,4-triazole-3-carboxamide

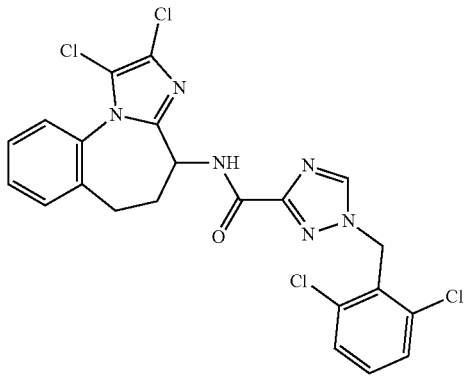 [SMILES: O=C(NC1CCc2ccccc2-n2c1nc(Cl)c2Cl)c1ncn(Cc2c(Cl)cccc2Cl)n1]

¹H NMR (400 MHz, Chloroform-d) δ 8.17 (d, J=8.0 Hz, 1H), 7.96 (s, 1H), 7.48-7.37 (m, 6H), 7.41-7.29 (m, 1H), 5.72 (s, 2H), 5.07 (dt, J=10.6, 7.8 Hz, 1H), 3.00-2.85 (m, 1H), 2.75-2.65 (m, 1H), 2.63-2.49 (m, 1H), 2.16-2.05 (m, 1H). Purity 95%, MS (m/e) 523 (M+H)⁺.

I-74 (±)—N-(1-Chloro-5,6-dihydro-4H-benzo[f]imidazo[1,2-a]azepin-4-yl)-1-(2,6-dichlorobenzyl)-1H-1,2,4-triazole-3-carboxamide

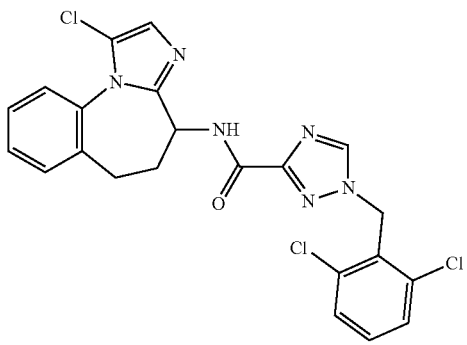 [SMILES: O=C(NC1CCc2ccccc2-n2c(Cl)cnc21)c1ncn(Cc2c(Cl)cccc2Cl)n1]

¹H NMR (400 MHz, Chloroform-d) δ 8.36 (d, J=7.8 Hz, 1H), 7.94 (s, 1H), 7.46-7.33 (m, 6H), 7.32 (dd, J=8.9, 7.1 Hz, 1H), 7.05 (s, 1H), 5.71 (s, 2H), 5.03 (dt, J=10.5, 7.8 Hz, 1H), 3.01-2.87 (m, 1H), 2.73-2.63 (m, 1H), 2.58-2.50 (app m, 1H), 2.14-2.02 (m, 1H). Purity 90%, MS (m/e) 489 (M+H)⁺.

I-80 (±)-5-Benzyl-N-(1,2-dichloro-5,6-dihydro-4H-benzo[f]imidazo[1,2-a]azepin-4-yl)-1H-1,2,4-triazole-3-carboxamide

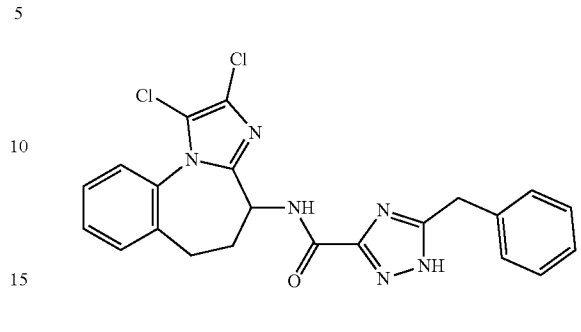

¹H NMR (400 MHz, Methanol-d₄) δ 7.56-7.43 (m, 4H), 7.36-7.20 (m, 5H), 4.95-4.86 (app m, 1H), 4.18 (s, 2H), 2.87-2.78 (m, 1H), 2.70-2.49 (m, 2H), 2.37-2.30 (m, 1H). Purity 94%, MS (m/e) 454 (M+H)⁺.

I-81 (±)-5-Benzyl-N-(1-chloro-5,6-dihydro-4H-benzo[f]imidazo[1,2-a]azepin-4-yl)-1H-1,2,4-triazole-3-carboxamide

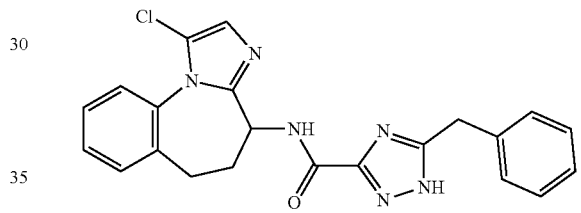

¹H NMR (400 MHz, Methanol-d₄) δ 7.58-7.41 (m, 4H), 7.38-7.18 (m, 5H), 7.03 (s, 1H), 4.89 (app dd, J=11.2, 7.7 Hz, 1H), 4.17 (s, 2H), 2.81 (dd, J=13.4, 6.2 Hz, 1H), 2.63 (tt, J=13.0, 6.8 Hz, 1H), 2.48 (td, J=13.0, 7.2 Hz, 1H), 2.31 (td, J=11.7, 7.0 Hz, 1H). Purity 93%, MS (m/e) 420 (M+H)⁺.

I-75 1-Benzyl-5-hydroxy-N-((4R)-1-oxo-4,5-dihydro-1H-benzo[b][1,2,4]oxadiazolo[4,3-d][1,4]oxazepin-4-yl)-1H-pyrazole-3-carboxamide

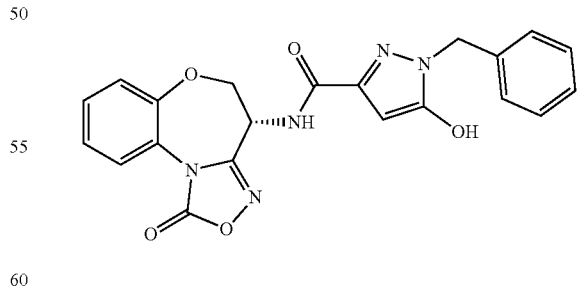

¹H NMR (400 MHz, CD₃OD) δ 7.71 (d, J=8.0 Hz, 1H), 7.52-7.15 (m, 9H), 5.46 (dd, J=9.5, 7.9 Hz, 1H), 5.18 (s, 2H), 4.65-4.48 (m, 2H). ¹³C NMR (100 MHz, CD₃OD) δ 164.6, 158.5, 158.1, 154.9, 150.9, 144.4, 138.2, 131.1, 129.6, 129.6, 128.7, 128.5, 127.3, 127.1, 125.0, 124.2, 75.6, 51.6, 45.8. MS (ESI, m/e) Calculated 419.1230; Found 420 [M+H]⁺.

I-76 (R)-1-Benzyl-5-hydroxy-N-(9-(3-hydroxy-3-methylbut-1-yn-1-yl)-4,5-dihydrobenzo[b]tetrazolo[1,5-d][1,4]oxazepin-4-yl)-1H-pyrazole-3-carboxamide

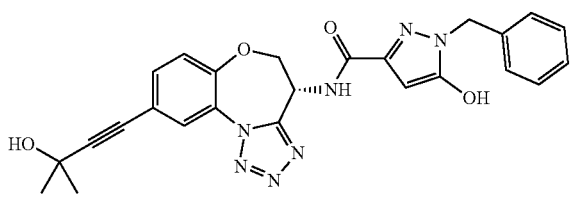 [SMILES: CC(C)(O)C#Cc1ccc2c(c1)-n1nnnc1[C@@H](NC(=O)c1cc(O)n(Cc3ccccc3)n1)CO2]

$^1$H NMR (400 MHz, CD$_3$OD) δ 8.31 (d, J=8.5 Hz, 1H), 7.41-7.13 (m, 8H), 5.91 (dd, J=6.4, 4.3 Hz, 1H), 5.14 (s, 2H), 4.56-4.39 (m, 2H), 1.57 (s, 6H). $^{13}$C NMR (100 MHz, CD$_3$OD) δ 164.3, 155.2, 155.1, 151.3, 144.7, 138.2, 129.6, 128.9, 128.6, 128.5, 127.7, 126.5, 126.3, 123.7, 97.8, 80.7, 72.1, 65.8, 51.5, 47.1, 31.5. MS (ESI, m/e) Calculated 485.1812; Found 486 [M+H]$^+$.

I-3 (R)-5-Benzyl-N-(4,5-dihydrobenzo[b]tetrazolo[1,5-d][1,4]oxazepin-4-yl)-1H-1,2,4-triazole-3-carboxamide

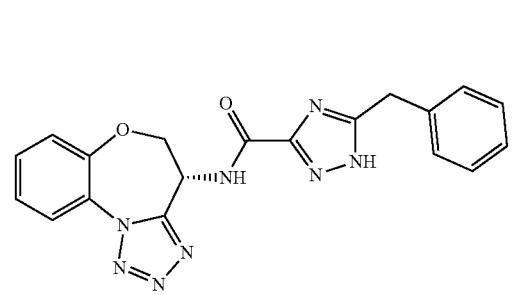 [SMILES: O=C(N[C@H]1COc2ccccc2-n2nnnc21)c1n[nH]c(Cc2ccccc2)n1]

$^1$H NMR (400 MHz, DMSO-d$_6$) δ 8.31 (dd, J=8.2, 1.6 Hz, 1H), 7.56-7.15 (m, 8H), 5.91 (td, J=7.2, 3.9 Hz, 1H), 4.50 (dd, J=12.3, 4.0 Hz, 1H), 4.39 (dd, J=12.3, 6.8 Hz, 1H), 4.12 (s, 2H). MS (ESI, m/e) Calculated 388.1396; Found 389.0 [M+H]$^+$.

I-8 (R)-5-Benzyl-N-(4,5-dihydrobenzo[b]tetrazolo[1,5-d][1,4]oxazepin-4-yl)isoxazole-3-carboxamide

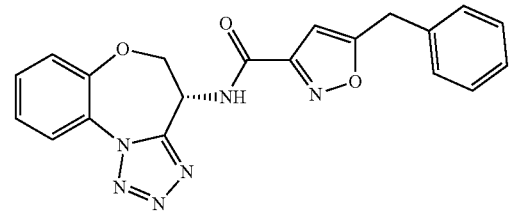 [SMILES: O=C(N[C@H]1COc2ccccc2-n2nnnc21)c1cc(Cc2ccccc2)on1]

$^1$H NMR (400 MHz, DMSO-d$_6$) δ 9.61 (d, J=8.1 Hz, 1H), 8.33 (dd, J=8.2, 1.6 Hz, 1H), 7.57-7.18 (m, 8H), 6.61 (d, J=0.8 Hz, 1H), 5.91 (ddd, J=8.2, 5.7, 3.7 Hz, 1H), 4.58-4.36 (m, 2H), 4.23 (s, 2H). MS (ESI, m/e) Calculated 388.1284; Found 389.0 [M+H]$^+$.

I-10 (R)-1-(2,6-Dichlorobenzyl)-N-(4,5-dihydrobenzo[b]tetrazolo[1,5-d][1,4]oxazepin-4-yl)-1H-1,2,4-triazole-5-carboxamide

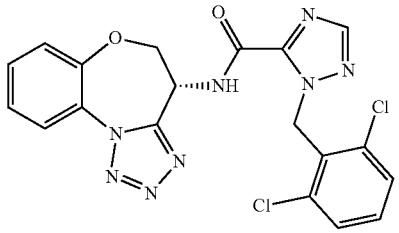 [SMILES: O=C(N[C@H]1COc2ccccc2-n2nnnc21)c1ncnn1Cc1c(Cl)cccc1Cl]

MS (ESI, m/e) Calculated 456.0617; Found 457.0 [M+H]$^+$, 455.0 [M−H].

I-11 (R)-1-(2,6-Dichlorobenzyl)-N-(4,5-dihydrobenzo[b]tetrazolo[1,5-d][1,4]oxazepin-4-yl)-1H-1,2,4-triazole-3-carboxamide

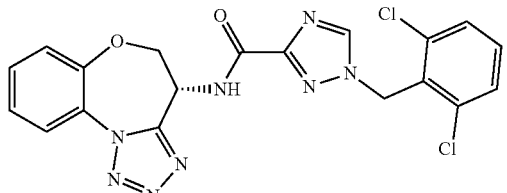

$^1$H NMR (400 MHz, DMSO-d$_6$) δ 9.35 (d, J=8.3 Hz, 1H), 8.84 (s, 1H), 8.31 (dd, J=8.2, 1.6 Hz, 1H), 7.62-7.26 (m, 5H), 5.87 (ddd, J=8.4, 6.8, 4.0 Hz, 1H), 5.71 (s, 2H), 4.58-4.30 (m, 2H). MS (ESI, m/e) Calculated 456.0617; Found 457.0 [M+H]$^+$, 455.0 [M−H]$^-$.

I-20 (R)—N-(4,5-Dihydrobenzo[b]tetrazolo[1,5-d][1,4]oxazepin-4-yl)-1-(2,6-dimethylbenzyl)-1H-1,2,4-triazole-3-carboxamide

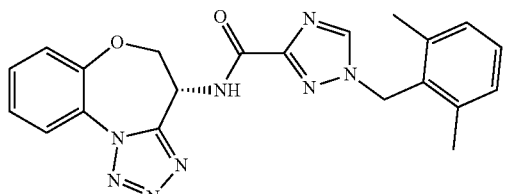

$^1$H NMR (400 MHz, DMSO-d$_6$) δ 9.33 (d, J=8.3 Hz, 1H), 8.66 (s, 1H), 8.31 (dd, J=8.3, 1.5 Hz, 1H), 7.47 (ddd, J=8.1, 7.4, 1.7 Hz, 1H), 7.38 (ddd, J=8.2, 7.3, 1.5 Hz, 1H), 7.31 (dd, J=8.1, 1.5 Hz, 1H), 7.17 (dd, J=8.3, 6.7 Hz, 1H), 7.08 (d, J=7.5 Hz, 2H), 5.87 (ddd, J=8.3, 6.9, 4.1 Hz, 1H), 5.48 (s, 2H), 4.49 (dd, J=12.3, 4.1 Hz, 1H), 4.37 (dd, J=12.3, 6.9 Hz, 1H), 2.35 (s, 6H). MS (ESI, m/e) Calculated 416.1709; Found 417.1 [M+H]$^+$, 415.1 [M−H]$^-$.

I-21 (R)—N-(4,5-Dihydrobenzo[b]tetrazolo[1,5-d][1,4]oxazepin-4-yl)-1-(2-fluorobenzyl)-1H-1,2,4-triazole-3-carboxamide

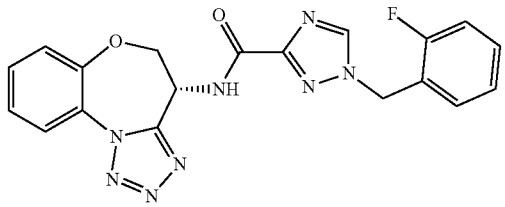 [SMILES: O=C(N[C@H]1COc2ccccc2-n2nnnc21)c1ncn(Cc2ccccc2F)n1]

¹H NMR (400 MHz, DMSO-d$_6$) δ 9.37 (d, J=8.3 Hz, 1H), 8.83 (s, 1H), 8.31 (dd, J=8.2, 1.6 Hz, 1H), 7.51-7.29 (m, 5H), 7.29-7.18 (m, 2H), 5.90 (ddd, J=8.4, 6.7, 4.0 Hz, 1H), 5.56 (s, 2H), 4.50 (dd, J=12.3, 4.0 Hz, 1H), 4.38 (dd, J=12.3, 6.7 Hz, 1H). MS (ESI, m/e) Calculated 406.1302; Found 407.0 [M+H]⁺, 405.0 [M−H]⁻.

I-41 5-Benzyl-N-((4R)-1-oxo-4,5-dihydro-1H-benzo[b][1,2,4]oxadiazolo[4,3-d][1,4]oxazepin-4-yl)-1H-1,2,4-triazole-3-carboxamide

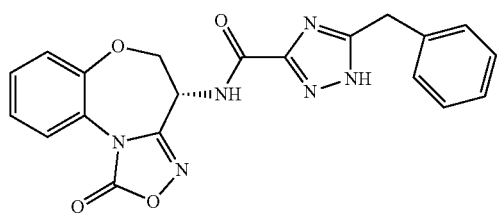 [SMILES: O=C(N[C@H]1COc2ccccc2-n2c1noc2=O)c1n[nH]c(Cc2ccccc2)n1]

¹H NMR (400 MHz, DMSO-d$_6$) δ 9.23 (br s, 1H), 7.73 (dd, J=7.9, 1.7 Hz, 1H), 7.49 (td, J=7.7, 1.8 Hz, 1H), 7.43 (td, J=7.7, 1.6 Hz, 1H), 7.38 (dd, J=7.9, 1.6 Hz, 1H), 7.33 (t, J=7.4 Hz, 2H), 7.26 (dt, J=8.1, 1.8 Hz, 3H), 5.46-5.33 (m, 1H), 4.83-4.71 (m, 1H), 4.54 (dd, J=10.5, 8.0 Hz, 1H), 4.13 (s, 2H). MS (ESI, m/e) Calculated 404.1233; Found 405.0 [M+H]⁺, 403.0 [M−H]⁻.

I-42 1-(2,6-Dichlorobenzyl)-N-((4R)-1-oxo-4,5-dihydro-1H-benzo[b][1,2,4]oxadiazolo[4,3-d][1,4]oxazepin-4-yl)-1H-1,2,4-triazole-3-carboxamide

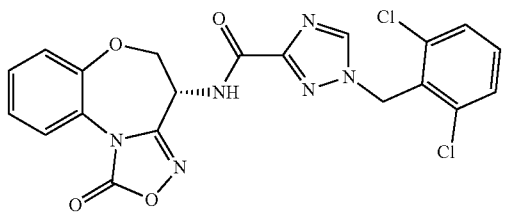 [SMILES: O=C(N[C@H]1COc2ccccc2-n2c1noc2=O)c1ncn(Cc2c(Cl)cccc2Cl)n1]

¹H NMR (400 MHz, DMSO-d$_6$) δ 9.25 (d, J=8.5 Hz, 1H), 8.88 (s, 1H), 7.73 (dd, J=7.9, 1.7 Hz, 1H), 7.58 (d, J=1.1 Hz, 1H), 7.56 (s, 1H), 7.51-7.45 (m, 2H), 7.42 (td, J=7.7, 1.6 Hz, 1H), 7.37 (dd, J=7.9, 1.6 Hz, 1H), 5.71 (s, 2H), 5.38 (dt, J=9.7, 8.1 Hz, 1H), 4.74 (t, J=10.2 Hz, 1H), 4.53 (dd, J=10.6, 7.9 Hz, 1H). MS (ESI, m/e) Calculated 472.0454; Found 473.0 [M+H]⁺, 471.0 [M−H]⁻.

I-43 5-benzyl-N-((4R)-1-oxo-4,5-dihydro-1H-benzo[b][1,2,4]oxadiazolo[4,3-d][1,4]oxazepin-4-yl)isoxazole-3-carboxamide

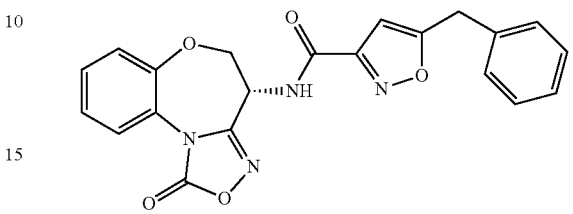

¹H NMR (400 MHz, DMSO-d$_6$) δ 9.52 (d, J=8.2 Hz, 1H), 7.72 (dd, J=7.8, 1.7 Hz, 1H), 7.49 (td, J=7.7, 1.8 Hz, 1H), 7.43 (td, J=7.7, 1.6 Hz, 1H), 7.40-7.35 (m, 2H), 7.34 (t, J=1.4 Hz, 1H), 7.32-7.25 (m, 3H), 6.59 (d, J=0.8 Hz, 1H), 5.41 (dt, J=9.5, 8.1 Hz, 1H), 4.66 (dd, J=10.7, 9.6 Hz, 1H), 4.59 (dd, J=10.7, 8.0 Hz, 1H), 4.23 (s, 2H). MS (ESI, m/e) Calculated 404.1121; Found 405.0 [M+H]⁺, 403.0 [M−H]⁻.

I-49 5-(2,4-Difluorobenzyl)-N-((4R)-1-oxo-4,5-dihydro-1H-benzo[b][1,2,4]oxadiazolo[4,3-d][1,4]oxazepin-4-yl)-1H-1,2,4-triazole-3-carboxamide

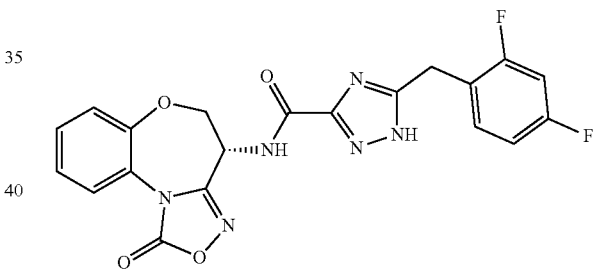

¹H NMR (400 MHz, DMSO-d$_6$) δ 7.74 (dd, J=7.8, 1.8 Hz, 1H), 7.63 (dd, J=7.9, 1.7 Hz, 1H), 7.52-7.46 (m, 1H), 7.45-7.42 (m, 2H), 7.38 (dd, J=7.7, 1.5 Hz, 2H), 7.33 (dd, J=7.9, 1.6 Hz, 1H), 5.45-5.35 (m, 1H), 4.75 (t, J=10.2 Hz, 1H), 4.58-4.51 (m, 1H), 4.25-4.16 (m, 2H). MS (ESI, m/e) Calculated 440.1045; Found 441.2 [M+H]⁺.

I-50 5-(4-Fluorobenzyl)-N-((4R)-1-oxo-4,5-dihydro-1H-benzo[b][1,2,4]oxadiazolo[4,3-d][1,4]oxazepin-4-yl)-1H-1,2,4-triazole-3-carboxamide

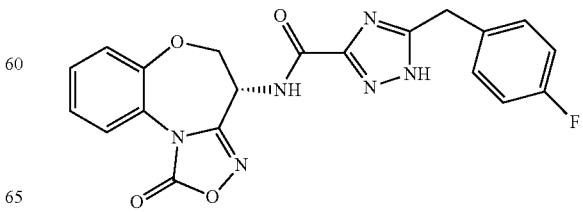

¹H NMR (400 MHz, DMSO-d₆) δ 9.18 (br s, 1H), 7.74 (dd, J=7.9, 1.7 Hz, 1H), 7.50 (dd, J=7.7, 1.8 Hz, 1H), 7.46 (dd, J=10.1, 1.8 Hz, 1H), 7.42 (dd, J=7.6, 1.6 Hz, 1H), 7.38 (dd, J=7.9, 1.6 Hz, 1H), 7.31 (ddd, J=8.5, 5.7, 2.7 Hz, 2H), 7.20-7.10 (m, 2H), 5.41 (dt, J=9.8, 8.1 Hz, 1H), 4.76 (t, J=10.2 Hz, 1H), 4.54 (dd, J=10.6, 7.8 Hz, 1H), 4.14 (s, 2H). MS (ESI, m/e) Calculated 422.1139; Found 423.2 [M+H]⁺.

I-53 N-((4R)-1-Oxo-4,5-dihydro-1H-benzo[b][1,2,4]oxadiazolo[4,3-d][1,4]oxazepin-4-yl)-4-phenoxypicolinamide

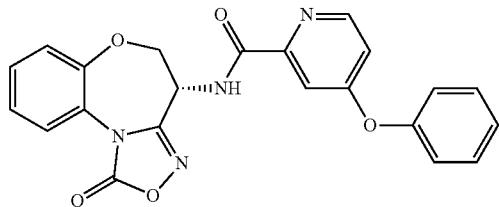 [SMILES: O=C(N[C@H]1COc2ccccc2-n2c1noc2=O)c1cc(Oc2ccccc2)ccn1]

¹H NMR (400 MHz, DMSO-d₆) δ 9.52 (d, J=8.5 Hz, 1H), 8.59 (d, J=5.6 Hz, 1H), 7.74 (dd, J=7.9, 1.7 Hz, 1H), 7.55-7.50 (m, 2H), 7.48 (dd, J=7.7, 1.8 Hz, 1H), 7.42 (td, J=7.7, 1.6 Hz, 1H), 7.39-7.31 (m, 3H), 7.26-7.21 (m, 3H), 5.42 (dt, J=9.7, 8.1 Hz, 1H), 4.81 (dd, J=10.7, 9.7 Hz, 1H), 4.55 (dd, J=10.6, 7.8 Hz, 1H). MS (ESI, m/e) Calculated 416.1121; Found 417.3 [M+H]⁺.

I-69 (R)-5-Benzyl-N-(9-(3-hydroxy-3-methylbut-1-yn-1-yl)-4,5-dihydrobenzo[b]tetrazolo[1,5-d][1,4]oxazepin-4-yl)-1H-1,2,4-triazole-3-carboxamide

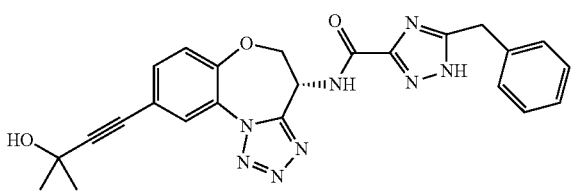 [SMILES: CC(C)(O)C#Cc1ccc2c(c1)-n1nnnc1[C@@H](NC(=O)c1n[nH]c(Cc3ccccc3)n1)CO2]

¹H NMR (400 MHz, DMSO-d₆) δ 9.30 (s, 1H), 8.29 (d, J=8.5 Hz, 1H), 7.37 (dd, J=8.6, 1.9 Hz, 1H), 7.34-7.27 (m, 2H), 7.24 (d, J=7.4 Hz, 3H), 5.90 (ddd, J=8.3, 6.3, 3.7 Hz, 1H), 4.49 (dd, J=12.4, 3.7 Hz, 1H), 4.40 (dd, J=12.4, 6.4 Hz, 1H), 4.11 (s, 2H), 1.47 (s, 6H). MS (ESI, m/e) Calculated 470.1815; Found 471.1 [M+H]⁺, 469.1 [M−H].

I-79 (R)-2-benzyl-3-chloro-5-(4,5-dihydrobenzo[b]tetrazolo[1,5-d][1,4]oxazepin-4-yl)-4,5-dihydropyrrolo[3,4-c]pyrazol-6(2H)-one

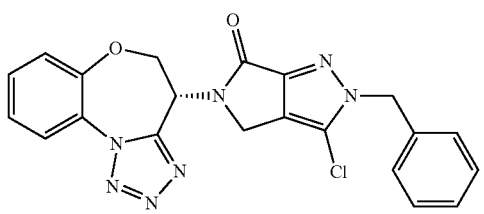 [SMILES: O=C1c2nn(Cc3ccccc3)c(Cl)c2CN1[C@H]1COc2ccccc2-n2nnnc21]

¹H NMR (400 MHz, DMSO-d₆) δ 8.32 (dd, J=8.2, 1.6 Hz, 1H), 7.53-7.47 (m, 1H), 7.44-7.29 (m, 5H), 7.27-7.23 (m, 2H), 6.07 (dd, J=5.4, 4.0 Hz, 1H), 5.52 (s, 2H), 4.74 (dd, J=12.7, 5.5 Hz, 1H), 4.62 (dd, J=12.6, 4.0 Hz, 1H), 4.58-4.26 (m, 2H). MS (ESI, m/e) Calculated 433.1054; Found 434.0 [M+H]⁺.

tert-Butyl (R)-(4,5-dihydrobenzo[b]tetrazolo[1,5-d][1,4]thiazepin-4-yl)carbamate (intermediate)

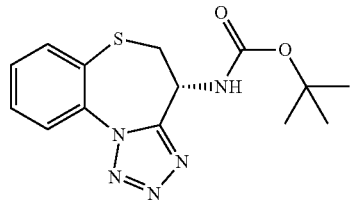 [SMILES: CC(C)(C)OC(=O)N[C@H]1CSc2ccccc2-n2nnnc21]

MS (ESI, m/e) Calculated 319.1103; Found 342.1 [M⁺Na]*, 264.1 [M−56+H]⁺.

I-22 (R)—N-(4,5-Dihydrobenzo[b]tetrazolo[1,5-d][1,4]thiazepin-4-yl)-1-(4-fluorobenzyl)-1H-1,2,4-triazole-3-carboxamide

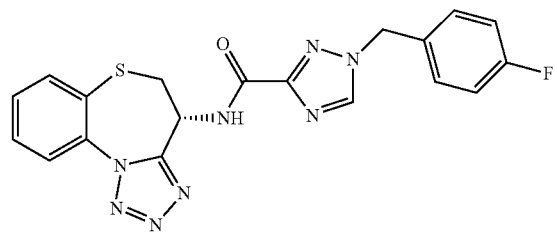 [SMILES: O=C(N[C@H]1CSc2ccccc2-n2nnnc21)c1ncn(Cc2ccc(F)cc2)n1]

¹H NMR (400 MHz, DMSO-d₆) δ 9.52 (d, J=8.2 Hz, 1H), 8.81 (s, 1H), 8.00 (dd, J=8.1, 1.3 Hz, 1H), 7.82 (dd, J=7.7, 1.5 Hz, 1H), 7.71 (ddd, J=8.0, 7.5, 1.5 Hz, 1H), 7.58 (td, J=7.6, 1.4 Hz, 1H), 7.45-7.30 (m, 2H), 7.27-7.14 (m, 2H), 5.75 (ddd, J=11.0, 8.3, 7.4 Hz, 1H), 5.47 (s, 2H), 3.69 (dd, J=13.4, 7.4 Hz, 1H), 3.30-3.16 (m, 1H). MS (ESI, m/e) Calculated 422.1074; Found 423.2 [M+H]⁺.

I-23 (R)-5-Benzyl-N-(4,5-dihydrobenzo[b]tetrazolo[1,5-d][1,4]thiazepin-4-yl)isoxazole-3-carboxamide

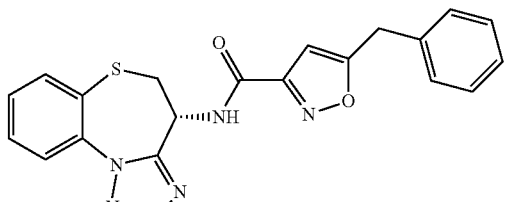

¹H NMR (400 MHz, CDCl₃) δ 8.00 (d, J=8.1 Hz, 1H), 7.88 (dd, J=8.0, 1.4 Hz, 1H), 7.80 (dd, J=7.7, 1.5 Hz, 1H), 7.62 (td, J=7.7, 1.5 Hz, 1H), 7.51 (td, J=7.7, 1.4 Hz, 1H), 7.37-7.27 (m, 3H), 7.25-7.21 (m, 2H), 5.66 (ddd, J=10.0, 8.0, 6.7 Hz, 1H), 4.11 (s, 2H), 3.93 (dd, J=12.6, 6.7 Hz, 1H), 3.27 (dd, J=12.6, 10.0 Hz, 1H). MS (ESI, m/e) Calculated 404.1055; Found 405.2 [M+H]⁺, 427.2 [M⁺Na]⁺.

I-24 (R)-5-Benzyl-N-(4,5-dihydrobenzo[b]tetrazolo[1,5-d][1,4]thiazepin-4-yl)-1H-1,2,4-triazole-3-carboxamide

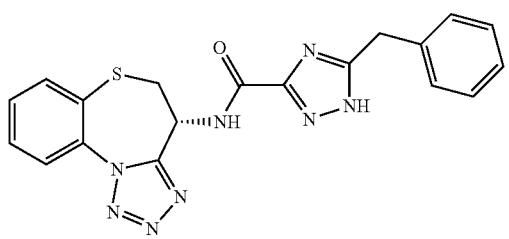 [SMILES: O=C(N[C@H]1CSc2ccccc2-n2nnnc21)c1n[nH]c(Cc2ccccc2)n1]

¹H NMR (400 MHz, CD₃OD) δ 7.98 (dd, J=8.1, 1.4 Hz, 1H), 7.84 (dd, J=7.7, 1.4 Hz, 1H), 7.74-7.64 (m, 1H), 7.56 (td, J=7.6, 1.4 Hz, 1H), 7.35-7.18 (m, 5H), 5.72 (dd, J=10.5, 7.1 Hz, 1H), 4.15 (s, 2H), 3.77 (dd, J=13.3, 7.1 Hz, 1H), 3.38 (dd, J=13.3, 10.5 Hz, 1H). MS (ESI, m/e) Calculated 404.1168; Found 405.2 [M+H]⁺.

I-25 (R)-5-Benzyl-N-(6,6-dioxido-4,5-dihydrobenzo[b]tetrazolo[1,5-d][1,4]thiazepin-4-yl)isoxazole-3-carboxamide

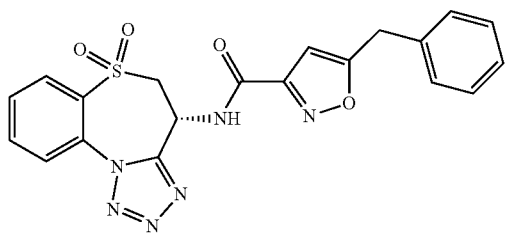 [SMILES: O=C(N[C@H]1CS(=O)(=O)c2ccccc2-n2nnnc21)c1cc(Cc2ccccc2)on1]

¹H NMR (400 MHz, DMSO-d₆) δ 9.80 (d, J=6.9 Hz, 1H), 8.22-8.07 (m, 3H), 7.95 (ddd, J=7.8, 6.7, 2.0 Hz, 1H), 7.40-7.24 (m, 5H), 6.54 (s, 1H), 5.93 (td, J=8.7, 6.9 Hz, 1H), 4.54 (dd, J=13.9, 8.3 Hz, 1H), 4.38 (dd, J=13.9, 9.2 Hz, 1H), 4.23 (s, 2H). MS (ESI, m/e) Calculated 436.0954; Found 437.2 [M+H]⁺.

I-26 5-Benzyl-N-((4R)-6-oxido-4,5-dihydrobenzo[b]tetrazolo[1,5-d][1,4]thiazepin-4-yl)isoxazole-3-carboxamide

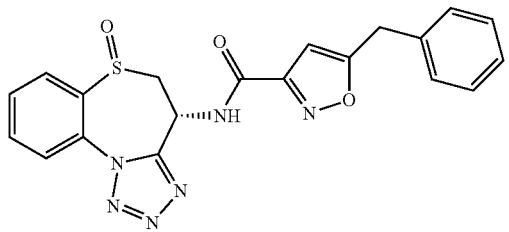 [SMILES: O=C(N[C@H]1CS(=O)c2ccccc2-n2nnnc21)c1cc(Cc2ccccc2)on1]

¹H NMR (400 MHz, DMSO-d₆) δ 9.83 (d, J=7.8 Hz, 1H), 8.05 (dd, J=7.8, 1.3 Hz, 1H), 8.02-7.92 (m, 2H), 7.83 (td, J=7.6, 1.2 Hz, 1H), 7.42-7.23 (m, 5H), 6.57 (d, J=0.8 Hz, 1H), 5.81 (dt, J=9.8, 8.0 Hz, 1H), 4.23 (s, 2H), 4.19 (dd, J=13.9, 8.0 Hz, 1H), 3.88 (dd, J=13.9, 9.9 Hz, 1H). MS (ESI, m/e) Calculated 420.1005; Found 421.0 [M+H]⁺, 443.0 [M⁺Na]⁺.

I-28 5-Benzyl-N-((4R)-1-oxo-4,5-dihydro-1H-benzo[b][1,2,4]oxadiazolo[4,3-d][1,4]thiazepin-4-yl)isoxazole-3-carboxamide

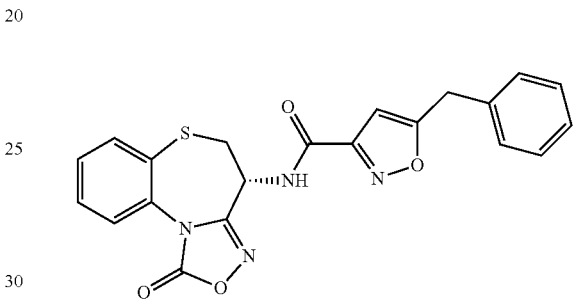

¹H NMR (400 MHz, DMSO-d₆) δ 9.63 (d, J=7.7 Hz, 1H), 7.82 (dd, J=7.7, 1.4 Hz, 1H), 7.76 (dd, J=8.0, 1.5 Hz, 1H), 7.70 (td, J=7.7, 1.5 Hz, 1H), 7.55 (td, J=7.5, 1.6 Hz, 1H), 7.39-7.25 (m, 5H), 6.54 (d, J=0.8 Hz, 1H), 5.05 (dt, J=10.1, 7.7 Hz, 1H), 4.22 (s, 2H), 3.74 (dd, J=12.1, 7.7 Hz, 1H), 3.44 (dd, J=12.1, 10.1 Hz, 1H). MS (ESI, m/e) Calculated 420.0892; Found 421.2 [M+H]⁺.

I-30 (R)—N-(4,5-Dihydrobenzo[b]tetrazolo[1,5-d][1,4]thiazepin-4-yl)-5-(4-fluorobenzyl)-1H-1,2,4-triazole-3-carboxamide

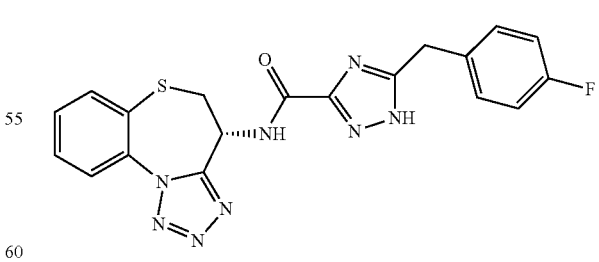

¹H NMR (400 MHz, CD₃OD) δ 7.98 (dd, J=8.0, 1.4 Hz, 1H), 7.84 (dd, J=7.7, 1.5 Hz, 1H), 7.69 (td, J=7.8, 1.5 Hz, 1H), 7.57 (td, J=7.6, 1.4 Hz, 2H), 7.38-7.22 (m, 2H), 7.04 (t, J=8.8 Hz, 2H), 5.72 (dd, J=10.5, 7.1 Hz, 1H), 4.15 (s, 2H), 3.77 (dd, J=13.3, 7.1 Hz, 1H), 3.38 (dd, J=13.3, 10.5 Hz, 1H). MS (ESI, m/e) Calculated 422.1074; Found 421.3 [M−H]⁻.

I-31 5-(4-Fluorobenzyl)-N-((4R)-1-oxo-4,5-dihydro-1H-benzo[b][1,2,4]oxadiazolo[4,3-d][1,4]thiazepin-4-yl)-1H-1,2,4-triazole-3-carboxamide

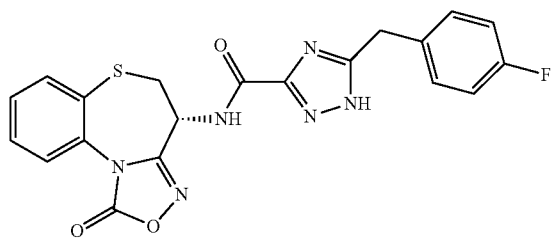 [SMILES: O=C(N[C@H]1CSc2ccccc2-n2c1noc2=O)c1n[nH]c(Cc2ccc(F)cc2)n1]

$^1$H NMR (400 MHz, CD$_3$OD) δ 7.83 (dd, J=7.7, 1.4 Hz, 1H), 7.71 (dd, J=8.0, 1.5 Hz, 1H), 7.69-7.63 (m, 1H), 7.51 (td, J=7.5, 1.6 Hz, 1H), 7.33-7.27 (m, 2H), 7.10-7.01 (m, 2H), 5.15 (dd, J=10.3, 7.6 Hz, 1H), 4.15 (s, 2H), 3.78 (dd, J=12.1, 7.6 Hz, 1H), 3.35 (dd, J=12.1, 10.3 Hz, 1H). MS (ESI, m/e) Calculated 438.0910; Found 439.2 [M+H]$^+$.

I-32 1-(4-Fluorobenzyl)-N-((4R)-1-oxo-4,5-dihydro-1H-benzo[b][1,2,4]oxadiazolo[4,3-d][1,4]thiazepin-4-yl)-1H-1,2,4-triazole-3-carboxamide

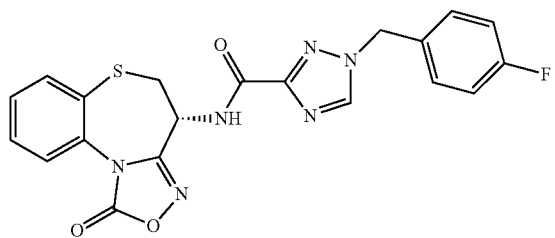 [SMILES: O=C(N[C@H]1CSc2ccccc2-n2c1noc2=O)c1ncn(Cc2ccc(F)cc2)n1]

$^1$H NMR (400 MHz, DMSO-d$_6$)$_6$ 9.36 (d, J=8.2 Hz, 1H), 8.83 (s, 1H), 7.82 (dd, J=7.7, 1.4 Hz, 1H), 7.76 (dd, J=8.0, 1.5 Hz, 1H), 7.73-7.67 (m, 1H), 7.55 (td, J=7.5, 1.6 Hz, 1H), 7.41-7.35 (m, 2H), 7.25-7.18 (m, 2H), 5.48 (s, 2H), 5.04 (dt, J=10.2, 7.9 Hz, 1H), 3.70 (dd, J=12.0, 7.8 Hz, 1H), 3.57 (dd, J=12.0, 10.3 Hz, 1H). MS (ESI, m/e) Calculated 438.0910; Found 439.2 [M+H]$^+$.

I-33 5-Benzyl-N-((4R)-1-oxo-4,5-dihydro-1H-benzo[b][1,2,4]oxadiazolo[4,3-d][1,4]thiazepin-4-yl)-1H-1,2,4-triazole-3-carboxamide

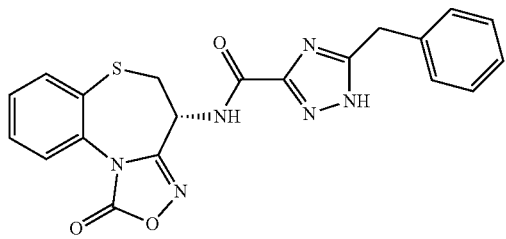 [SMILES: O=C(N[C@H]1CSc2ccccc2-n2c1noc2=O)c1n[nH]c(Cc2ccccc2)n1]

$^1$H NMR (400 MHz, CD$_3$OD) δ 7.83 (dd, J=7.7, 1.5 Hz, 1H), 7.71 (dd, J=8.0, 1.6 Hz, 1H), 7.65 (td, J=7.7, 1.5 Hz, 1H), 7.51 (td, J=7.5, 1.6 Hz, 1H), 7.35-7.22 (m, 5H), 5.15 (dd, J=10.3, 7.6 Hz, 1H), 4.17 (s, 2H), 3.78 (dd, J=12.1, 7.5 Hz, 1H), 3.35 (dd, J=12.1, 10.3 Hz, 1H). MS (ESI, m/e) Calculated 420.1005; Found 421.2 [M+H]$^+$.

I-46 5-Benzyl-N-((4R)-1-oxo-4,5-dihydro-1H-[1,2,4]oxadiazolo[4,3-d]pyrido[2,3-b][1,4]oxazepin-4-yl)isoxazole-3-carboxamide

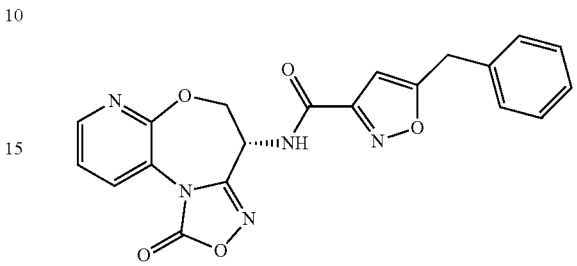

MS (ESI, m/e) Calculated 405.1073; Found 406.1 [M+H]$^+$.

The compounds disclosed herein can be identified and evaluated using the following assays.

Identification of Biological Activity

In this example, compounds of the disclosure were evaluated using a biochemical assay using the ADP-Glo™ technology.

ADP-Glo™ (Promega, Madison, WI, USA) reagents were thawed at ambient temperature. Kinase Detection Reagent was prepared by mixing kinase detection buffer with the lyophilized kinase detection substrate.

A 500 ml stock volume of 5× Reaction Kinase Buffer was made by mixing 1000 µl of 1M MgCl$_2$, 500 µl of 1M Tris-HCL pH7.4, 0.5 mg/ml (25 mg) of BSA, and 3475 µl of distilled H$_2$O. A 3 ml 2× working stock volume of Reaction Kinase Buffer was made containing a final concentration of 100 µM DTT and 4 mM MnCl$_2$.

Components of RIPK1 enzyme (Rigel Pharmaceuticals, South San Francisco, CA, USA) were thawed on ice. Diluted RIPK1 was prepared in 1× Kinase Reaction Buffer (diluted from 2× buffer) to 31 ng/well. A 166 M working stock ATP assay solution was prepared in 1× Kinase Reaction Buffer (diluted from 2× buffer).

Compounds were serially diluted in DMSO from 250 uM in 4-fold dilutions then diluted 1:5 in 2× Reaction Buffer in a 96 well plate. 1.0 ul of diluted compound was added to a 384 well plate in duplicate. 2 µl of diluted Active RIPK1 was added to 384 well plate (do not add to column 1) add 2×rxn buffer to column 1. AKT (Anaspec, Fremont, CA, USA) at 150 nM was combined with ATP working stock at equal volume and 2 ul/well were added to the 384 well plate. The final reaction volume was 5.0 µl. The plate was quickly centrifuged and the reaction was incubated at 30° C. for 30 minutes. Adding 5 µl of ADP-Glo™ terminated the reaction. The plate was quickly centrifuged and the reaction was incubated at room temperature for 40 minutes. Kinase Detection Reagent was then added and incubated at room temperature for 30 minutes. The relative light unit (RLU) of kinase reaction was determined by luminescent (Luminescence 0.1 s) using a Wallac Victor2 Luminometer (PerkinElmer, Waltham, MA, USA). IC$_{50}$ values obtained from this example are provided by Table 2. The data in Table 2 establish that compounds of the present invention inhibit RIP1K.

TABLE 2

| Compound | RIPK1 ADP-Glo Kinase (IC$_{50}$) |
| --- | --- |
| I-1 | 0.0676 |
| I-2 | 6.23 |
| I-3 | 0.0582 |
| I-4 | 0.0545 |
| I-5 | 7.628 |
| I-6 | Not determined |
| I-7 | 0.0225 |
| I-8 | 0.5213 |
| I-9 | 0.0261 |
| I-10 | Not determined |
| I-11 | 0.0178 |
| I-12 | 6.712 |
| I-13 | 0.0081 |
| I-14 | 0.0166 |
| I-19 | 0.3929 |
| I-20 | 1.871 |
| I-21 | 0.0567 |
| I-22 | 0.0321 |
| I-23 | 0.0429 |
| I-24 | 0.0272 |
| I-25 | 0.5101 |
| I-26 | 1.373 |
| I-27 | 0.0684 |
| I-28 | 0.0679 |
| I-29 | 0.0098 |
| I-30 | 0.0186 |
| I-31 | 0.0158 |
| I-32 | 0.0133 |
| I-33 | 0.0125 |
| I-34 | 0.1386 |
| I-35 | 2.077 |
| I-36 | 2.803 |
| I-37 | 1.144 |
| I-38 | 0.0223 |
| I-39 | 1.463 |
| I-40 | Not determined |
| I-41 | 0.058 |
| I-42 | 0.0263 |
| I-43 | 0.1098 |
| I-44 | 0.9471 |
| I-45 | 0.0312 |
| I-46 | 4.408 |
| I-47 | 0.0873 |
| I-48 | 0.0534 |
| I-49 | 0.347 |
| I-50 | 0.1088 |
| I-51 | 0.0492 |
| I-52 | 0.0325 |
| I-53 | 0.0204 |
| I-54 | 0.5823 |
| I-55 | 0.089 |
| I-56 | 0.0561 |
| I-57 | 0.663 |
| I-58 | 0.0573 |
| I-59 | 0.1182 |
| I-60 | 1.289 |
| I-61 | 0.0862 |
| I-62 | 0.0695 |
| I-63 | 0.1335 |
| I-64 | 0.1245 |
| I-65 | 0.0678 |
| I-66 | 13.49 |
| I-67 | 11.38 |
| I-68 | 0.1178 |
| I-69 | 0.0601 |
| I-70 | Not determined |
| I-71 | 0.58 |
| I-72 | 0.2192 |
| I-73 | 0.0924 |
| I-74 | 0.054 |
| I-75 | 10.57 |
| I-76 | Not determined |
| I-77 | 0.1106 |
| I-78 | 0.0396 |
| I-79 | 0.6523 |
| I-80 | 1.874 |
| I-81 | 0.5173 |
| I-82 | 0.04 |
| I-83 | 0.0435 |
| I-84 | 0.1185 |
| I-85 | 0.1685 |
| I-86 | 0.067 |
| I-87 | 0.0682 |
| I-88 | 0.1119 |
| I-89 | 0.1077 |
| I-90 | 0.0531 |
| I-91 | Not determined |
| I-92 | 0.0282 |
| I-93 | 0.0404 |

Whole Cell Assays

In this example, U937 and L929 cells were exposed to compounds of the present disclosure and a cell necroptosis assay was conducted to evaluate compound activity in functional human RIP1 and murine RIP1 assays.

U937 and L929 cells were obtained from the American Type Culture Collection (Manassas, VA, USA). Both cells were maintained in logarithmic growth phase in complete RPMI 1640 media (Sigma, ST Louis, MO, USA) supplemented with 10% fetal bovine serum (Sigma, ST Louis, MO, USA) at 37° C. with 5% $CO_2$. For necroptosis assay, L929 cells were plated for 18 h in 100 μL/well medium at 10K cells/well in Costar 96-well black clear-bottom plates (Fisher Scientific, Hampton, NH, USA); U937 cells were plated on the day of the assay in 50 μL/well medium containing 60 uM zVAD-fmk (Lonza, Basel, Switzerland) at 50K cells/well. Medium from L929 cells were removed from the 96-well plates and replaced with 50 μL/well new medium containing 40 uM zVAD-fmk. Each compound of the present disclosure evaluated in this example was serially diluted in DMSO from 2.5 mM in 4-fold dilutions, and then diluted 1:125 in complete medium. 50 μL/well 2× of the compound was then added to the cells in the plates. The cells were pre-incubated with the compound for 1 hour at 37° C. with 5% $CO_2$ and before addition of 10 μL/well 11×TNFa (Peprotech, Rocky Hill, NJ, USA) to give a final concentration of 2 ng/mL for TNFa. The relative amount of necroptosis cells was determined by luminescent using a Wallac Victor2 Luminometer (PerkinElmer, Waltham, MA, USA) and a CellTiter-Glo® Luminescent Cell Viability Reagent Assay (Promega, Madison, WI, USA) added per manufacturer instructions after 18 hours of TNFa stimulation at 37° C. with 5% $CO_2$. Results from this example are summarized in Table 3. This example establishes that embodiments of the compounds described herein have unexpectedly potent activity against human RIP1 and murine RIP1, which allows their assessment in in vivo mouse models of disease. These results are useful in determining safe and effective doses for humans.

TABLE 3

| Compound | U937 Zvad TNF CTG Recovery, U937, TNFa + zVAD (IC$_{50}$) | L929-CTG-recovery, L929, TNFa + zVAD (IC$_{50}$) |
| --- | --- | --- |
| I-1 | 0.3756 | 9999 |
| I-2 | 40.27 | 9999 |
| I-3 | 4.08 | 9999 |
| I-4 | 0.2029 | 9999 |
| I-5 | 86.64 | 9999 |
| I-6 | 884.7 | 9999 |
| I-7 | 0.0137 | 12.7 |
| I-8 | 4.445 | 9999 |

TABLE 3-continued

| Compound | U937 Zvad TNF CTG Recovery, U937, TNFa + zVAD (IC$_{50}$) | L929-CTG-recovery, L929, TNFa + zVAD (IC$_{50}$) |
|---|---|---|
| I-9 | 0.2216 | 9999 |
| I-10 | 5015 | 9999 |
| I-11 | 0.0343 | 9999 |
| I-12 | 17 | 9999 |
| I-13 | 0.003 | 3.375 |
| I-14 | 0.0066 | 2.337 |
| I-19 | 0.9604 | 9999 |
| I-20 | 1.565 | |
| I-21 | 0.0625 | 159.8 |
| I-22 | 0.002 | 2.485 |
| I-23 | 0.1009 | 9999 |
| I-24 | 0.0144 | 2.143 |
| I-25 | 28.6 | 9999 |
| I-26 | 0.1762 | 9999 |
| I-27 | 0.034 | 5.55 |
| I-28 | 0.0165 | 10.73 |
| I-29 | 0.0011 | 0.1945 |
| I-30 | 0.0679 | 9999 |
| I-31 | 0.014 | 5009 |
| I-32 | 0.0016 | 0.6741 |
| I-33 | 0.0056 | 5.163 |
| I-34 | 1.544 | 9999 |
| I-35 | 2.681 | 9999 |
| I-36 | 0.7144 | 16.11 |
| I-37 | 4.067 | 9999 |
| I-38 | 0.0439 | 9.786 |
| I-39 | 1.377 | 50.88 |
| I-40 | 9999 | 9999 |
| I-41 | 0.0481 | 9999 |
| I-42 | 0.041 | 9999 |
| I-43 | 0.2046 | 9999 |
| I-44 | 1.665 | 9999 |
| I-45 | 0.0364 | 10.46 |
| I-46 | 39.4 | 9999 |
| I-47 | 0.0257 | 9.496 |
| I-48 | 0.0408 | 9999 |
| I-49 | 0.7167 | 9999 |
| I-50 | 0.2459 | 9999 |
| I-51 | 0.1254 | 17.08 |
| I-52 | 0.0647 | 20.75 |
| I-53 | 0.0462 | 30.7 |
| I-54 | 1.245 | 9999 |
| I-55 | 0.0206 | 9.496 |
| I-56 | 0.0345 | 5.092 |
| I-57 | 3.649 | 9999 |
| I-58 | 0.0743 | 9999 |
| I-59 | 0.8294 | 9999 |
| I-60 | 35.76 | 9999 |
| I-61 | 0.0181 | 0.1062 |
| I-62 | 0.0301 | 10.13 |
| I-63 | 0.2895 | 9999 |
| I-64 | 0.0077 | 4.059 |
| I-65 | 0.0211 | 3.261 |
| I-66 | 9999 | 9999 |
| I-67 | 9999 | 9999 |
| I-68 | 0.0252 | 8.672 |
| I-69 | 0.7868 | 9999 |
| I-70 | 73.41 | 9999 |
| I-71 | 3.483 | 9999 |
| I-72 | 0.7081 | 9999 |
| I-73 | 0.9028 | 9999 |
| I-74 | 0.0898 | 8.624 |
| I-75 | 9999 | 9999 |
| I-76 | 9999 | 9999 |
| I-77 | 0.0096 | 4.085 |
| I-78 | 0.0022 | 0.0061 |
| I-79 | 16.06 | 9999 |
| I-80 | 83.41 | 9999 |
| I-81 | 4.245 | 9999 |
| I-82 | 0.0084 | 5.292 |
| I-83 | 0.0043 | 2.123 |
| I-84 | 0.0386 | 8.786 |
| I-85 | 0.0309 | 1.353 |
| I-86 | 0.0119 | 3.447 |
| I-87 | 0.0156 | 9999 |
| I-88 | 0.1625 | 9999 |
| I-89 | 0.0352 | 7.93 |
| I-90 | 0.1698 | 9999 |
| I-91 | 9999 | 9999 |
| I-92 | 0.0676 | 6 |
| I-93 | 0.0371 | 5.168 |

IN VIVO ACTIVITY

In this example, an acute hypothermia mouse model assay was used to evaluate the ability of compounds disclosed herein to inhibit TNF-alpha induced hypothermia.

Female C57BL/6 mice are randomly grouped and weighed on Day −1. On the day of the study (Day 0), mice are administered vehicle or test article by oral gavage. Fifteen minutes after oral administration of test agents, each mouse is administered an intraperitoneal (IP) injection of solution containing recombinant human tumor necrosis factor alpha (TNF-a, 25.0 μg) and zVAD-FMK (200 μg). Body temperature is measured at hour zero (before IP injections) and every hour via rectal probe temperature measuring device. Three (3) hours after IP injections of TNF-α and zVAD/FMK, mice are euthanized by $CO_2$ asphyxiation and blood is collected via cardiac puncture. Serum and plasma are harvested for determination of cytokine and compound levels, respectively. Separate groups of mice (satellite mice) are included for the determination of compound levels in plasma at the time of administration of TNFa/zVAD-FMK. Activity in this example demonstrates that embodiments of the presently disclosed compounds inhibit TNF-alpha signaling in vivo and as such can be used to treat diseases in which TNF-alpha is implicated.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A method of treating a RIP1K associated condition in a subject, comprising administering to the subject a therapeutically effective amount of a compound of formula

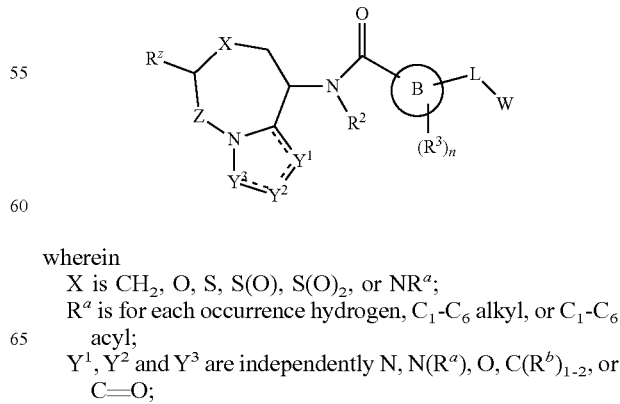

wherein
X is $CH_2$, O, S, S(O), S(O)$_2$, or NR$^a$;
R$^a$ is for each occurrence hydrogen, $C_1$-$C_6$ alkyl, or $C_1$-$C_6$ acyl;
Y$^1$, Y$^2$ and Y$^3$ are independently N, N(R$^a$), O, C(R$^b$)$_{1-2}$, or C=O;

$R^b$ is hydrogen, $C_{1-6}$alkyl, or halo;

Z is $C(R^c)$ or $NR^c$;

$R^c$ is a $C_1$-$C_4$ alkyl unsaturated carbon chain optionally substituted with one or more $R^1$ groups, optionally interrupted by 1 or 2 heteroatoms selected from O, N and S;

$R^z$ is N, CH or $C(R^1)$ and together with $ZR^c$ and the carbon to which they are bound form a 5- or 6-membered heteroaryl or 6-membered aryl, wherein the 5- or 6-membered heteroaryl or 6-membered aryl is substituted with m $R^1$ groups;

$R^1$ is a linker-$R^6$ group, wherein the linker is a bond, $C_1$-$C_4$ alkyl, $C_2$-$C_4$ alkenyl, or $C_2$-$C_4$ alkynyl, wherein the $C_1$-$C_4$ alkyl, $C_2$-$C_4$ alkenyl, or $C_2$-$C_4$ alkynyl is optionally substituted by one or more $R^b$, and $R^6$ is $R^e$, —$C(R^f)_3$, or —$C(R^f)$=$C(R^f)_2$;

$R^2$ is $R^a$;

ring B is 5- to 10-membered heteroaryl;

$R^3$ is, for each occurrence, independently is $R^b$ or $OR^a$;

L is O, $NR^a$, or alkylene;

W is 5- to 10-membered aryl or 5- to 10-membered heteroaryl, wherein the 5- to 10-membered aryl or 5- to 10-membered heteroaryl is substituted by p $R^4$;

$R^4$ is for each occurrence selected from $R^b$ and $OR^a$;

$R^d$ is for each occurrence independently selected from hydrogen, $C_1$-$C_6$ alkyl, aralkyl, $C_{5-10}$ aryl or heteroaryl, or two Rd together with a nitrogen to which they are both attached form a $C_{3-10}$heterocyclic group optionally substituted by one or more Re;

$R^e$ is independently for each occurrence halo, —$OR^d$, —$SR^d$, —$S(O)_2R^d$, —$NR^dR^d$, —$Si(R^a)_3$, —$C(O)OH$, —$C(O)OR^a$, or —$C(O)NR^dR^d$, $R^f$ is independently for each occurrence $R^a$, $R^b$, or $R^e$, or two $R^f$ groups together with the carbon atom bound thereto provide a $C_3$-$C_6$ cycloalkyl or a $C_3$-$C_{10}$ heterocyclic, wherein the $C_3$-$C_6$ cycloalkyl or $C_3$-$C_{10}$ heterocyclic is optionally substituted with one or more Re;

m is 1, 2, 3, or 4;

n is 0, 1 or 2; and p is 0, 1, 2, 3, 4, or 5;

wherein the RIP1K associated condition is Parkinson's disease, Alzheimer's disease, or multiple sclerosis.

2. The method of claim 1, wherein the RIP1K associated condition is Parkinson's disease.

3. The method of claim 1, wherein the RIP1K associated condition is Alzheimer's disease.

4. The method of claim 1, wherein the RIP1K associated condition is multiple sclerosis.

\* \* \* \* \*